US012782359B2

(12) United States Patent
Heffron et al.

(10) Patent No.: US 12,782,359 B2
(45) Date of Patent: Nov. 3, 2026

(54) PLASMID FOR BACILLUS EXPRESSING FLUORESCENT REPORTER GENES

(71) Applicant: Novozymes BioAg A/S, Bagsvaerd (DK)

(72) Inventors: Jared Heffron, Salem, VA (US); John William Rice, Pittsboro, NC (US)

(73) Assignee: Novozymes BioAg A/S, Bagsvaerd (DK)

( * ) Notice: Subject to any disclaimer, the term of this patent is extended or adjusted under 35 U.S.C. 154(b) by 1057 days.

(21) Appl. No.: 17/793,337

(22) PCT Filed: Jan. 15, 2021

(86) PCT No.: PCT/US2021/013529
§ 371 (c)(1),
(2) Date: Jul. 15, 2022

(87) PCT Pub. No.: WO2021/146492
PCT Pub. Date: Jul. 22, 2021

(65) Prior Publication Data

US 2023/0058264 A1 Feb. 23, 2023

Related U.S. Application Data

(60) Provisional application No. 62/962,033, filed on Jan. 16, 2020.

(51) Int. Cl.

| | |
|---|---|
| ***C12N 15/00*** | (2006.01) |
| ***C07K 14/32*** | (2006.01) |
| ***C12N 1/20*** | (2006.01) |
| ***C12N 15/75*** | (2006.01) |
| ***G01N 33/58*** | (2006.01) |

(52) U.S. Cl.
CPC ........... *G01N 33/582* (2013.01); *C07K 14/32* (2013.01); *C12N 1/20* (2013.01); *C12N 15/75* (2013.01); *C07K 2319/60* (2013.01)

(58) Field of Classification Search
None
See application file for complete search history.

(56) References Cited

U.S. PATENT DOCUMENTS

2009/0286244 A1 11/2009 Dean

FOREIGN PATENT DOCUMENTS

WO 1999043835 A2 9/1999

OTHER PUBLICATIONS

Doherty et al, 2010, BMC Research notes 3, 303.
Eijlander et al, 2013, Appl Environ Microbiol 79(18), 5643-5651.
Kang et al, 2019, Appl Biol Chem 62, 41.
Karava et al, 2019, PLOS ONE 14(7), e0219892.
Mamou et al, 2016, Cell reports 14, 1850-1857.
Parente et al., 2008, Can J Microbiol 54, 786-790.
Rosenberg et al, 2012, PLOS ONE 7(7), e41921.
Segev et al, 2013, J Bacteriol 195(9), 1875-1882.
Setlow, 1988, Annual Review of Microbiology 42, 319-338.

*Primary Examiner* — Jennifer E Graser
(74) *Attorney, Agent, or Firm* — Adam Rucker

(57) ABSTRACT

The present invention relates to fluorescence reporter plasmid systems for enabling a *Bacillus* strain to fluoresce, and to methods for visualizing the state of *Bacillus* strains.

20 Claims, 10 Drawing Sheets

Specification includes a Sequence Listing.

PLASMID FOR BACILLUS EXPRESSING FLUORESCENT REPORTER GENES

CROSS-REFERENCE TO RELATED APPLICATIONS

This application is a 35 U.S.C. 371 national application of international application no. PCT/US2021/013529 filed Jan. 15, 2021, which claims priority or the benefit under 35 U.S.C. 119 of U.S. provisional application No. 62/962,033 filed Jan. 16, 2020, the contents of which are fully incorporated herein by reference.

REFERENCE TO SEQUENCE LISTING

This application contains a Sequence Listing in computer readable form. The contents of the electronic sequence listing created on Jan. 15, 2021, named 14940-WO-PCT Sequence listing ST25-for filing.txt and 140 KB in size, is hereby incorporated by reference in its entirety.

FIELD OF THE INVENTION

The present invention relates to fluorescence reporter plasmid systems for enabling a *Bacillus* strain to fluoresce and to methods for visualizing the state of *Bacillus* strains.

BACKGROUND OF THE INVENTION

The paper "Molecular Kinetics of Reviving Bacterial Spores" (Segev E. et al., 2013. J Bacteriol 195:1875-82) utilizes two different strains containing translational fusions of a Green Fluorescent Protein (GFP) to either RplA or SspA in *B. subtilis*. The original construction of these strains was detailed in a previous work by the same research group (Rosenberg A, Sinai L, Smith Y, Ben-Yehuda S. 2012. Dynamic expression of the translational machinery during *Bacillus subtilis* life cycle at a single cell level. PLoS One 7:e41921), and similar fusions have been used to follow *Bacillus* colony morphology (Mamou G, Malli Mohan G B, Rouvinski A, Rosenberg A, Ben-Yehuda S. 2016. Early Developmental Program Shapes Colony Morphology in Bacteria. Cell Rep 14:1850-7). In these previous studies the strains of interest contained a single genetic circuit to permit fluorescence of only type; multiple strains were developed to elicit fluorescence from more than one gene.

SUMMARY OF THE INVENTION

The invention provides a fluorescence reporter plasmid system for enabling a *Bacillus* strain to fluoresce, wherein the *Bacillus* strain fluoresces in its dormant endospore state and/or in its metabolically active vegetative state, and wherein the plasmid system is designed to function extra-chromosomally. The plasmid system enables in one aspect a *Bacillus* strain to fluoresce after the plasmid has been transformed into the *Bacillus* cell, wherein the *Bacillus* strain fluoresces in its dormant endospore state and/or in its metabolically active vegetative state. In another or further aspect, the *Bacillus* strain fluoresces a first fluorescent colour when in its dormant endospore state and a second fluorescent colour when in its metabolically active vegetative state, and wherein the first fluorescent colour differs from the second fluorescent colour.

The invention further provides a method of visualizing the state of *Bacillus* strains in an animal, a plant or a plant seed comprising a. combining a *Bacillus* strain and a cell comprising a single or dual reporter plasmid system for enabling the *Bacillus* strain to fluoresce one fluorescent colour when in dormant endospore state and/or another fluorescent colour when in metabolically active vegetative state,
b. treating an animal or a plant seed with the *Bacillus* strain of step (a),
c. collecting samples from the treated animal or plant seed of step (b),
d. optionally staining the samples of step (c) with DNA dyes, and
e. imaging the samples of step (c) or (d) to visualize the the state of the *Bacillus* strain.

Also comprised herein is a method of visualizing the state of *Bacillus* strains in vitro or in vivo, wherein a plasmid system is used for enabling the *Bacillus* strains to fluoresce in the dormant endospore state and/or the metabolically active vegetative state, wherein the fluorescence of the *Bacillus* strains indicates the state of the strain.

DEFINITIONS

Figure 1:
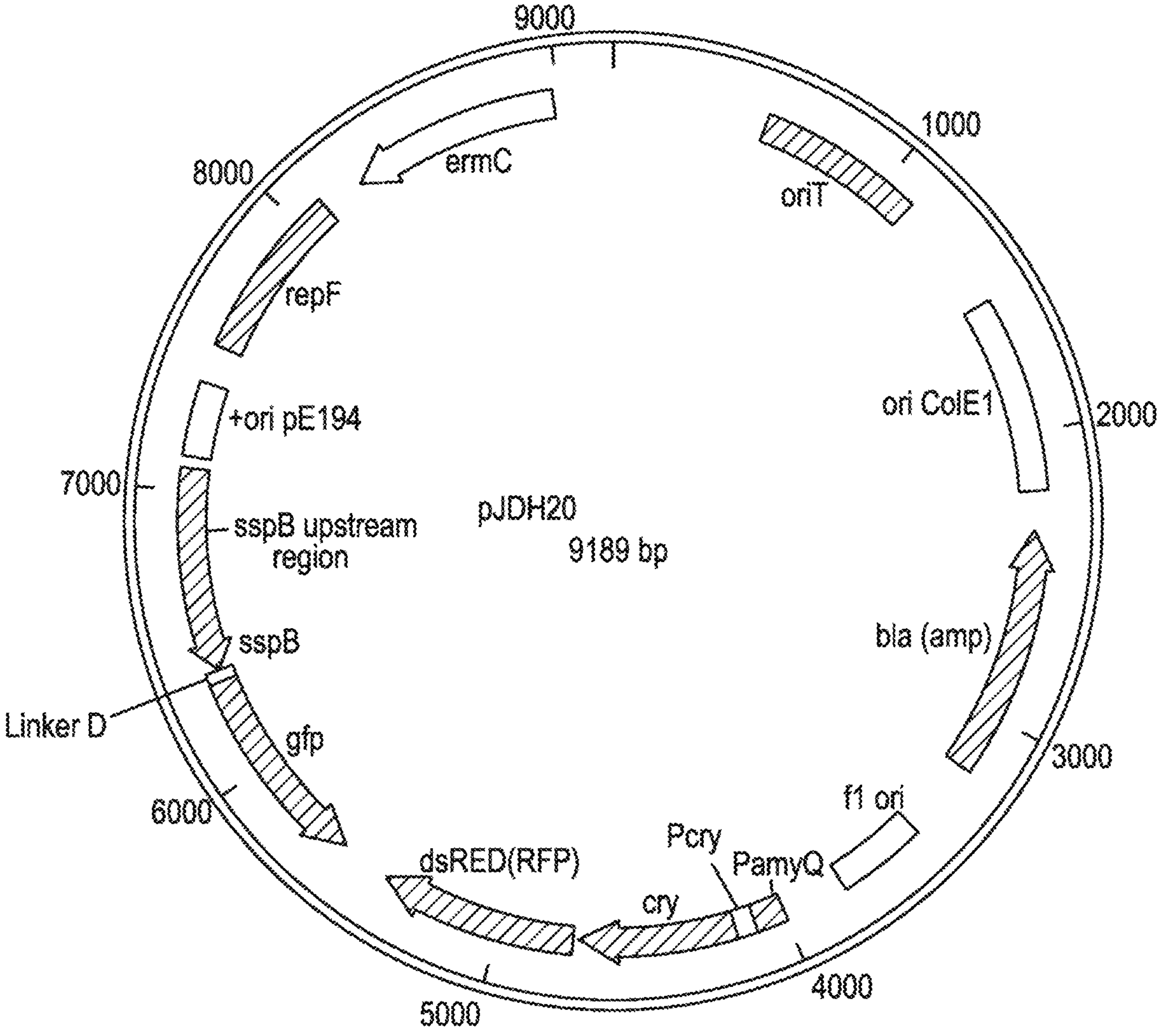
FIG. 1 shows a plasmid map for the dual reporter plasmid pJDH20 (SEQ ID No: 5).

The following includes definitions of selected terms that may be used throughout the disclosure and in the claims. The definitions include various examples and/or forms of components that fall within the scope of a term and that may be used for implementation. The examples are not intended to be limiting. Both singular and plural forms of terms fall within the definitions.

Able to germinate: The term "able to germinate" in reference to bacterial spores, means that at least some of the spores in a population will germinate when provided with sufficient germinants.

About: The term means±10% with respect to the stated value or property.

Plasmid: A small double-stranded DNA molecule that is maintained within a cell, but physically separate from the larger chromosomal DNA molecule. They replicate independently and are circular.

Backbone of the plasmid: "Backbone of the plasmid" or "plasmid backbone" refers to a genetically engineered plasmid designed as a template for easy additional genetic manipulation. The backbone at least comprises selectable marker(s) used for selection of the plasmid in the bacterial host, a multiple cloning site region(s) used for integration of foreign DNA into the plasmid, any origin of replication that is required for replication in potential hosts of the molecule. It may also contain an origin of transfer (oriT) in order to transfer the plasmid from one bacterial host to another.

Transformation: The process of introducing foreign DNA (such as a plasmid) into a cell.

Bacteria: Means prokaryotic organisms that have peptidoglycan in their cell walls and have lipids that contain fatty acids in their membranes.

Bacterial spores: Refers to the structures formed by some bacteria during a process called sporulation. Generally, bacterial spores are resistant to environmental conditions, metabolically inactive, and unable to reproduce. Bacterial spores are generally able to germinate into vegetative cells.

Custom made: The term "custom made" of a plasmid is used to describe a plasmid which is designed for a specific recipient bacterial species. A plasmid system which is not custom made is thus a plasmid system designed for recipients of a bacterial genera but not a species.

Dormant endospore state: A state in the life cycle of endospore-producing bacteria where they are in a stable resting, non-reproductive and enzymatically inert (termed "dormant") form.

Endospore: Means a type of spore that develops inside of bacteria and is in a dormant, non-reproductive and enzymatically inert form of a bacterial vegetative cell.

Fluorescence reporter plasmid system: A plasmid-based system comprising one or more reporter genes which fluoresce different colors based on the state of the organism that hosts the plasmid.

Germinate: Refers to the process whereby a bacterial spore becomes a vegetative cell.

Gram-positive: Refers to bacteria that stain purple during a Gram stain procedure. Generally, gram-positive bacteria differ in their structure and/or arrangement of cellular membrane and cell wall as compared to gram-negative bacteria. Specifically, a Gram-positive organism in a cell state contains one thick layer of peptidoglycan which surrounds one cellular membrane.

Metabolically active vegetative state: An active state in the life cycle of endospore-producing bacteria where they are growing and dividing through binary fission.

Recipient strain: Is herein the same as a "target strain" and refers to the bacterial species or sub-species that will accept and maintain the genetic elements on the plasmid of the invention.

Reporter: Refers herein to a reporter gene which e.g. encodes a fluorescent protein. One or more reporter genes may be introduced into in a plasmid system; the term "single reporter plasmid system" thus refers to a plasmid system comprising one reporter gene, "dual reporter plasmid system" refers to a plasmid system comprising two reporter genes, etc.

Vegetative cells: Refers to bacterial cells that are metabolically active and/or actively growing/dividing. Vegetative bacterial cells are not spore cells.

Method for visualizing the state of a strain: The term refers to a method for showing the state in the life cycle of an endospore-producing bacterial strain where the state may e.g. be a dormant endospore state, a metabolically active vegetative state and/or the germinating state of the bacterial strain. In one aspect, the method is for visualizing germination of a strain.

DETAILED DESCRIPTION OF THE INVENTION

With the present invention, the inventors have developed an advantageous plasmid system that is suitable for visualizing the state of *Bacillus* strains such as germination of *Bacillus* strains. The plasmid system of the invention enables *Bacillus* strains to fluoresce depending on the cellular state of the strains. In one aspect of the invention, the plasmid system is used to visualize the *Bacillus* strain in its dormant endospore state. In one aspect of the invention, the plasmid system is used to visualize the *Bacillus* strain in its metabolically active vegetative state. In one aspect of the invention, the plasmid system is used to visualize the *Bacillus* strain in its dormant endospore state and its metabolically active vegetative state. In one aspect of the invention, the plasmid system is used to visualize the transition of *Bacillus* strains from a dormant endospore state to a metabolically active vegetative state.

The plasmid system may be used intra-chromosomally or extra-chromosomally. It has been found that the plasmid system is surprisingly stable when used extra-chromosomally. The inventors have identified several further advantages over the traditional intra-chromosomal method of genetic modification. For example, the plasmid system does not have to be custom made for the recipient strain, and the genome sequence does not need to be known if the recipient organism can maintain a *Bacillus* origin of replication and use sigma factors that are present in *Bacillus*. It is faster to change the phenotype in the strain compared to intra-chromosomal genetic modification because no integration step is required after transformation and consequently additional selection and screening steps are not needed. The copy number of the plasmid of the invention is higher than one which results in the expression of fluorescence genes which have the potential to be greater than a single copy of the gene on the chromosome. The plasmid can be cured out of the strain if there is a need for removing the plasmid. For example, the removal of antibiotic selection and repeated sub-culturing for many generations, a simple task in the lab, can restore the wildtype genotype and phenotype.

The plasmid system is in one aspect of the invention designed to function extra-chromosomally. In a further aspect, the plasmid system is not custom made for the recipient strain. In a yet further aspect, the genome sequence is not known provided that the recipient organism can maintain a *Bacillus* origin of replication and use sigma factors that are present in *Bacillus*. The plasmid systems of the present invention can be maintained in most *Bacillus* strains after transformation. The plasmid system may be used for analyzing e.g. gastrointestinal or plant seed samples. In one aspect, the plasmid system is used on gastrointestinal samples such as gastrointestinal samples from animals. In another or further aspect, the plasmid system is used on plant seed samples.

Plasmid System

With the present invention, a fluorescence reporter plasmid system for enabling a *Bacillus* strain to fluoresce is provided, wherein the *Bacillus* strain fluoresces in its dormant endospore state and/or in its metabolically active vegetative state.

The level of control of a plasmid system of the invention depends on the promoter structure upstream of the fluorescent marker genes. For example, a plasmid system of the invention may comprise a fluorescent protein gene that is fused to a spore-specific gene resulting in fluorescence in the dormant endospore state and/or another fluorescent protein gene which is expressed from a promoter region with strong expression during vegetative cell growth resulting in fluorescence in the metabolically active vegetative state.

In one aspect of the invention, the fluorescence reporter plasmid system enables a *Bacillus* strain to fluoresce after the plasmid has been transformed into the *Bacillus* cell, wherein the *Bacillus* strain fluoresces in its dormant endospore state and/or in its metabolically active vegetative state. In one aspect, the *Bacillus* strain fluoresces with one fluorescent colour when the strain is in dormant endospore state and another fluorescent colour when the strain is in metabolically active vegetative state. In one aspect of the invention, the *Bacillus* strain fluoresces with two different fluorescent colours selected from the group consisting of: Green, red, yellow, cyan, blue, far red and orange.

The plasmid system is in one aspect of the invention designed to function extra-chromosomally.

The backbone of the plasmid system may be derived from any suitable backbone known to the person skilled in the art.

The backbone of the plasmid system of the invention may comprise any suitable components known to the person skilled in the art including, without limitation, one or more vectors, such as e.g. plasmids, one or more origins of replication (ori), one or more origins of transfer (oriT), one or more antibiotic resistance markers, one or more promoter regions, one or more reporter genes and one or more multiple cloning sites. In one aspect of the invention, the plasmid system comprises an origin of replication, a selectable marker using erythromycin resistance, an origin of transfer, and two marker genes (GFP and dsRed) that are under control of specific promoters that are dependent on the transcriptional events within the host cell.

In one aspect of the invention, the backbone of the plasmid system comprises an origin of replication that functions in *Bacillus* strains. In one aspect of the invention, the backbone of the plasmid system comprises an origin of transfer. In one aspect of the invention, the backbone of the plasmid system comprises an antibiotic resistance cassette. In another or further aspect of the invention, the plasmid system is derived from a backbone which comprises an origin of replication and optionally an antibiotic resistance marker. In a further aspect of the invention, the plasmid system is derived from a backbone which comprises an origin of replication and an antibiotic resistance marker. Multiple origins of replication and/or antibiotic resistance markers known to the person skilled in the art may be used in order to host the plasmid in a variety of organisms during the cloning process. In a further aspect of the invention, the backbone of the plasmid is derived from pBM317 (SEQ ID No: 1) or pBG2 (SEQ ID No: 2).

In one aspect of the invention, the plasmid system comprises one or more plasmids selected from the group consisting of: pE194, pUC, pBAD and any combinations thereof. In a further aspect of the invention, the plasmid system comprises an origin of transfer (oriT). In a yet further aspect, the oriT is derived from pUB110.

The plasmid system may be transformed through any suitable means such as without limitations conjugation, natural competence, electroporation or chemical competence. In one aspect, the plasmid system is transformed through conjugation or natural competence.

The plasmid system of the invention comprises one or more reporter genes which encode a fluorescent protein. In one aspect, the plasmid system comprises two or more reporter genes, wherein the reporter genes each encodes a fluorescent protein. In a further aspect, the fluorescent protein(s) encoded by the reporter gene(s) is selected from the group consisting of: green fluorescent protein (GFP), yellow fluorescent protein (YFP), red fluorescent protein (RFP), DsRedexpress2, mCherry, mOrange, mPlum yellow fluorescent protein (EYFP), cyan fluorescent protein (ECFP), and Sapphire In a further aspect, the fluorescent protein(s) encoded by the reporter gene(s) is Green Fluorescent Protein (GFP), or a Red Fluorescent Protein (RFP) such the DsRedexpress2 protein or the DsRed protein. In a preferred aspect, the plasmid system comprises a first reporter gene and a second reporter gene. In a further preferred aspect, the plasmid system comprises a first reporter gene which encodes a fluorescent protein and a second reporter gene which encodes a fluorescent protein which is different from the fluorescent protein encoded by the first reporter gene. In a further aspect, the first reporter gene is a gene encoding a Green Fluorescent Protein (GFP), or a gene encoding a Red Fluorescent Protein (RFP) such as a gene encoding the DsRedexpress2 protein or the DsRed protein. In an alternative or yet further aspect, the second reporter gene is a gene encoding a Green Fluorescent Protein (GFP), or a gene encoding a Red Fluorescent Protein (RFP) such as a gene encoding the DsRedexpress2 protein or the DsRed protein. In a preferred aspect, the first reporter gene is a gene encoding a Green Fluorescent Protein (GFP) and the second reporter gene is a gene encoding a Red Fluorescent Protein (RFP) such as a gene encoding the DsRedexpress2 protein or the DsRed protein. In another preferred aspect, the first reporter gene is a gene encoding a Red Fluorescent Protein (RFP) such as a gene encoding the DsRedexpress2 protein or the DsRed protein and the second reporter gene is a gene encoding a Green Fluorescent Protein (GFP). In a yet further aspect, the reporter gene, such as the first reporter gene or the second reporter gene, is expressed in the dormant endospore.

In a preferred aspect of the invention, the reporter gene, such as the first reporter gene is translationally fused to a gene encoding a small acid-soluble protein (SASP), e.g. sspA, sspB, sspC, sspD, sspE, sspF, sspG, sspH, sspI, sspJ, sspK, sspL, sspM, sspN, sspO, or sspP, such as e.g. sspA, sspB or sspE. In a further aspect, the reporter gene, such as the first reporter gene, includes a promoter region and a region encoding a small acid-soluble protein (SASP). The promoter region of the plasmid system may comprise any suitable promoters known to the person skilled in the art. In one aspect of the invention, the promoter region comprises one or more promoters selected from the group consisting of: amyLp, amyQp, and cryp. In one aspect, the promoter region is sspB. The reporter gene may be any suitable gene. In one aspect, the reporter gene, such as the first reporter gene, is selected from the group consisting of: sspA, sspB, sspC, sspD, sspE, sspF, sspG, sspH, sspI, sspJ, sspK, sspL, sspM, sspN, sspO, and sspP. In a further aspect, the reporter gene, such as the first reporter gene, is selected from the group consisting of: sspA, sspB, and sspE. In a yet further aspect, the reporter gene, such as the first reporter gene, is sspB. In a still further aspect, a linker encoding between 1 to 24 amino acids, such as encoding between 6 to 20 amino acids, 8 to 20 amino acids, 8 to 16 amino acids, 9 to 15 amino acids, 10 to 14 amino acids or 11 to 13 amino acids is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In a yet further aspect, a linker encoding about 12 amino acids is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In an alternative aspect, a linker of between 3 to 72 basepairs, such as between 18 to 60 basepairs, 24 to 60 basepairs, 24 to 48 basepairs, 27 to 45 basepairs, 30 to 42 basepairs or 33 to 39 basepairs is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In a further alternative aspect, a linker of about 36 basepairs is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In one aspect of the invention, the plasmid system can be transformed through conjugation, natural competence, electroporation or chemical competence. In a further aspect of the invention, the plasmid system can be transformed through conjugation or natural competence. In one aspect of the invention, the promoter region of the plasmid system comprises one or more promoters that are expressed during vegetative growth.

In one aspect of the invention, the plasmid system is translated into a SASP protein and a fluorescence protein fusion.

In one aspect of the invention, the plasmid system is selected from the group consisting of: pJDH11 (SEQ ID No: 3), pJDH14 (SEQ ID No: 4), pJDH20 (SEQ ID No: 5), pJDH21 (SEQ ID No: 6), pJDH22 (SEQ ID No: 7), pJDH23 (SEQ ID No: 8), pJDH24 (SEQ ID No: 9), pJDH25 (SEQ ID No: 10), pJDH26 (SEQ ID No: 11), pJDH29 (SEQ ID No: 12) and pBG3 (SEQ ID No: 13).

The plasmid system may be used for enabling a *Bacillus* strain to fluoresce. In one aspect of the invention, the *Bacillus* strain is any *Bacillus* sp. strain. In another aspect of the invention, the *Bacillus* strain is selected from the group consisting of: *B. megaterium, B. subtilis, B. amyloliquefaciens, B. velezensis, B. pumilus, B. licheniformis, B. simplex, B. psychrosaccharolyticus* and *B. thuringiensis*. In yet another aspect of the invention, the *Bacillus* strain is selected from the group consisting of: *B. megaterium, B. subtilis, B. amyloliquefaciens, B. velezensis, B. pumilus* and *B. licheniformis.*

The plasmid system may be added into a plasmid capable of integration into the chromosome such as pMUTIN through the use of a region of homology that is custom for the final *Bacillus* host.

Method of Visualizing the State of *Bacillus* Strains

The present invention also covers a method of visualizing the state of *Bacillus* strains in vitro or in vivo. In one aspect, the method may be used to visualize germination of *Bacillus* strains. In one aspect, a method is provided for visualizing the state of *Bacillus* strains in an animal, a plant or a plant seed. In a further aspect, a method is provided for visualizing germination of *Bacillus* strains in an animal, a plant or a plant seed. In a yet further aspect, a method is provided for visualizing the state of *Bacillus* strains in an animal. In a still further aspect, a method is provided for visualizing germination of *Bacillus* strains in an animal. In another aspect, a method is provided for visualizing the state of *Bacillus* strains in a plant or a plant seed. In a further aspect, a method is provided for visualizing germination of *Bacillus* strains in a plant or a plant seed.

In one aspect of the invention, the method of visualizing the state of *Bacillus* strains such as germination in an animal, a plant or a plant seed comprises the steps:

a) combining a *Bacillus* strain and a cell comprising a single or dual reporter plasmid system for enabling the *Bacillus* strain to fluoresce one fluorescent colour when in dormant endospore state and/or another fluorescent colour when in metabolically active vegetative state,
b) treating an animal or a plant seed with the *Bacillus* strain of step (a),
c) collecting samples from the treated animal or plant seed of step (b),
d) optionally staining the samples of step (c) with DNA dyes, and e) imaging the stained samples of step (c) or (d) to visualize the germination.

In another aspect of the invention, the method of visualizing the state of *Bacillus* strains such as germination in an animal comprises the steps:

a) combining a *Bacillus* strain and a cell comprising a single or dual reporter plasmid system for enabling the *Bacillus* strain to fluoresce one fluorescent colour when in dormant endospore state and/or another fluorescent colour when in metabolically active vegetative state,
b) feeding the *Bacillus* strain of step (a) to an animal,
c) collecting samples from the duodenum, ileum and/or ceca tissues from the animal and preparing the samples for analysis,
d) optionally staining the samples of step (c) with DNA dyes, and
e) imaging the stained samples of step (c) or (d) to visualize the germination.

In yet another aspect of the invention, the method of visualizing the state of *Bacillus* strains such as germination in a plant or a plant seed comprises the steps:

a) combining a *Bacillus* strain and a cell comprising a single or dual reporter plasmid system for enabling the *Bacillus* strain to fluoresce one fluorescent colour when in dormant endospore state and another fluorescent colour when in metabolically active vegetative state,
b) treating a plant seed with the *Bacillus* strain of step (a),
c) optionally planting the treated plant seed of step (b) to grow a plant,
d) collecting samples for analysis by washing the treated plant seed from step (b) which has been allowed to germinate, or the plant of step (c) or a fraction thereof,
e) preparing the samples from step (d) for analysis,
f) optionally staining the samples of step (e) with DNA dyes, and
g) imaging the stained samples of step (e) or (f).

In one aspect of the method, the cell of step (a) comprises a single reporter plasmid system for enabling the *Bacillus* strain to fluoresce one fluorescent colour when in dormant endospore state or when in metabolically active vegetative state. In another aspect of the method, the cell of step (a) comprises a dual reporter plasmid system for enabling the *Bacillus* strain to fluoresce one fluorescent colour when in dormant endospore state and another fluorescent colour when in metabolically active vegetative state.

In one aspect of the invention a method of visualizing the state of *Bacillus* strains such as germination of e.g. *Bacillus* spores is covered, wherein the method comprises using a plasmid system for enabling the *Bacillus* strain to fluoresce. In a further aspect, the plasmid system is a fluorescence reporter plasmid system. In a yet further aspect, the *Bacillus* strain fluoresces in its dormant endospore state and/or in its metabolically active vegetative state.

In one aspect of the invention, the plasmid system used in the method enables a *Bacillus* strain to fluoresce after the plasmid has been transformed into the *Bacillus* cell, wherein the *Bacillus* strain fluoresces in its dormant endospore state and/or in its metabolically active vegetative state. In one aspect, the *Bacillus* strain fluoresces with one fluorescent colour when the strain is in dormant endospore state and another fluorescent colour when the strain is in metabolically active vegetative state. In one aspect of the invention, the *Bacillus* strain fluoresces with two different fluorescent colours selected from the group consisting of: Green, red, yellow, cyan, blue, far red and orange.

The plasmid system used in the method is in one aspect of the invention designed to function extra-chromosomally.

The backbone of the plasmid system used in the method may be derived from any suitable backbone known to the person skilled in the art.

The backbone of the plasmid system used in the method may comprise any suitable components known to the person skilled in the art including, without limitation, one or more vectors, such as e.g. plasmids, one or more origins of replication (ori), one or more origins of transfer (oriT), one or more antibiotic resistance markers, one or more promoter regions, one or more reporter genes and one or more multiple cloning sites. In one aspect of the invention, the plasmid system used in the method comprises an origin of replication, a selectable marker using erythromycin resistance, an origin of transfer, and two marker genes (GFP and dsRed) that are under control of specific promoters that are dependent on the transcriptional events within the host cell.

In one aspect of the invention, the backbone of the plasmid system used in the method comprises an origin of replication that functions in *Bacillus* strains. In one aspect of the invention, the backbone of the plasmid system used in the method comprises an origin of transfer. In one aspect of the invention, the backbone of the plasmid system used in the method comprises an antibiotic resistance cassette. In another or further aspect of the invention, the plasmid system is derived from a backbone which comprises an origin of replication and optionally an antibiotic resistance marker. In a further aspect of the invention, the plasmid system is derived from a backbone which comprises an origin of replication and an antibiotic resistance marker. Multiple origins of replication and/or antibiotic resistance markers known to the person skilled in the art may be used in order to host the plasmid in a variety of organisms during the cloning process. In a further aspect of the invention, the backbone of the plasmid is derived from pBM317 (SEQ ID No: 1) or pBG2 (SEQ ID No: 2).

In one aspect of the invention, the plasmid system used in the method comprises one or more plasmids selected from the group consisting of: pE194, pUC, pBAD and any combinations thereof. In a further aspect of the invention, the plasmid system used in the method comprises an origin of transfer (oriT). In a yet further aspect, the oriT is derived from pUB110.

The plasmid system used in the method may be transformed through any suitable means such as without limitations conjugation, natural competence, electroporation or chemical competence. In one aspect, the plasmid system used in the method is transformed through conjugation or natural competence.

The plasmid system used in the method comprises one or more reporter genes which encode a fluorescent protein. In one aspect, the plasmid system used in the method comprises two or more reporter genes, wherein the reporter genes each encode a fluorescent protein. In a further aspect, the fluorescent protein(s) encoded by the reporter gene(s) is selected from the group consisting of: green fluorescent protein (GFP), yellow fluorescent protein (YFP), red fluorescent protein (RFP), DsRedexpress2, mCherry, mOrange, mPlum yellow fluorescent protein (EYFP), cyan fluorescent protein (ECFP), and Sapphire In a further aspect, the fluorescent protein(s) encoded by the reporter gene(s) is Green Fluorescent Protein (GFP), or a Red Fluorescent Protein (RFP) such the DsRedexpress2 protein or the DsRed protein. In a preferred aspect, the plasmid system used in the method comprises a first reporter gene and a second reporter gene. In a further preferred aspect, the plasmid system used in the method comprises a first reporter gene which encodes a fluorescent protein and a second reporter gene which encodes a fluorescent protein which is different from the fluorescent protein encoded by the first reporter gene. In a further aspect, the first reporter gene is a gene encoding a Green Fluorescent Protein (GFP), or a gene encoding a Red Fluorescent Protein (RFP) such as a gene encoding the DsRedexpress2 protein or the DsRed protein. In an alternative or yet further aspect, the second reporter gene is a gene encoding a Green Fluorescent Protein (GFP), or a gene encoding a Red Fluorescent Protein (RFP) such as a gene encoding the DsRedexpress2 protein or the DsRed protein. In a preferred aspect, the first reporter gene is a gene encoding a Green Fluorescent Protein (GFP) and the second reporter gene is a gene encoding a Red Fluorescent Protein (RFP) such as a gene encoding the DsRedexpress2 protein or the DsRed protein. In another preferred aspect, the first reporter gene is a gene encoding a Red Fluorescent Protein (RFP) such as a gene encoding the DsRedexpress2 protein or the DsRed protein and the second reporter gene is a gene encoding a Green Fluorescent Protein (GFP). In a yet further aspect, the reporter gene, such as the first reporter gene or the second reporter gene, is expressed in the dormant endospore.

In a preferred aspect of the invention, the reporter gene, such as the first reporter gene, used in the method is translationally fused to a gene encoding a small acid-soluble protein (SASP), e.g. sspA, sspB, sspC, sspD, sspE, sspF, sspG, sspH, sspI, sspJ, sspK, sspL, sspM, sspN, sspO, or sspP, such as e.g. sspA, sspB or sspE. In a further aspect, the reporter gene, such as the first reporter gene, includes a promoter region and a region encoding a small acid-soluble protein (SASP). The promoter region of the plasmid system used in the method may comprise any suitable promoters known to the person skilled in the art. In one aspect of the invention, the promoter region comprises one or more promoters selected from the group consisting of: amyLp, amyQp, and cryp. In one aspect, the promoter region is sspB. The reporter gene may be any suitable gene. In one aspect, the reporter gene, such as the first reporter gene, is selected from the group consisting of: sspA, sspB, sspC, sspD, sspE, sspF, sspG, sspH, sspI, sspJ, sspK, sspL, sspM, sspN, sspO, and sspP. In a further aspect, the reporter gene, such as the first reporter gene, is selected from the group consisting of: sspA, sspB, and sspE. In a yet further aspect, the reporter gene, such as the first reporter gene, is sspB. In a still further aspect, a linker encoding between 1 to 24 amino acids, such as encoding between 6 to 20 amino acids, 8 to 20 amino acids, 8 to 16 amino acids, 9 to 15 amino acids, 10 to 14 amino acids or 11 to 13 amino acids is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In a yet further aspect, a linker encoding about 12 amino acids is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In an alternative aspect, a linker of between 3 to 72 basepairs, such as between 18 to 60 basepairs, 24 to 60 basepairs, 24 to 48 basepairs, 27 to 45 basepairs, 30 to 42 basepairs or 33 to 39 basepairs is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE. In a further alternative aspect, a linker of about 36 basepairs is placed between the reporter gene, such as the first reporter gene, and the gene encoding a SASP, e.g. sspA, sspB, sspC, sspD, sspE, sspF, sspG, sspH, sspI, sspJ, sspK, sspL, sspM, sspN, sspO, or sspP, such as e.g. sspA, sspB or sspE.

In one aspect of the invention, the plasmid system used in the method can be transformed through conjugation, natural competence, electroporation or chemical competence. In a further aspect of the invention, the plasmid system can be transformed through conjugation or natural competence. In one aspect of the invention, the promoter region of the plasmid system used in the method comprises one or more promoters that are expressed during vegetative growth.

In one aspect of the invention, the plasmid system used in the method is translated into a SASP protein and a fluorescence protein fusion.

In one aspect of the invention, the plasmid system used in the method is selected from the group consisting of: pJDH11 (SEQ ID No: 3), pJDH14 (SEQ ID No: 4), pJDH20 (SEQ ID No: 5), pJDH21 (SEQ ID No: 6), pJDH22 (SEQ ID No: 7), pJDH23 (SEQ ID No: 8), pJDH24 (SEQ ID No: 9), pJDH25 (SEQ ID No: 10), pJDH26 (SEQ ID No: 11), pJDH29 (SEQ ID No: 12) and pBG3 (SEQ ID No: 13).

The method of visualizing the state of *Bacillus* strains, such as germination, in vitro or in vivo may be used to visualize gemination of any *Bacillus* sp. strain. In one aspect of the invention, the *Bacillus* strain is selected from the group consisting of: *B. megaterium, B. subtilis, B. amyloliquefaciens, B. velezensis, B. pumilus, B. licheniformis, B. simplex, B. psychrosaccharolyticus* and *B. thuringiensis*. In another aspect of the invention, the *Bacillus* strain is selected from the group consisting of: *B. megaterium, B. subtilis, B. amyloliquefaciens, B. velezensis, B. pumilus* and *B. licheniformis.*

The plasmid system used in the method may be added into a plasmid capable of integration into the chromosome such as pMUTIN through the use of a region of homology that is custom for the final *Bacillus* host.

PREFERRED EMBODIMENTS

The following is a list of preferred embodiments of the invention:

1. A fluorescence reporter plasmid system for enabling a *Bacillus* strain to fluoresce, wherein the *Bacillus* strain fluoresces in its dormant endospore state and/or in its metabolically active vegetative state, and wherein the plasmid system is designed to function extra-chromosomally.

2. The plasmid system according to embodiment 1, which enables a *Bacillus* strain to fluoresce after the plasmid has been transformed into the *Bacillus* cell, wherein the *Bacillus* strain fluoresces in its dormant endospore state and/or in its metabolically active vegetative state.

3. The plasmid system according to any one of embodiments 1 to 2, wherein the *Bacillus* strain fluoresces a first fluorescent colour when in its dormant endospore state and a second fluorescent colour when in its metabolically active vegetative state, and wherein the first fluorescent colour differs from the second fluorescent colour.

4. The plasmid system according to any one of embodiments 1 to 3, wherein the fluorescent colour(s) are selected from the group consisting of: Green, red, yellow, cyan, blue, far red and orange.

5. The plasmid system according to any one of embodiments 1 to 4, wherein the backbone comprises an origin of replication that functions in *Bacillus* strains.

6. The plasmid system according to embodiment 5, wherein the backbone further comprises an antibiotic resistance marker.

7. The plasmid system according to any one of embodiments 1 to 6, wherein the backbone comprises an origin of transfer.

8. The plasmid system according to any one of embodiments 1 to 7, wherein the backbone comprises an antibiotic resistance cassette.

9. The plasmid system according to any one of embodiments 1 to 8, which comprises one or more reporter genes which encode a fluorescent protein.

10. The plasmid system according to embodiment 9, wherein the fluorescent protein encoded by the reporter gene is selected from the group consisting of: green fluorescent protein (GFP), yellow fluorescent protein (YFP), red fluorescent protein (RFP), DsRedexpress2, mCherry, mOrange, mPlum yellow fluorescent protein (EYFP), cyan fluorescent protein (ECFP), and Sapphire.

11. The plasmid system according to any one of embodiments 1 to 10, wherein the reporter gene is a gene encoding a Green Fluorescent Protein (GFP), or a gene encoding a Red Fluorescent Protein (RFP) such as a gene encoding the DsRedexpress2 protein or the DsRed protein.

12. The plasmid system according to any one of embodiments 1 to 11, wherein the reporter gene is expressed in the dormant endospore.

13. The plasmid system according to any one of embodiments 1 to 12, wherein the reporter gene is translationally fused to a gene encoding a small acid-soluble protein (SASP).

14. The plasmid system according to any one of embodiments 1 to 13, wherein the reporter gene includes a promoter region and a region encoding a small acid-soluble protein (SASP).

15. The plasmid system according to embodiment 14, wherein the promoter region is sspB.

16. The plasmid system according to any one of embodiments 1 to 15, wherein the reporter gene is selected from the group consisting of: sspA, sspB, and sspE.

17. The plasmid system according to any one of embodiments 1 to 16, wherein the reporter gene is sspB having SEQ ID No: 14.

18. The plasmid system according to any one of embodiments 1 to 17, wherein a linker encoding between 1 to 24 amino acids, such as encoding between 6 to 20 amino acids, 8 to 20 amino acids, 8 to 16 amino acids, 9 to 15 amino acids, 10 to 14 amino acids or 11 to 13 amino acids is placed between the first reporter gene and the gene encoding a SASP.

19. The plasmid system according to any one of embodiments 1 to 18, wherein a linker encoding about 12 amino acids is placed between the first reporter gene and the gene encoding a SASP.

20. The plasmid system according to any one of embodiments 1 to 19, wherein a linker of between 3 to 72 basepairs, such as between 18 to 60 basepairs, 24 to 60 basepairs, 24 to 48 basepairs, 27 to 45 basepairs, 30 to 42 basepairs or 33 to 39 basepairs is placed between the first reporter gene and the gene encoding a SASP.

21. The plasmid system according to any one of embodiments 1 to 20, wherein a linker of about 36 basepairs is placed between the first reporter gene and the gene encoding a SASP.

22. The plasmid system according to any one of embodiments 18 to 21, which is translated into a SASP protein and a fluorescence protein fusion.

23. The plasmid system according to any one of embodiments 1 to 22, wherein the reporter gene is a first reporter gene and the plasmid system further comprises a second reporter gene, wherein the second reporter gene encodes a fluorescent protein which is different from the fluorescent protein encoded by the first reporter gene.

24. The plasmid system according to embodiment 23, wherein the first reporter gene encodes a fluorescent protein which is designed to fluoresce in its dormant endospore state and the second reporter gene encodes a fluorescent protein which is designed to fluoresce in its metabolically active vegetative state.

25. The plasmid system according to embodiment 23 or 24, wherein the fluorescent protein encoded by the second reporter gene is selected from the group consisting of: green fluorescent protein (GFP), yellow fluorescent protein (YFP), red fluorescent protein (RFP), DsRedexpress2, mCherry, mOrange, mPlum yellow fluorescent protein (EYFP), cyan fluorescent protein (ECFP), and Sapphire.

26. The plasmid system according to any one of embodiments 1 to 25, wherein the second reporter gene is a gene encoding a Green Fluorescent Protein (GFP), or a gene encoding a Red Fluorescent Protein (RFP) such as a gene encoding the DsRedexpress2 protein or the DsRed protein.

27. The plasmid system according to embodiment 26, wherein the first reporter gene is a gene encoding a Green Fluorescent Protein (GFP) and second reporter gene is a gene encoding a Red Fluorescent Protein (RFP) such as a gene encoding the DsRedexpress2 protein or the DsRed protein.

28. The plasmid system according to embodiment 26, wherein the first reporter gene is a gene encoding a Red Fluorescent Protein (RFP) such as a gene encoding the DsRedexpress2 protein or the DsRed protein and second reporter gene is a gene encoding a Green Fluorescent Protein (GFP).

29. The plasmid system according to any one of embodiments 1 to 28, wherein the backbone of the plasmid is derived from pBM317 (SEQ ID No: 1) or pBG2 (SEQ ID No: 2).

30. The plasmid system according to any one of embodiments 1 to 29, which comprises the vectors pE194, pUC or pBAD, and the origin of transfer (oriT) from pUB110.

31. The plasmid system according to any one of embodiments 1 to 30, which can be transformed through conjugation, natural competence, electroporation or chemical competence.

32. The plasmid system according to any one of embodiments 1 to 31, which can be transformed through conjugation or natural competence.

33. The plasmid system according to any one of embodiments 1 to 32, wherein the promoter region comprises one or more promoters that are expressed during vegetative growth.

34. The plasmid system according to any one of embodiments 1 to 33, wherein the promoter region comprises one or more promoters selected from the group consisting of: amyLp, amyQp, and cryp.

35. The plasmid system according to any one of embodiments 1 to 34, wherein the *Bacillus* strain is selected from the group consisting of: *Bacillus megaterium, Bacillus subtilis, Bacillus amyloliquefaciens, Bacillus velezensis, Bacillus pumilus, Bacillus licheniformis, Bacillus simplex, Bacillus psychrosaccharolyticus* and *Bacillus thuringiensis.*

36. The plasmid system according to any one of embodiments 1 to 35, wherein the plasmid system is not custom made for the recipient strain.

37. The plasmid system according to any one of embodiments 1 to 36, wherein the genome sequence is not known provided that the recipient organism can maintain a *Bacillus* origin of replication and use sigma factors that are present in *Bacillus*.

38. The plasmid systems according to any one of embodiments 1 to 37, which can be maintained in most *Bacillus* strains after transformation.

39. Use of a plasmid system according to any one of embodiments 1 to 38 for analyzing gastrointestinal or plant seed samples.

40. Use of a plasmid system according to any one of embodiments 1 to 38 for analyzing gastrointestinal samples such as gastrointestinal samples from animals.

41. Use of a plasmid system according to any one of embodiments 1 to 38 for analyzing plant samples or plant seed samples.

42. A cell comprising a plasmid system according to any one of embodiments 1 to 38.

43. A cell according to embodiment 37, wherein the plasmid system is stably integrated into the genome of the cell.

44. A method of visualizing the state of *Bacillus* strains in an animal, a plant or a plant seed comprising:

a) combining a *Bacillus* strain and a cell comprising a single or dual reporter plasmid system for enabling the *Bacillus* strain to fluoresce one fluorescent colour when in dormant endospore state and/or another fluorescent colour when in metabolically active vegetative state,
b) treating an animal or a plant seed with the *Bacillus* strain of step (a),
c) collecting samples from the treated animal or plant seed of step (b),
d) optionally staining the samples of step (c) with DNA dyes, and
e) imaging the samples of step (c) or (d) to visualize the the state of the *Bacillus* strain.

45. A method of visualizing the state of *Bacillus* strains in an animal comprises the steps:

a) combining a *Bacillus* strain and a cell comprising a single or dual reporter plasmid system for enabling the *Bacillus* strain to fluoresce one fluorescent colour when in dormant endospore state and/or another fluorescent colour when in metabolically active vegetative state.
b) feeding the *Bacillus* strain of step (a) to an animal,
c) collecting samples from the duodenum, ileum and/or ceca tissues from the animal and preparing the samples for analysis,
d) optionally staining the samples of step (c) with DNA dyes, and
e) imaging the samples of step (c) or (d) to visualize the state of the *Bacillus* strain.

46. A method of visualizing the state of *Bacillus* strains in a plant or a plant seed comprises the steps:

a) combining a *Bacillus* strain and a cell comprising a single or dual reporter plasmid system for enabling the *Bacillus* strain to fluoresce one fluorescent colour when in dormant endospore state and another fluorescent colour when in metabolically active vegetative state
b) treating a plant seed with the *Bacillus* strain of step (a),
c) optionally planting the treated plant seed of step (b) to grow a plant,
d) collecting samples for analysis by washing the treated plant seed from step (b) which has been allowed to germinate, or the plant of step (c) or a fraction thereof,
e) preparing the samples from step (d) for analysis,
f) optionally staining the samples of step (e) with DNA dyes, and
g) imaging the samples of step (e) or (f) to visualize the state of *Bacillus* strains.

47. The method according to any one of embodiments 44 to 46, wherein the cell of step (a) comprises a single reporter plasmid system for enabling the *Bacillus* strain to fluoresce one fluorescent colour when in dormant endospore state or when in metabolically active vegetative state.

48. The method according to any one of embodiments 44 to 47, wherein the cell of step (a) comprises a dual reporter plasmid system for enabling the *Bacillus* strain to fluoresce one fluorescent colour when in dormant endospore state and another fluorescent colour when in metabolically active vegetative state.

49. A method of visualizing the state of *Bacillus* strains in vitro or in vivo, wherein a plasmid system according to any one of embodiments 1 to 38 is used for enabling the *Bacillus* strains to fluoresce in the dormant endospore state and/or the metabolically active vegetative state, wherein the fluorescence of the *Bacillus* strains indicates the state of the strain.

50. The method according to embodiment 49, wherein the *Bacillus* strain fluoresces one fluorescent colour when in the dormant endospore state and another fluorescent colour when in the metabolically active vegetative state.

51. The method according to any one of embodiments 38 to 50, which is used to visualize germination of the *Bacillus* strains.

EXAMPLES

The plasmid system of the invention has herein been used to transform six strains of *B. subtilis*, four strains of *B. amyloliquefaciens*, two strains of *B. megaterium*, two strains of *B. pumilis*, one strain of *B. thuringiensis*, and even one strain of *Bacillus* for which we did not know the species designation as exemplified below.

Example 1—Plasmid Design and Function

The backbone of the plasmid(s) came from pBM317 (SEQ ID No: 1). This backbone was composed of pE194 and pUC plus the oriT from pUB110. Consequently, this vector could be maintained in *E. coli* as well as most *Bacillus* without the need for integration into their chromosome. Furthermore, it could be transformed through a variety of means including conjugation, natural competence, electroporation, and chemical competence. The former two methods have proven the most effective in our work. Our versions of this plasmid that included the green and/or red fluorescence systems were pJDH11 (SEQ ID No: 3), pJDH14 (SEQ ID No: 4), pJDH20 (SEQ ID No: 5), pJDH21 (SEQ ID No: 6), pJDH22 (SEQ ID No: 7), pJDH23 (SEQ ID No: 8), pJDH24 (SEQ ID No: 9), pJDH25 (SEQ ID No: 10), pJDH26 (SEQ ID No: 11), pJDH29 (SEQ ID No: 12) and pBG3 (SEQ ID No: 13).

In most of these constructs the GFP gene was used as a reporter for the presence of spores. The gene was translationally fused to the gene that encodes a small acid-soluble protein (SASP). Specifically, this gene was sspB (SEQ ID No: 14) from *B. amyloliquefaciens*. There was a small region between the SASP and GFP genes that encoded a short linker of amino acids that should generate a small loop between these proteins. The linker ensured that the proteins remained tethered to one another, but that their folding remained largely independent and unaffected by the fusion. This last item was deemed critical, because we require both the domains of this fusion to remain functional. The SASPs bind with high affinity to DNA and are unique to dormant spores. Consequently, our SASP-GFP fusion coats spored DNA in green fluorescence, and our work demonstrated that the fluorescence persisted as long as the spores were stable. Shortly after germination is triggered, a protease called germination protease (Gpr) should rapidly degrade the SASPs. Gpr will also degrade the GFP that was fused to SspB. This enabled a smooth transition from green fluorescent spores to red fluorescent cells during or shortly after spore germination.

In most of these plasmid constructs there was a second reporter gene sequence that encoded the DsRedexpress2 (DsRed) protein. This protein was under the control of multipart promoter in most cases. The entire promoter resulted in very high expression during the vegetative state by any gene immediately downstream. The complete promoter region consisted of one or more of the following: amyLp, amyQp, and cryp. In addition, some constructs used the rplKp from *B. amyloliquefaciens* (O7SKR). Multiple combinations of these promoters were used to fine-tune the expression of DsRed either up or down depending on the needs of the final recipient strain of this plasmid.

Ultimately, we used the plasmid backbone and two genetic circuits described above to create a variety of plasmids that we refer to as "reporter plasmids", because of their propensity to impart fluorescence on their host; this characteristic enabled the transformed cell to report on its cellular and metabolic state. The spore-specific reporter system was activated during sporulation and resulted in dormant and stable spores that uniformly fluoresced green. The green fluorescence, due to the nature of its translational fusion, was rapidly degraded during spore germination, and significantly reduced as the organism became vegetative. During the vegetative state the promoters that drove red fluorescence became very active. Furthermore, we could determine the state of the organisms as either spore or vegetative, and when the latter was true then we could achieve a relative understanding of their level of growth and protein synthesis. One major advantage of these plasmids is that they function extra-chromosomally i.e. they do not require integration into the host chromosome to function. In addition, their origin of replication permits them to be stably maintained in most *Bacillus* sp. So, one plasmid can be quickly transformed and assessed in a new strain within a short time frame.

Example 2—In Vitro Examination of Dual Reporter Strain Operation

In order to ensure that the plasmid functioned as designed, an in vitro analysis was used to observe a strain of *Bacillus subtilis* that carried pJDH20 as illustrated in FIG. 1. This new reporter strain was created from the *Bacillus subtilis* strain deposited as DSM 29870 and described in WO 2016/118864, which is a commercial probiotic for poultry. We used fluorescent microscopy and flow cytometry to track the spore population as it transitioned from dormant spores with green fluorescence (GFP) to vegetative growing cells with red fluorescence (DsRed). This invention could be measured by any instrument that can detect fluorescence in the green and red wavelengths.

Purified spores of wildtype *Bacillus subtilis* strain deposited as DSM 29870 (WT) and fluorescent *Bacillus subtilis* strain deposited as DSM 29870 (Fluor), with the dual reporter plasmid pJDH20 in the latter, were used for this examination. The spores were heat primed for germination and then aliquoted into wells in a clear 96-well plate (Costar 3595) that also contained Miller LB medium (Fisher BP1426) with 5 ug/ml Erythromycin and 25 ug/ml Lincomycin. Each strain was aliquoted to a total of 12 wells to permit destructive testing at defined timepoints and with three replicates. The timepoints were 0, 5, 18, and 24 hours after combining the medium and spores. Immediately after combining the spores and medium the plate was incubated at 35° C. and agitated for the duration of the experiment. A control with no spores was also included in the examination. Samples were removed from the 96-well plate after 0, 5, 18, and 24 h of incubation and assayed using fluorescent microscopy and flow cytometry (BD Accuri C6).

Figure 2:
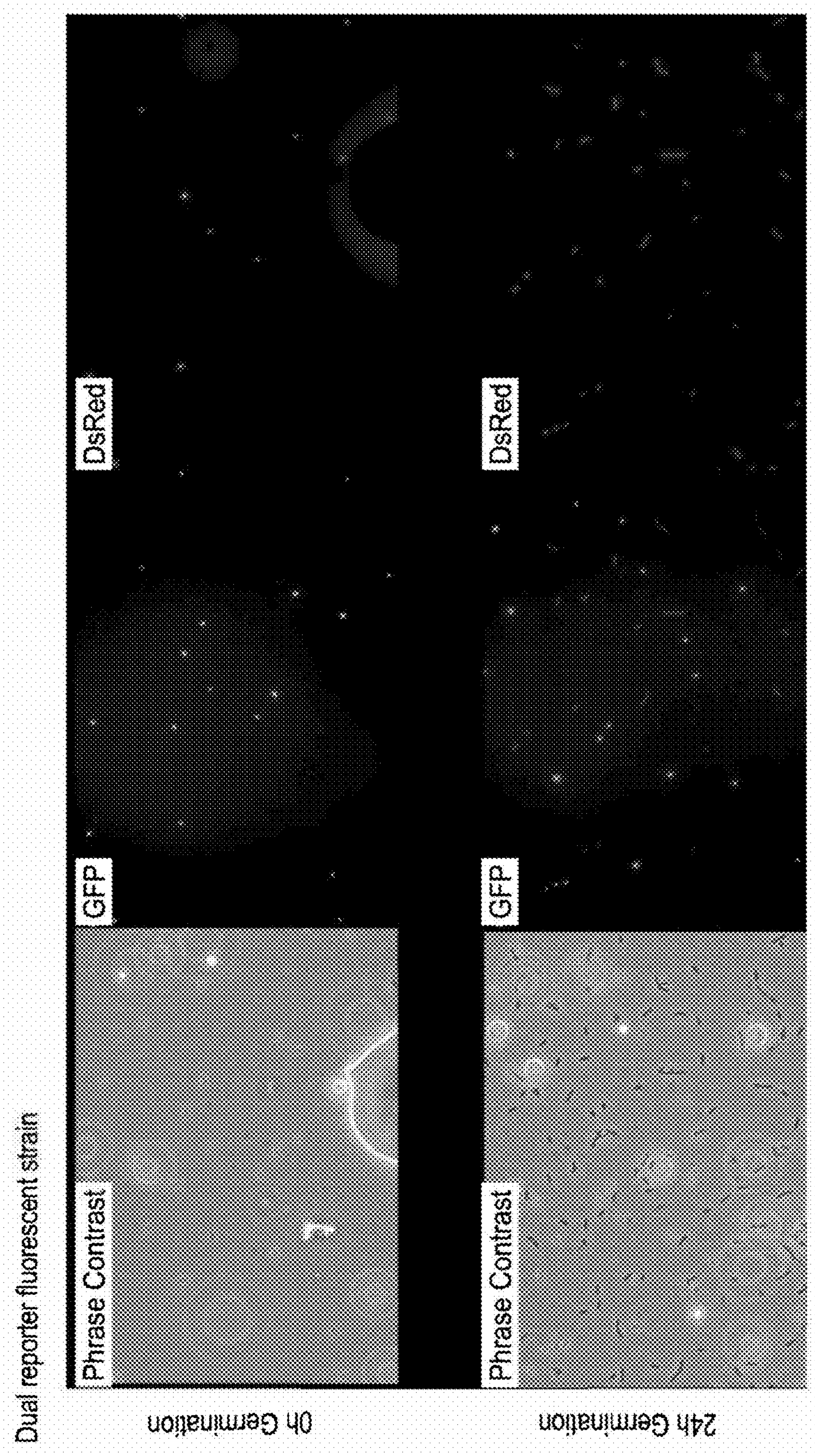
FIG. 2 shows fluorescence microscopy of the dual reporter fluorescent strain of the *Bacillus subtilis* strain deposited as DSM 29870 (described in WO 2016/118864) after incubation in LB medium containing 5 ug/ml Erythromycin and 25 ug/ml Lincomycin. Shown are representative images of samples after 0 h (top row) and 24 h (bottom row). Each sample image was captured using phase contrast (left column), GFP filter (center column), and DsRed filter (right column).
Figure 3:
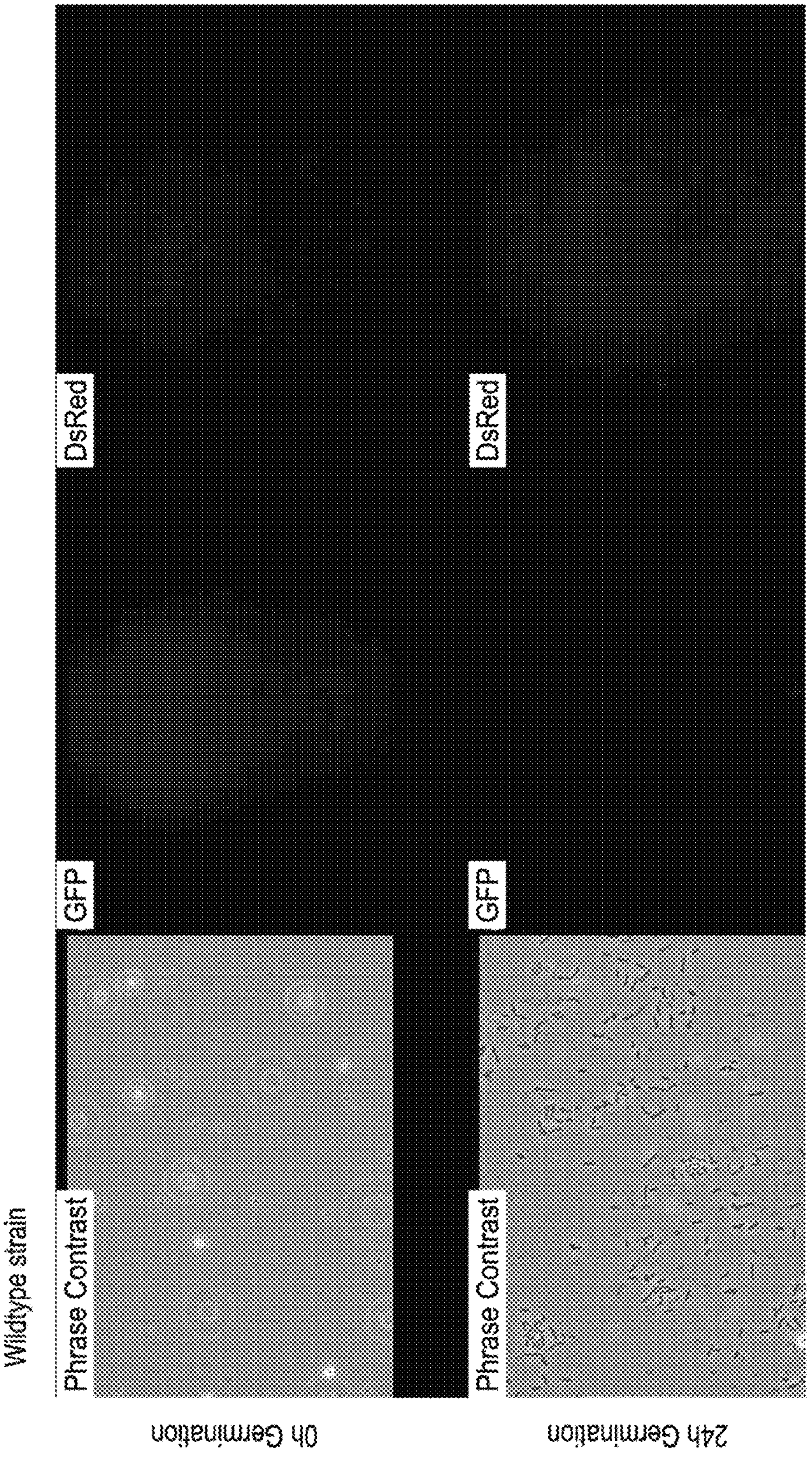
FIG. 3 shows fluorescence microscopy of the wildtype strain of *Bacillus subtilis* strain deposited as DSM 29870 after incubation in LB medium containing 5 ug/ml Erythromycin and 25 ug/ml Lincomycin. Shown are representative images of samples after 0 h (top row) and 24 h (bottom row). Each sample image was captured using phase contrast (left column), GFP filter (center column), and DsRed filter (right column).

In order to observe if both GFP and DsRed were expressed in the Fluor strain we used fluorescence microscopy. Microscopy clearly showed that both the WT and Fluor strains contained phase-bright dormant spores at the beginning of the examination and germinated into vegetative cells during incubation (FIGS. 2 and 3 left column). In addition, the spores and cells of the Fluor strain were fluorescent (FIG. 2). These spores were clearly green (FIG. 2 center column) while the cells were red (FIG. 2 right column). It is common for fluorescence of one color to be detected with other filter sets and that was the case here too, but the most intense green was observed from spores and the most intense red was observed from cells after 24 h incubation. At intermediate time points, outgrowing spores and young cells demonstrated varying levels of both green and red fluorescence (data not shown). WT spores and cells never demonstrated any fluorescence although they were clearly present, germinated, and grew (FIG. 3). A spore-free control contained no spores or cells and generated no fluorescence (data not shown).

Figure 4:
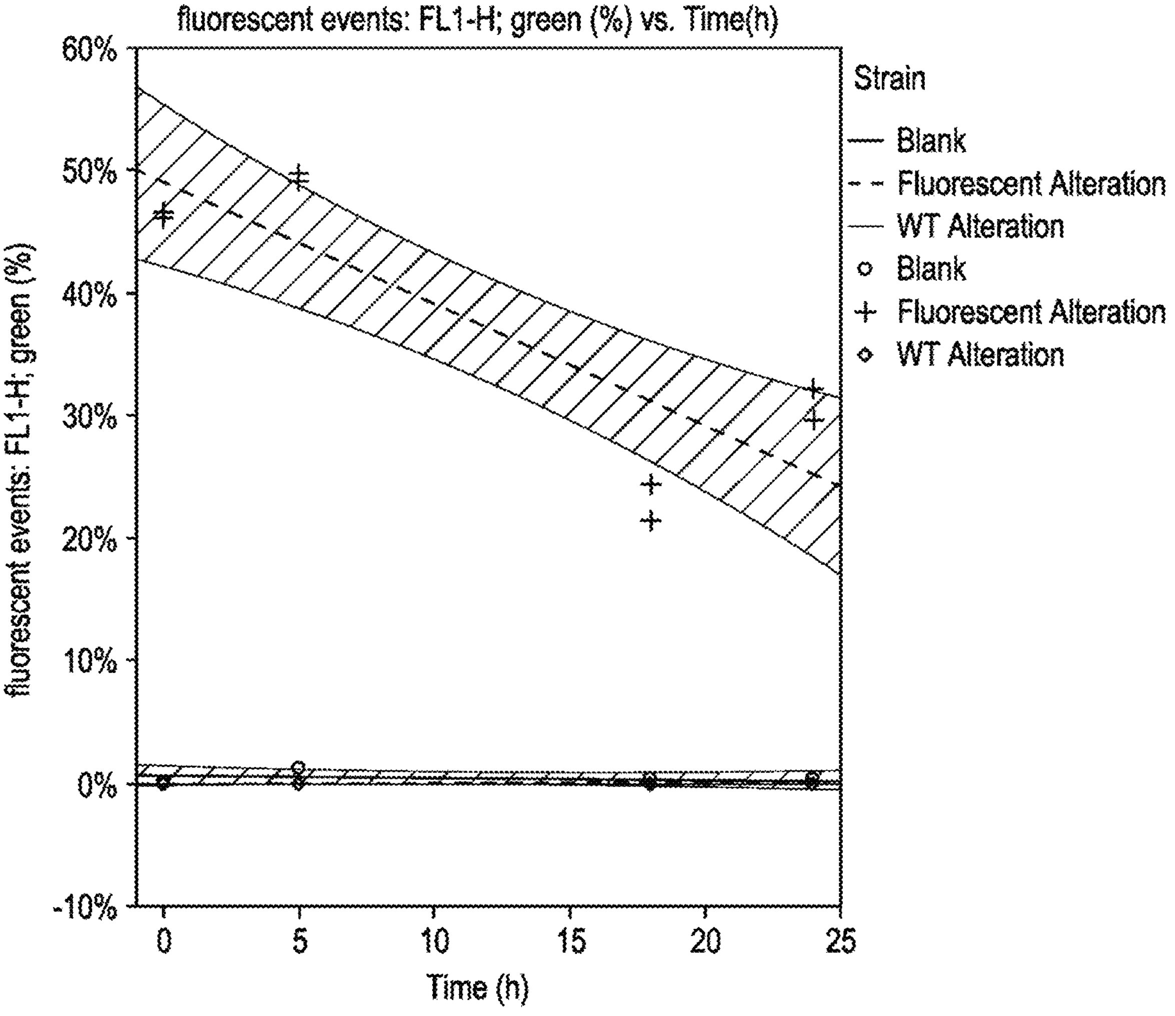
FIG. 4 shows flow cytometry of the percentage of green fluorescent events during germination of wildtype (0) and fluorescent (+) spores of *Bacillus subtilis* strain deposited as DSM 29870 after incubation in LB medium containing 5 ug/ml Erythromycin and 25 ug/ml Lincomycin. A spore-free blank sample (o) is also shown as a negative control. The data shown is the scatter plot of three replicate experiments. A linear regression with shading that indicates 95% confidence intervals is also shown for the blank (solid line), wildtype (dashed line), and fluorescent (dotted line) strains.
Figure 5:
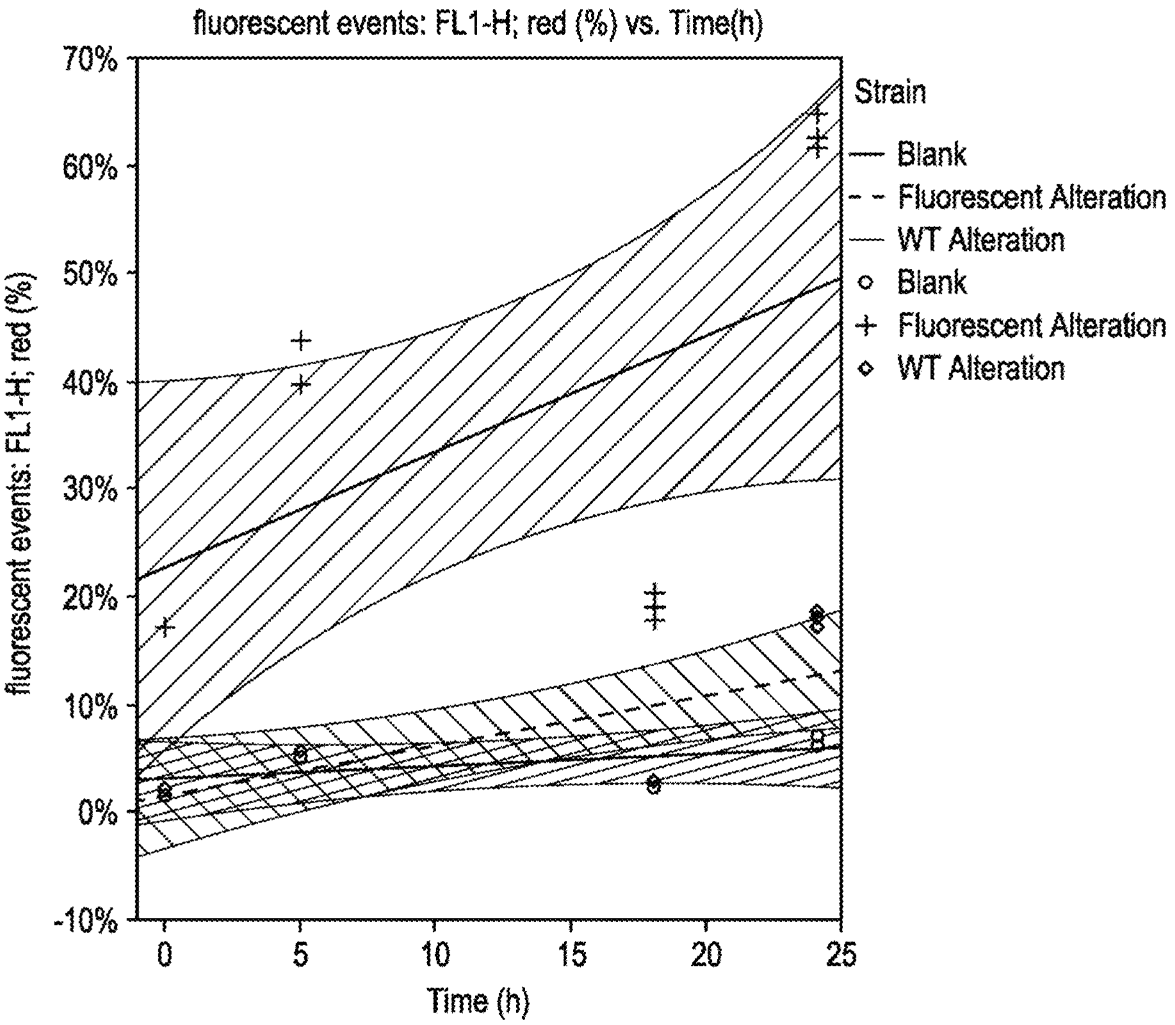
FIG. 5 shows flow cytometery of the percentage of red fluorescent events during germination of wildtype (0) and fluorescent (+) spores of *Bacillus subtilis* strain deposited as DSM 29870 after incubation in LB medium containing 5 ug/ml Erythromycin and 25 ug/ml Lincomycin. A spore-free blank sample (○) is also shown as a negative control. The data shown is the scatter plot of three replicate experiments. A linear regression with shading that indicates 95% confidence intervals is also shown for the blank (solid line), wildtype (dashed line), and fluorescent (dotted line) strains.

Although it is aesthetically pleasing, it can be difficult to accurately determine the intensity of fluorescence from a population of spores or cells using microscopy alone. Thus, we used flow cytometry to quantify the number of spore-related and cell-related events in each sample that fluoresced green or red in the same 96-well plate examination described above. The spore-free blank sample was critical in determining the level of background fluorescence that is due to the medium or other particulates in the assay that are not the *Bacillus subtilis* strain deposited as DSM 29870. The WT spores and cells that later developed as incubation progressed did not generate a significantly higher number of fluorescent green (FIG. 4) or red (FIG. 5) events than the blank sample. The Fluor spores did clearly generate green and red fluorescent events (FIGS. 4 and 5). Furthermore, the percentage of fluorescent events changed as the spores incubated and produced vegetative cells. Green fluorescence was highest in the Fluor strain while the spores were still dormant at 0 h incubation and it steadily decreased as incubation continued and spores germinated into vegetative cells (FIG. 4). Green fluorescence never decreased to the background levels which suggests that dormant spores were still present after 24 h; this is consistent with microscopy results that clearly shows dormant spores in the 24 h samples (FIG. 2). Red fluorescence at 0 h was not significantly higher than the background, but it steadily increased above background at 5 h incubation and continued to increase after 18 and 24 h of incubation (FIG. 5). Red fluorescence detected during flow cytometry was consistent with microscopy that showed no red fluorescent cells at 0 h, and a multitude of red cells at later timepoints that was greatest after 24 h (FIG. 3).

The novel fluorescent characteristics imparted on *Bacillus subtilis* strain deposited as DSM 29870 by pJDH20 were clearly demonstrated in this in vitro experiment. The spores fluoresced green due to the translational fusion of the SASP gene to a GFP gene. As expected, the green fluorescence decreased as the spore population germinated and SASP proteins were degraded by the normal spore outgrowth processes. The resulting vegetative cells developed red fluorescence as time progressed, also as expected, from a DsRed gene that was driven by a constitutive vegetative cell promoter. The plasmid never had to be integrated into the chromosome of the host strain. Ultimately, the fluorescent strain of *Bacillus subtilis* strain deposited as DSM 29870 served as an in vitro indicator of spore dormancy, germination, and vegetative growth using a dual reporter system.

Example 3—Examination of the Gastrointestinal Samples Harvested from Chickens Fed the Dual Reporter Strain A plasmid from Example 1 was transformed into *Bacillus subtilis* thus engineered to express Green fluorescent protein (GFP) during the spore life stage and Red fluorescent protein (RFP) during the vegetative life stage was used to visualize the transition from the spores, which were fed to chickens, to vegetative in gastrointestinal samples.

Figure 6:
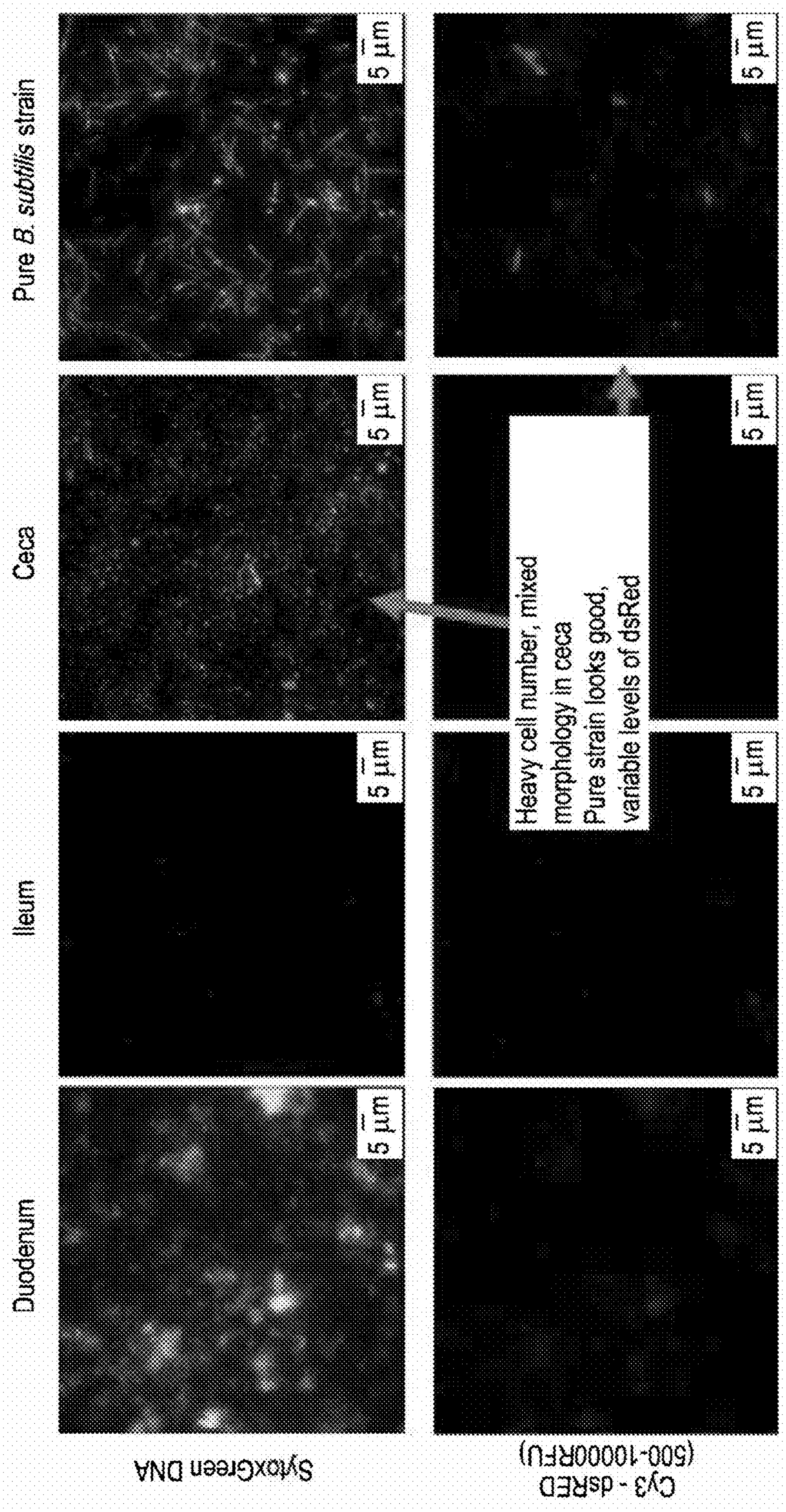
FIG. 6 shows examples of images from gastrointestinal (GI) content samples from example 3. The upper four images show samples from respectively duodenum, ileum, ceca and a pure *B. subtilis* strain culture as reference strain stained with SytoxGreen DNA and the lower four images show samples from respectively duodenum, ileum, ceca and the reference strain stained with Cy3-dsRED. Pure strain cultures demonstrate a heterogeneous RFP-expressing population as compared to total cell DNA staining.

Feed samples treated with *Bacillus subtilis* were fed to chickens, followed by sacrifice and harvesting of duodenum, ileum, and ceca tissues. The content of each tissue was collected in separate tubes and frozen. Tissues were fixed in 10% buffered formalin. Upon sample receipt, GI content samples were processed for visualization by thawing and resuspending the content samples in phosphate buffered saline with 0.01% tween 20 and 0.25% triton-X 100. Major solids were then separated via low speed centrifugation, and supernatant samples were then fixed in buffered formalin for 1 hour. Following fixation, samples were stained with the DNA dyes SytoxGreen and DAPI, followed by a final 25 μm filtration, and then imaged using an INCell 2200 high content imaging system. Three color DAPI/FITC/Cy3 images were collected for each sample at various final dilutions. SytoxGreen DNA staining data collected from the FITC image, DAPI DNA staining from the DAPI channel, RFP data from the Cy3 image. As a control, a pure RFP-expressing *Bacillus subtilis* strain was used (FIG. 6).

Figure 7:
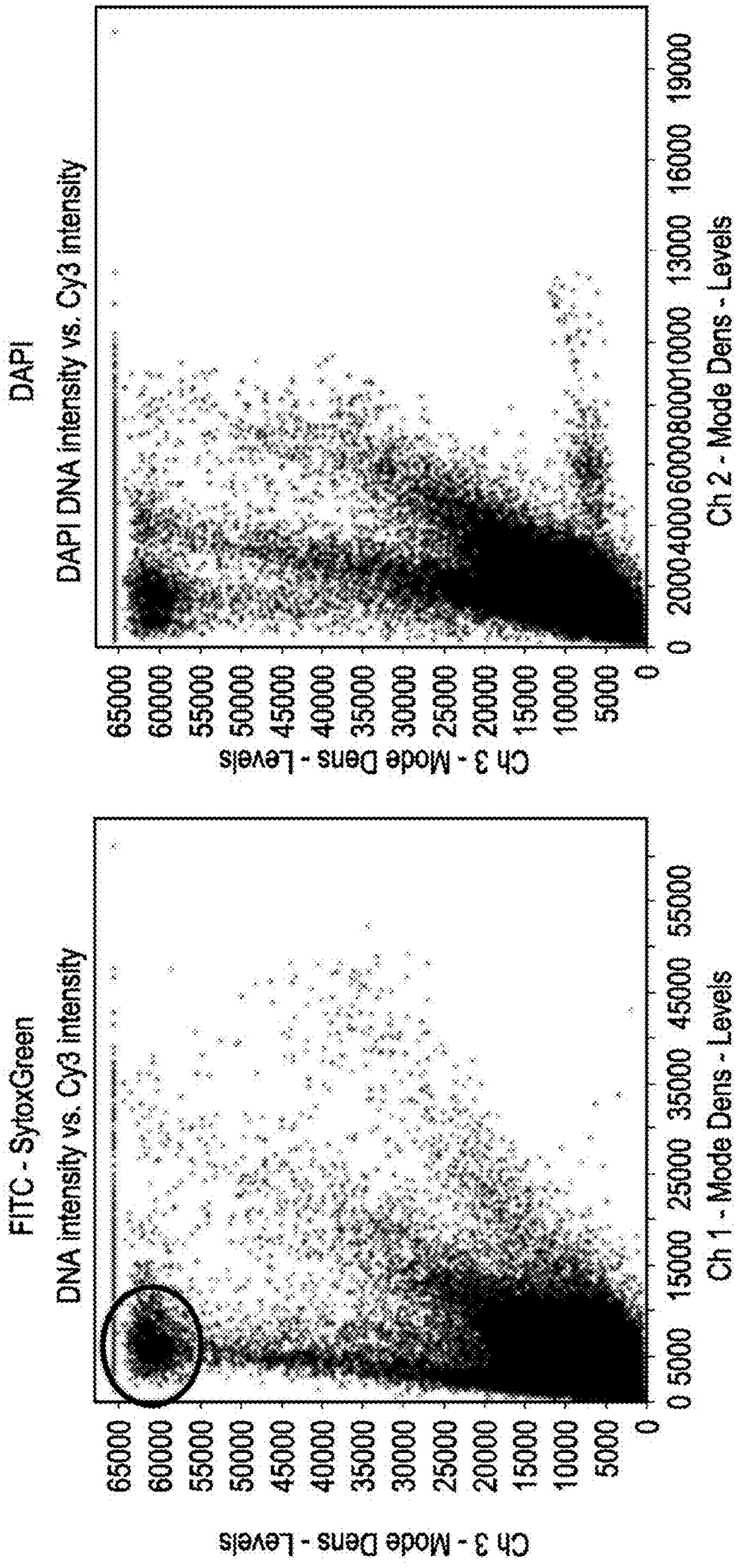
FIG. 7. Following individual object detection from all collected images, Graph showing the entire data set with DNA as the object identifier on the X-axis and RFP intensity measured on the y-axis. All data used for this comparison was from the sample dilution. A cluster of RFP-bright objects was observed.

Following individual object detection from all collected images, the entire data set was graphed using DNA as the object identifier (X-axis) and RFP intensity measured on the y-axis (FIG. 7).

Figure 8:
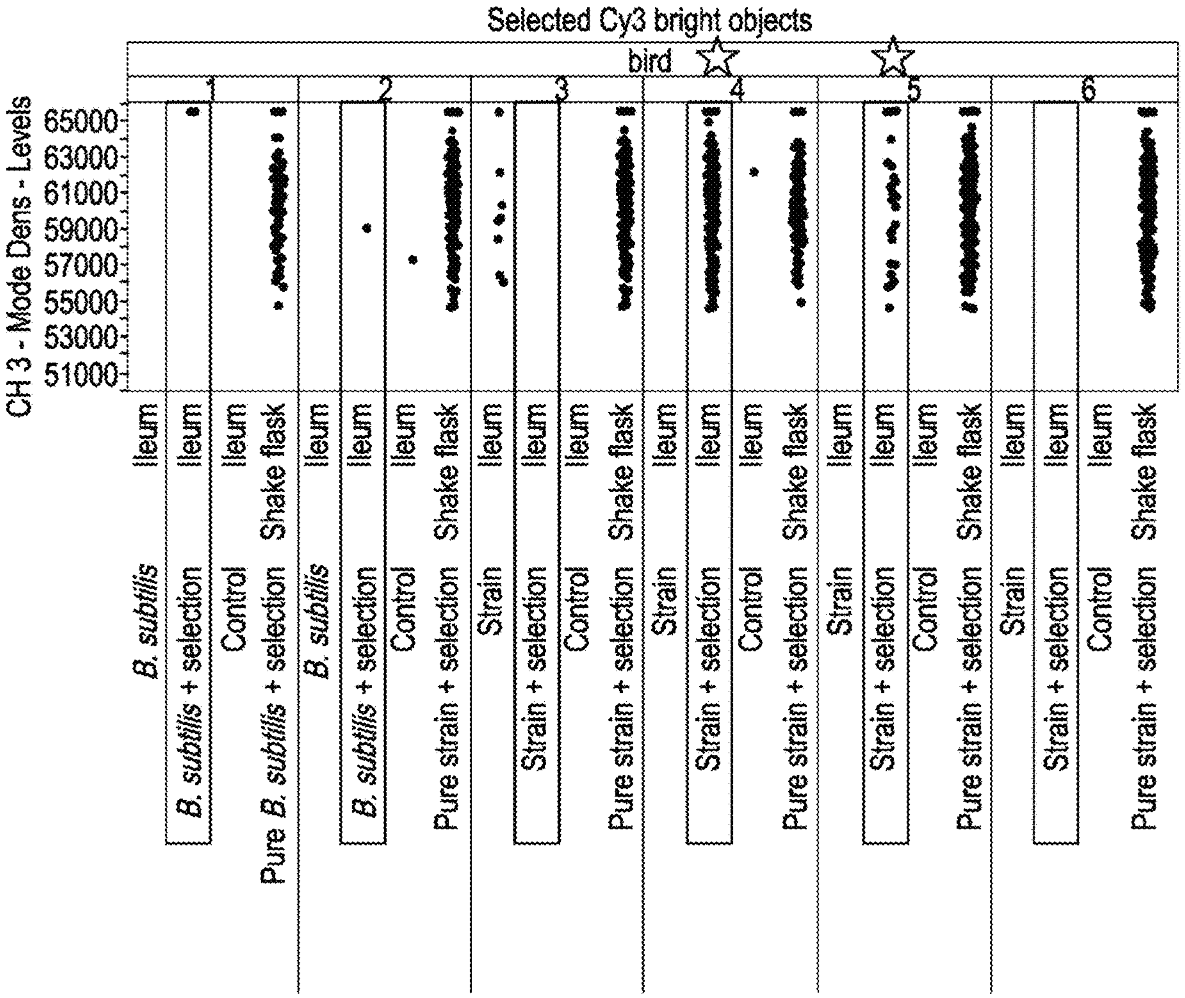
FIG. 8 shows a sub-group of individual objects selected based on high RFP intensity levels. In all wells containing pure RFP-expressing strain samples, a large number of Cy3-bright objects were detected. Also, RFP-bright objects were detected in ileum samples from birds fed the *Bacillus subtilis* RFP-expressing strain, but not from control birds who were fed a different diet.
Figure 9:
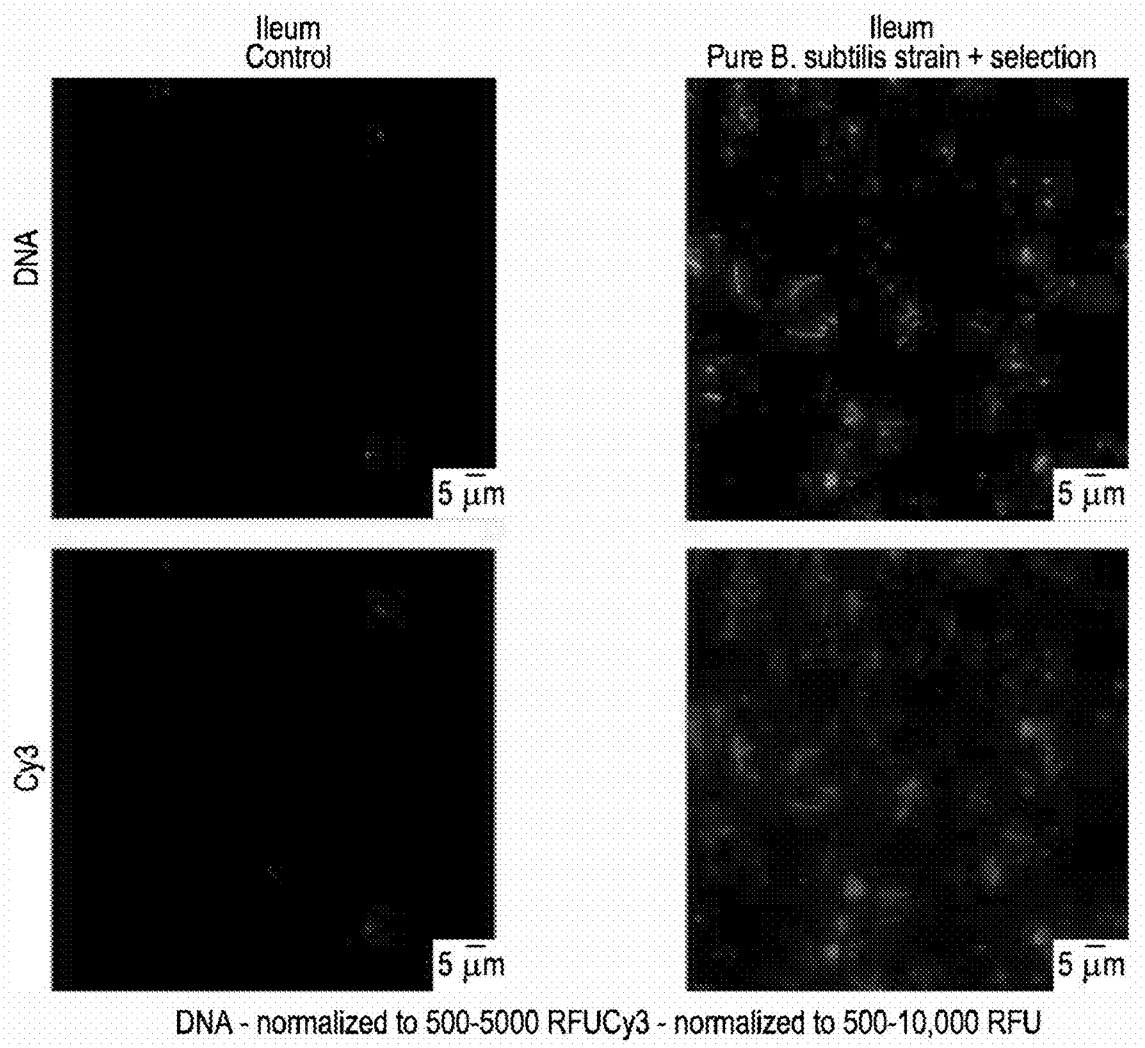
FIG. 9. Example ileum content sample images from bird fed the RFP-expressing *Bacillus subtilis* strain and selection antibiotics as compared to ileum content sample form a control bird.
Figure 10A:
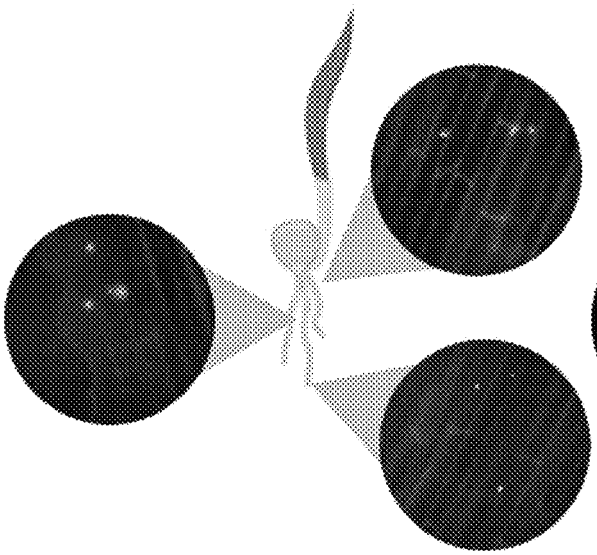
FIG. 10. Fluorescent reporter strains indicate that root colonization of germinating corn seeds by *Bacillus* is strain dependent. Fluorescent microscopy of sections from the top, middle, and bottom (see inset markers) of the radicle 4-5 days after seed germination are shown for *B. megaterium* *O*83AN1 (A), *B. megaterium O*8337C (B), *B. amyloliquefaciens* O44EAY (C), and *B. thuringiensis* O84YVJ (D). Shown are representative images of at least 10 replicate samples per strain and each shows the fluorescence overlay of the section with both green and red filters. Viable bacterial cells fluoresced red (light colored rods in image) and plant cells naturally fluoresced green (light colored rectangular cells in image). All images are 400× magnification.
Figure 10B:
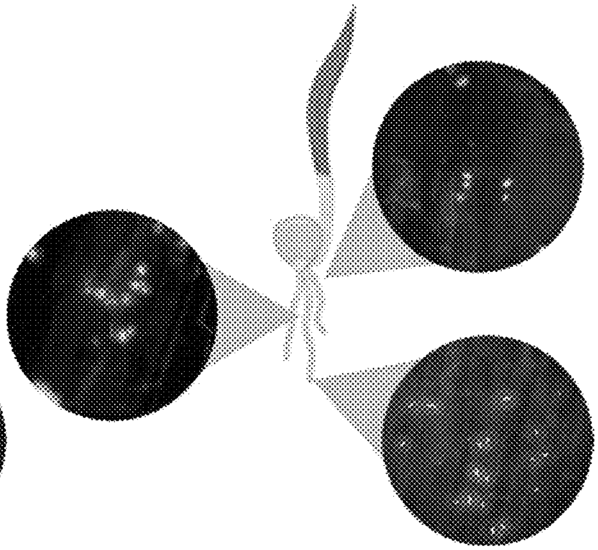
Figure 10C:
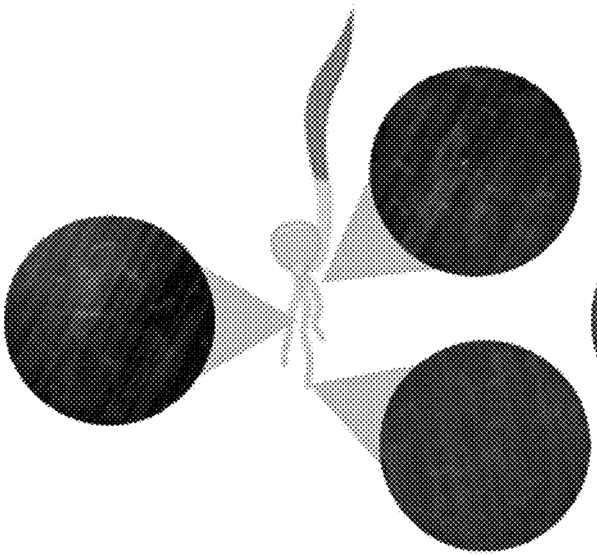
Figure 10D:
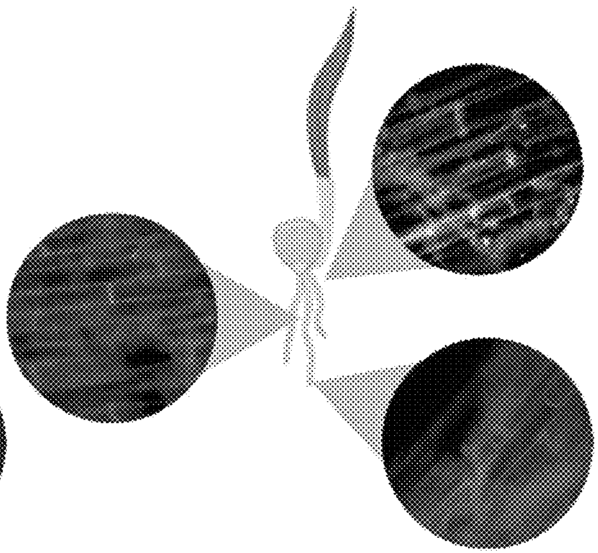

All data used for this comparison was from the sample dilution. A cluster of RFP-bright objects was observed, and that group of object data was separated for further analysis (FIG. 8). In all wells containing pure RFP-expressing strain samples, a large number of Cy3-bright objects were detected. Furthermore, we were also able to detect RFP-bright objects in ileum samples only from birds fed the *Bacillus* sp. RFP-expressing strain, but not from control birds who were fed a different diet (FIG. 9).

Conclusions

Analysis of gastrointestinal (GI) content samples demonstrated *Bacillus subtilis* RFP-expressing cells in ileum from a bird.

Example 4—Examination of Germinated Corn Seed Treated with the Reporter Strain Four strains were transformed with the reporter plasmid described in example 1: *B. amyloliquefaciens* (O44EAY), *B. megaterium* (O83AN1), *B. megaterium* (O8337C), and *B. thuringiensis* (O84YVJ). The fluorescent nature of these organisms revealed that each strain had different colonization behaviors on the roots of germinating corn seed. These results demonstrated that this reporter plasmid can be used to detect the presence of the recipient organism using fluorescence microscopy. Furthermore, the reporter system revealed the relative amount of the organism on the environment, its status as either a cell or spore, and its location along the environment being tested.

Corn seeds (Viking) were treated with liquid suspensions of dormant spores of either O44EAY, O83AN1, 08337C, or O84YVJ. In addition, treatments were also performed using non-fluorescent versions of these strains for use as a control. An individual treatment consisted of 50 seeds being mixed with 100 μL of spores at a concentration of 1e8 cfu/mL for an estimated application rate of 5e5 cfu/mL. After treatment, the seeds were germinated by placing them on germination paper (Anchor Paper Co.), soaked in water and incubated at 22° C. in the dark for 4-5 days. During incubation, the seeds germinated and produced a radicle and the beginnings of a root system. After incubation, the radicle was divided into three sections: the top section was the third of the radicle nearest the crown, the middle was the center third of the radicle, and the bottom was the third of the radicle that included the tip. Using a scalpel, thin sections were made of the top, middle, and bottom sections of each radicle that were suitable for fluorescence microscopy. For each treatment, at least 10 seeds were observed.

Each strain was observed at some region on the corn radicle after the seed germinated (FIG. 10). The fluorescent nature of the organisms was essential in locating them on the sections of root material. The cell walls of the plant tissue were well visualized with the use of a green filter, and the red filter revealed the presence of vegetative cells with strong red fluorescence properties. Control seeds that received no treatment with an organism did not produce root sections with any detectable red fluorescence (data not shown).

These results indicated that the spores can germinate on the seed and/or the root while seed germination is in progress, that in some cases they are able to colonize areas that are significantly distant from the location where they were applied, and that some strains are better suited to germinate and possibly grow on roots than others. Germination on seed was supported, because red cells were present after treatment with dormant spores (FIG. 10). Colonization along the entire root was supported, because even though O83AN1 and O8337C were applied as dormant spores directly to the seed, they were clearly observed on sections near the root tip (FIG. 10 left and center). Strain-specific performance was supported because we consistently observed more fluorescent vegetative cells of O8337C than O83AN1 on root sections, very few cells of O44EAY were ever observed, and many cells of O84YVJ were observed but only at the topmost region of the root. (FIG. 10). Again, these differences occurred even though the dose of spores during seed treatment were the same for all strains. Notably for O44EAY, we never observed cells at the middle and bottom sections of the root. These results suggest that O44EAY is not as good of a candidate for a seed inoculant as O83AN1, 08337C, or O84YVJ, because it struggles either to germinate in this environment or to maintain viability.

The fluorescent reporter system could be inserted into four different strains of *Bacillus* without the need for customized modification of the plasmid, and then generate spores that could be applied to the seed before germination that clearly indicated if the spores germinated, if they were subsequently viable, their location, and their relative abundance on a newly formed corn root.

The invention claimed is:

1. A fluorescence reporter plasmid system for enabling a *Bacillus* strain to fluoresce a first color in its dormant endospore state and a second color different from said first color in its metabolically active vegetative state, said fluorescence reporter plasmid system comprising a backbone derived from SEQ ID NO: 1, a first reporter gene encoding a first fluorescent protein to be expressed when said *Bacillus* strain is in its dormant endospore state, and a second reporter gene encoding a second fluorescent protein to be expressed when said *Bacillus* strain is in its metabolically active vegetative state.

2. The fluorescence reporter plasmid system according to claim 1, wherein the first reporter gene comprises a promoter that is selectively expressed in said *Bacillus* strain's dormant endospore state.

3. The fluorescence reporter plasmid system according to claim 1, wherein the first reporter gene comprises a promoter selected from sspA, sspB, sspC, sspD, sspE, sspF, sspG, sspH, sspI, sspJ, sspK, sspL, sspM, sspN, sspO and sspP promoter.

4. The fluorescence reporter plasmid system according to claim 1, wherein the first reporter gene is translationally fused to a gene encoding a small acid-soluble protein.

5. The fluorescence reporter plasmid system according to claim 4, wherein the first fluorescent protein is selected from green fluorescent protein (GFP), yellow fluorescent protein (YFP), red fluorescent protein (RFP), DsRedexpress2, mCherry, mOrange, mPlum yellow fluorescent protein (EYFP), cyan fluorescent protein (ECFP), and Sapphire.

6. The fluorescence reporter plasmid system according to claim 1, wherein the second reporter gene comprises a promoter that is selectively expressed in said *Bacillus* strain's metabolically active vegetative state.

7. The fluorescence reporter plasmid system according to claim 1, wherein the second reporter gene comprises a two or more promoters that are selectively expressed in said *Bacillus* strain's metabolically active vegetative state.

8. The fluorescence reporter plasmid system according to claim 1, wherein the second reporter gene comprises one or more promoters selected from amyLp, amyQp, cryp and rplKp promoters.

9. The fluorescence reporter plasmid system according to claim 1, wherein the first reporter gene is joined by a linker encoding 1 to 24 amino acids to a gene encoding a small acid-soluble protein, whereby a fusion protein comprising the first fluorescent protein linked to the small acid-soluble protein is produced in said *Bacillus* strain's dormant vegetative state.

10. A fluorescence reporter plasmid system comprising a sequence selected from SEQ ID Nos: 3-13.

11. The fluorescence reporter plasmid system according to claim 1, wherein expression of the first reporter gene is under the control of one or more spore-specific promoters, and wherein expression of the second reporter gene is under the control of one or more vegetative state-specific promoters.

12. The fluorescence reporter plasmid system according to claim 1, wherein expression of the first fluorescent protein is controlled by one or more promoters selected from sspA, sspB, sspC, sspD, sspE, sspF, sspG, sspH, sspI, sspJ, sspK, sspL, sspM, sspN, sspO and sspP promoters, and wherein expression of the second fluorescent protein is controlled by one or more promoters selected from amyLp, amyQp, cryp and rplKp promoters.

13. The fluorescence reporter plasmid system according to claim 1, wherein the first reporter gene is translationally fused to sequence comprising SEQ ID NO: 14.

14. A method of visualizing the state of a *Bacillus* strain in an animal, a plant or a plant seed comprising:

a) introducing a fluorescence reporter plasmid system according to claim 1 into a *Bacillus* strain, b) treating an animal or a plant seed with the *Bacillus* strain of step (a), c) collecting samples from the treated animal or plant seed of step (b), d) optionally staining the samples of step (c) with DNA dyes, and e) imaging the samples of step (c) or (d) to visualize the state of the *Bacillus* strain.

15. A method of visualizing the state of a *Bacillus* strain in vitro or in vivo, wherein a fluorescence reporter plasmid system according to claim 1 is transformed into said *Bacillus* strain, thereby enabling said *Bacillus* strain to fluoresce said first color in its dormant endospore state and to fluoresce said second color in its metabolically active vegetative state.

16. The plasmid system according to claim 9, wherein the linker encodes between 6 to 20 amino acids.

17. The plasmid system according to claim 9, wherein the linker encodes between 11 to 13 amino acids.

18. The plasmid system according to claim 9, wherein the linker encodes about 12 amino acids.

19. A *Bacillus* strain comprising a fluorescent reporter plasmid system according to claim 1.

20. A *Bacillus* strain comprising a fluorescent reporter plasmid system that comprises one or more sequences selected from SEQ ID NOs: 3-13.

* * * * *

SEQUENCE LISTING

<160> NUMBER OF SEQ ID NOS: 14

<210> SEQ ID NO 1
<211> LENGTH: 7252
<212> TYPE: DNA
<213> ORGANISM: Artificial Sequence
<220> FEATURE:
<223> OTHER INFORMATION: Backbone of plasmid

<400> SEQUENCE: 1
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420
ttcggtcaga tgcaattcga catgtggacg gactggttac aagtgataaa gatttctttg 480
atgatttaag cggagaagaa atagaacgat tttttaaaga tagcttggag tttctagagc 540
ggccgcatta ttaatctgtt cagcaatcgg gcgcgattgc tgaataaaag atacgagaga 600
cctctcttgt atctttttta ttttgagtgg ttttgtccgt tacactagaa aaccgaaaga 660
caataaaaat tttattcttg ctgagtctgg ctttcggtaa gctagacaaa acggacaaaa 720
taaaaattgg caagggttta aaggtggaga tttttttgagt gatcttctca aaaaatacta 780
cctgtccctt gctgattttt aaacgagcac gagagcaaaa ccccccttttg ctgaggtggc 840 agagggcagg ttttttttgtt tcttttttct cgtaaaaaaa agaaaggtct taaaggtttt 900
atggttttgg tcggcactgc cgacagcctc gcagagcaca cactttatga atataaagta 960
tagtgtgtta tactttactt ggaagtggtt gccggaaaga gcgaaaatgc ctcacatttg 1020
tgccacctaa aaaggagcga tttacatatg agttatgcag tttgtagaat gcaaaaagtg 1080
aaatcagctg gactaaaagg cagcggccgc caccgcggtg gagctccagc ttttgttccc 1140
tttagtgagg gttaattgcg cgcttggcgt aatcatggtc atagctgttt cctgtgtgaa 1200
attgttatcc gctcacaatt ccacacaaca tacgagccgg aagcataaag tgtaaagcct 1260
ggggtgccta atgagtgagc taactcacat taattgcgtt gcgctcactg cccgctttcc 1320
agtcgggaaa cctgtcgtgc cagctgcatt aatgaatcgg ccaacgcgcg gggagaggcg 1380
gtttgcgtat tgggcgctct tccgcttcct cgctcactga ctcgctgcgc tcggtcgttc 1440
ggctgcggcg agcggtatca gctcactcaa aggcggtaat acggttatcc acagaatcag 1500
gggataacgc aggaaagaac atgtgagcaa aaggccagca aaaggccagg aaccgtaaaa 1560
aggccgcgtt gctggcgttt ttccataggc tccgcccccc tgacgagcat cacaaaaatc 1620
gacgctcaag tcagaggtgg cgaaacccga caggactata aagataccag gcgtttcccc 1680
ctggaagctc cctcgtgcgc tctcctgttc cgaccctgcc gcttaccgga tacctgtccg 1740
cctttctccc ttcgggaagc gtggcgcttt ctcatagctc acgctgtagg tatctcagtt 1800
cggtgtaggt cgttcgctcc aagctgggct gtgtgcacga accccccgtt cagcccgacc 1860
gctgcgcctt atccggtaac tatcgtcttg agtccaaccc ggtaagacac gacttatcgc 1920
cactggcagc agccactggt aacaggatta gcagagcgag gtatgtaggc ggtgctacag 1980
agttcttgaa gtggtggcct aactacggct acactagaag aacagtattt ggtatctgcg 2040

```
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ccccctcgag gtcgacggta tcgataagct   4020
tgatatcgaa ttcctgcagc ccgggggatc cactagttct agaaaatgaa tacggtaagg   4080
aaaatatgct gtatgcgact gtccatctgg atgaaagagt cccacatatg cactttggtt   4140
ttgtcccttt aacagaggac gggagattgt ctgcaaaaga acagttaggc aacaagaaag   4200
actttactca attacaagat agatttaatg agtatgtgaa tgagaaaggt tatgaacttg   4260
aaagaggcac gtccaaagag gttacagaac gagaacataa agcgatggat cagtacaaga   4320
aagatactgt atttcataaa caggaactgc aagaagttaa ggatgagtta cagaaggcaa   4380
```

-continued ataagcagtt acagagtgga atagagcata tgaggtctac gaaacccttt gattatgaaa 4440
atgagcgtac aggtttgttc tctggacgtg aagagactgg tagaaagata ttaactgctg 4500
atgaatttga acgcctgcaa gaaacaatct cttctgcaga acggattgtt gatgattacg 4560
aaaatattaa gagcacagac tattacacag aaaatcaaga attaaaaaaa cgtagagaga 4620
gtttgaaaga agtagtgaat acatggaaag aggggtatca cgaaaaaagt aaagaggtta 4680
ataaattaaa gcgagagaat gatagtttga atgagcagtt gaatgtatca gagaaatttc 4740
aagatagtac agtgacttta tatcgtgctg cgagggcgaa tttccctggg tttgagaaag 4800
ggtttaatag gcttaaagag aaattcttta atgattccaa attcgagcgt gtgggacagt 4860
ttatggatgt tgtacaggat aatgtccaga aggtcgatag aaagcgtgag aaacagcgta 4920
cagacgattt agagatgtag aggtactttt atgccgagaa aactttttgc gtgtgacagt 4980
ccttaaaata tacttagagc gtaagcgaaa gtagtagcga cagctattaa ctttcggttg 5040
caaagctcta ggatttttaa tggacgcagc gcatcacacg caaaaaggaa attggaataa 5100
atgcgaaatt tgagatgtta attaaagacc tttttgaggt ctttttttct tagatttttg 5160
gggttattta ggggagaaaa catagggggg tactacgacc tccccccctag gtgtccattg 5220 tccattgtcc aaacaaataa ataaatattg ggtttttaat gttaaaaggt tgttttttat 5280
gttaaagtga aaaaaacaga tgttgggagg tacagtgatg gttgtagata gaaaagaaga 5340
gaaaaaagtt gctgttactt taagacttac aacagaagaa aatgagatat taaatagaat 5400
caaagaaaaa tataatatta gcaaatcaga tgcaaccggt attctaataa aaaaatatgc 5460
aaaggaggaa tacggtgcat tttaaacaaa aaaagataga cagcactggc atgctgccta 5520
tctatgacta aattttgtta aatgtattag caccgttatt atatcatgag cgaaaatgta 5580
ataaaagaaa ctgaaaacaa gaaaaattca agaggacgta attggacatt tgttttatat 5640
ccagaatcag caaaagccga gtggttagag tatttaaaag agttacacat tcaatttgta 5700
gtgtctccat tacatgatag ggatactgat acagaagata ggatgaaaaa agagcattat 5760
catattctag tgatgtatga gggtaataaa tcttatgaac agataaaaat aattacagaa 5820
gaattgaatg cgactattcc gcagattgca ggaagtgtga aaggtcttgt gagatatatg 5880
cttcacatgg acgatcctaa taaatttaaa tatcaaaaag aagatatgat agtttatggc 5940
ggtgtagatg ttgatgaatt attaaagaaa acaacaacag atagatataa attaattaaa 6000
gaaatgattg agtttattga tgaacaagga atcgtagaat ttaagagttt aatggattat 6060
gcaatgaagt ttaaatttga tgattggttc ccgcttttat gtgataactc ggcgtatgtt 6120
attcaagaat atataaaatc aaatcggtat aaatctgacc gatagatttt gaatttaggt 6180
gtcacaagac actctttttt cgcaccaacg aaaactggtt taagccgact gcgcaaaaga 6240
cataatcgat tcacaaaaaa taggcacacg aaaaacaagt taagggatgc agtttatgca 6300
tcccttaact tacttattaa ataatttata gctattgaaa agagataaga attgttcaaa 6360
gctaatattg tttaaatcgt caattcctgc atgttttaag gaattgttaa attgattttt 6420
tgtaaatatt ttcttgtatt ctttgttaac ccatttcata acgaaataat tatacttttg 6480
tttatctttg tgtgatattc ttgatttttt tctacttaat ctgataagtg agctattcac 6540
tttaggttta ggatgaaaat attctcttgg aaccatactt aatatagaaa tatcaacttc 6600
tgccattaaa agtaatgcca atgagcgttt tgtatttaat aatcttttag caaacccgta 6660
ttccacgatt aaataaatct cattagctat actatcaaaa acaattttgc gtattatatc 6720
cgtacttatg ttataaggta tattaccata tattttatag gattggtttt taggaaattt 6780

```
aaactgcaat atatccttgt ttaaaacttg gaaattatcg tgatcaacaa gtttattttc   6840

tgtagttttg cataatttat ggtctatttc aatggcagtt acgaaattac acctctttac   6900

taattcaagg gtaaaatggc cttttcctga gccgatttca aagatattat catgttcatt   6960

taatcttata tttgtcatta ttttatctat attatgtttt gaagtaataa agttttgact   7020

gtgttttata tttttctcgt tcattataac cctctttaat ttggttatat gaattttgct   7080

tattaacgat tcattataac cacttatttt ttgtttggtt gataatgaac tgtgctgatt   7140

acaaaaatac taaaaatgcc catatttttt cctccttata aaattagtat aattatagca   7200

cgagctctga taaatatgaa catgatgagt gatcgttaaa tttatactgc aa           7252


<210> SEQ ID NO 2
<211> LENGTH: 6918
<212> TYPE: DNA
<213> ORGANISM: Artificial Sequence
<220> FEATURE:
<223> OTHER INFORMATION: Backbone of plasmid

<400> SEQUENCE: 2

ctagagcggc cgccaccgcg gtggagctcc agcttttgtt ccctttagtg agggttaatt     60

gcgcgcttgg cgtaatcatg gtcatagctg tttcctgtgt gaaattgtta tccgctcaca    120

attccacaca acatacgagc cggaagcata aagtgtaaag cctggggtgc ctaatgagtg    180

agctaactca cattaattgc gttgcgctca ctgcccgctt tccagtcggg aaacctgtcg    240

tgccagctgc attaatgaat cggccaacgc gcggggagag gcggtttgcg tattgggcgc    300

tcttccgctt cctcgctcac tgactcgctg cgctcggtcg ttcggctgcg gcgagcggta    360

tcagctcact caaaggcggt aatacggtta tccacagaat caggggataa cgcaggaaag    420

aacatgtgag caaaaggcca gcaaaaggcc aggaaccgta aaaaggccgc gttgctggcg    480

tttttccata ggctccgccc ccctgacgag catcacaaaa atcgacgctc aagtcagagg    540

tggcgaaacc cgacaggact ataaagatac caggcgtttc cccctggaag ctccctcgtg    600

cgctctcctg ttccgaccct gccgcttacc ggatacctgt ccgcctttct cccttcggga    660

agcgtggcgc tttctcatag ctcacgctgt aggtatctca gttcggtgta ggtcgttcgc    720

tccaagctgg gctgtgtgca cgaacccccc gttcagcccg accgctgcgc cttatccggt    780

aactatcgtc ttgagtccaa cccggtaaga cacgacttat cgccactggc agcagccact    840

ggtaacagga ttagcagagc gaggtatgta ggcggtgcta cagagttctt gaagtggtgg    900

cctaactacg gctacactag aagaacagta tttggtatct gcgctctgct gaagccagtt    960

accttcggaa aaagagttgg tagctcttga tccggcaaac aaaccaccgc tggtagcggt   1020

ggtttttttg tttgcaagca gcagattacg cgcagaaaaa aaggatctca agaagatcct   1080

ttgatctttt ctacggggtc tgacgctcag tggaacgaaa actcacgtta agggattttg   1140

gtcatgagat tatcaaaaag gatcttcacc tagatccttt taaattaaaa atgaagtttt   1200

aaatcaatct aaagtatata tgagtaaact tggtctgaca gttaccaatg cttaatcagt   1260

gaggcaccta tctcagcgat ctgtctattt cgttcatcca tagttgcctg actccccgtc   1320

gtgtagataa ctacgatacg ggagggctta ccatctggcc ccagtgctgc aatgataccg   1380

cgagacccac gctcaccggc tccagattta tcagcaataa accagccagc cggaagggcc   1440

gagcgcagaa gtggtcctgc aactttatcc gcctccatcc agtctattaa ttgttgccgg   1500

gaagctagag taagtagttc gccagttaat agtttgcgca acgttgttgc cattgctaca   1560
```

-continued

```
ggcatcgtgg tgtcacgctc gtcgtttggt atggcttcat tcagctccgg ttcccaacga   1620
tcaaggcgag ttacatgatc ccccatgttg tgcaaaaaag cggttagctc cttcggtcct   1680
ccgatcgttg tcagaagtaa gttggccgca gtgttatcac tcatggttat ggcagcactg   1740
cataattctc ttactgtcat gccatccgta agatgctttt ctgtgactgg tgagtactca   1800
accaagtcat tctgagaata gtgtatgcgg cgaccgagtt gctcttgccc ggcgtcaata   1860
cgggataata ccgcgccaca tagcagaact ttaaaagtgc tcatcattgg aaaacgttct   1920
tcggggcgaa aactctcaag gatcttaccg ctgttgagat ccagttcgat gtaacccact   1980
cgtgcaccca actgatcttc agcatctttt actttcacca gcgtttctgg gtgagcaaaa   2040
acaggaaggc aaaatgccgc aaaaaaggga ataagggcga cacggaaatg ttgaatactc   2100
atactcttcc tttttcaata ttattgaagc atttatcagg gttattgtct catgagcgga   2160
tacatatttg aatgtattta gaaaaataaa caaatagggg ttccgcgcac atttccccga   2220
aaagtgccac ctaaattgta agcgttaata ttttgttaaa attcgcgtta aatttttgtt   2280
aaatcagctc attttttaac caataggccg aaatcggcaa aatcccttat aaatcaaaag   2340
aatagaccga gatagggttg agtgttgttc cagtttggaa caagagtcca ctattaaaga   2400
acgtggactc caacgtcaaa gggcgaaaaa ccgtctatca gggcgatggc ccactacgtg   2460
aaccatcacc ctaatcaagt tttttggggt cgaggtgccg taaagcacta aatcggaacc   2520
ctaaagggag cccccgattt agagcttgac ggggaaagcc ggcgaacgtg gcgagaaagg   2580
aagggaagaa agcgaaagga gcgggcgcta gggcgctggc aagtgtagcg gtcacgctgc   2640
gcgtaaccac cacacccgcc gcgcttaatg cgccgctaca gggcgcgtcc cattcgccat   2700
tcaggctgcg caactgttgg gaagggcgat cggtgcgggc ctcttcgcta ttacgccagc   2760
tggcgaaagg gggatgtgct gcaaggcgat taagttgggt aacgccaggg ttttcccagt   2820
cacgacgttg taaaacgacg gccagtgagc gcgcgtaata cgactcacta tagggcgaat   2880
tgggtaccgg gccccccctc gaggtcgacg gtatcgataa gctcatgacc atggcataac   2940
cctgcttcgg ggtcattata gcgatttttt cggtatatcc atcctttttc gcacgatata   3000
caggattttg ccaaagggtt cgtgtagact ttccttggtg tatccaacgg cgtcagccgg   3060
gcaggatagg tgaagtaggc ccacccgcga gcgggtgttc cttcttcact gtcccttatt   3120
cgcacctggc ggtgctcaac gggaatcctg ttgatatcga attcctgcag cccgggggat   3180
ccactagttc tagaaaatga atacggtaag gaaaatatgc tgtatgcgac tgtccatctg   3240
gatgaaagag tcccacatat gcactttggt tttgtccctt taacagagga cgggagattg   3300
tctgcaaaag aacagttagg caacaagaaa gactttactc aattacaaga tagatttaat   3360
gagtatgtga atgagaaagg ttatgaactt gaaagaggca cgtccaaaga ggttacagaa   3420
cgagaacata aagcgatgga tcagtacaag aaagatactg tatttcataa acaggaactg   3480
caagaagtta aggatgagtt acagaaggca aataagcagt tacagagtgg aatagagcat   3540
atgaggtcta cgaaaccctt tgattatgaa aatgagcgta caggtttgtt ctctggacgt   3600
gaagagactg gtagaaagat attaactgct gatgaatttg aacgcctgca agaaacaatc   3660
tcttctgcag aacggattgt tgatgattac gaaaatatta agagcacaga ctattacaca   3720
gaaaatcaag aattaaaaaa acgtagagag agtttgaaag aagtagtgaa tacatggaaa   3780
gaggggtatc acgaaaaaag taaagaggtt aataaattaa agcgagagaa tgatagtttg   3840
aatgagcagt tgaatgtatc agagaaattt caagatagta cagtgacttt atatcgtgct   3900
gcgagggcga atttccctgg gtttgagaaa gggtttaata ggcttaaaga gaaattcttt   3960
```

```
aatgattcca aattcgagcg tgtgggacag tttatggatg ttgtacagga taatgtccag   4020
aaggtcgata gaaagcgtga gaaacagcgt acagacgatt tagagatgta gaggtacttt   4080
tatgccgaga aaactttttg cgtgtgacag tccttaaaat atacttagag cgtaagcgaa   4140
agtagtagcg acagctatta actttcggtt gcaaagctct aggattttta atggacgcag   4200
cgcatcacac gcaaaaagga aattggaata aatgcgaaat ttgagatgtt aattaaagac   4260
ctttttgagg tctttttttc ttagattttt ggggttattt aggggagaaa acataggggg   4320
gtactacgac ctccccccta ggtgtccatt gtccattgtc caaacaaata aataaatatt   4380
gggtttttaa tgttaaaagg ttgtttttta tgttaaagtg aaaaaaacag atgttgggag   4440
gtacagtgat ggttgtagat agaaaagaag agaaaaaagt tgctgttact ttaagactta   4500
caacagaaga aaatgagata ttaaatagaa tcaaagaaaa atataatatt agcaaatcag   4560
atgcaaccgg tattctaata aaaaaatatg caaaggagga atacggtgca ttttaaacaa   4620
aaaaagatag acagcactgg catgctgcct atctatgact aaattttgtt aaatgtatta   4680
gcaccgttat tatatcatga gcgaaaatgt aataaaagaa actgaaaaca agaaaaattc   4740
aagaggacgt aattggacat ttgttttata tccagaatca gcaaaagccg agtggttaga   4800
gtatttaaaa gagttacaca ttcaatttgt agtgtctcca ttacatgata gggatactga   4860
tacagaagat aggatgaaaa aagagcatta tcatattcta gtgatgtatg agggtaataa   4920
atcttatgaa cagataaaaa taattacaga agaattgaat gcgactattc cgcagattgc   4980
aggaagtgtg aaaggtcttg tgagatatat gcttcacatg gacgatccta ataaatttaa   5040
atatcaaaaa gaagatatga tagtttatgg cggtgtagat gttgatgaat tattaaagaa   5100
aacaacaaca gatagatata aattaattaa agaaatgatt gagtttattg atgaacaagg   5160
aatcgtagaa tttaagagtt taatggatta tgcaatgaag tttaaatttg atgattggtt   5220
cccgctttta tgtgataact cggcgtatgt tattcaagaa tatataaaat caaatcggta   5280
taaatctgac cgatagattt tgaatttaag agtgtcacaa gacactcttt tttcgcacca   5340
acgaaaactg gtttaagccg actgcgcaaa agacataatc gattcacaaa aaataggcac   5400
acgaaaaaca agttaaggga tgcagtttat gcatccctta acttacttat taaataattt   5460
atagctattg aaaagagata agaattgttc aaagctaata ttgtttaaat cgtcaattcc   5520
tgcatgtttt aaggaattgt taaattgatt ttttgtaaat attttcttgt attctttgtt   5580
aacccatttc ataacgaaat aattatactt ttgtttatct ttgtgtgata ttcttgattt   5640
ttttctactt aatctgataa gtgagctatt cactttaggt ttaggatgaa aatattctct   5700
tggaaccata cttaatatag aaatatcaac ttctgccatt aaaagtaatg ccaatgagcg   5760
ttttgtattt aataatcttt tagcaaaccc gtattccacg attaaataaa tctcattagc   5820
tatactatca aaaacaattt tgcgtattat atccgtactt atgttataag gtatattacc   5880
atatatttta taggattggt ttttaggaaa tttaaactgc aatatatcct tgtttaaaac   5940
ttggaaatta tcgtgatcaa caagtttatt ttctgtagtt ttgcataatt tatggtctat   6000
ttcaatggca gttacgaaat tacacctctt tactaattca agggtaaaat ggccttttcc   6060
tgagccgatt tcaaagatat tatcatgttc atttaatctt atatttgtca ttattttatc   6120
tatattatgt tttgaagtaa taaagttttg actgtgtttt atatttttct cgttcattat   6180
aaccctcttt aatttggtta tatgaatttt gcttattaac gattcattat aaccacttat   6240
tttttgtttg gttgataatg aactgtgctg attacaaaaa tactaaaaat gcccatattt   6300
```

```
tttcctcctt ataaaattag tataattata gcacgagctc tgataaatat gaacatgatg   6360

agtgatcgtt aaatttatac tgcaatcgga tgcgattatt gaataaaaga tatgagagat   6420

ttatctaatt tcttttttct tgtaaaaaaa gaaagttctt aaaggtttta tagttttggt   6480

cgtagagcac acggtttaac gacttaatta cgaagtaaat aagtctagtg tgttagactt   6540

tatgaaatct atatacgttt atatatattt attatccgga ggtgtagcat gtctcattca   6600

attttgaggg ttgccagagt taaaggatca agtaatacaa acgggataca aagacataat   6660

caaagagaga ataaaaacta taataataaa gacataaatc atgaggaaac atataaaaat   6720

tatgatttga ttaacgcaca aaatataaag tataaagata aaattgatga aacgattgat   6780

gagaattatt cagggaaacg taaaattcgg tcagatgcaa ttcgacatgt ggacggactg   6840

gttacaagtg ataaagattt ctttgatgat ttaagcggag aagaaataga acgatttttt   6900

aaagatagct tggagttt                                                 6918
```

<210> SEQ ID NO 3
<211> LENGTH: 8309
<212> TYPE: DNA
<213> ORGANISM: Artificial Sequence
<220> FEATURE:
<223> OTHER INFORMATION: Plasmid system

<400> SEQUENCE: 3

```
tcggatgcga ttattgaata aaagatatga gagatttatc taatttcttt tttcttgtaa     60

aaaaagaaag ttcttaaagg ttttatagtt ttggtcgtag agcacacggt ttaacgactt    120

aattacgaag taaataagtc tagtgtgtta gactttatga aatctatata cgtttatata    180

tatttattat ccggaggtgt agcatgtctc attcaatttt gagggttgcc agagttaaag    240

gatcaagtaa tacaaacggg atacaaagac ataatcaaag agagaataaa aactataata    300

ataaagacat aaatcatgag gaaacatata aaaattatga tttgattaac gcacaaaata    360

taaagtataa agataaaatt gatgaaacga ttgatgagaa ttattcaggg aaacgtaaaa    420

ttcggtcaga tgcaattcga catgtggacg gactggttac aagtgataaa gatttctttg    480

atgatttaag cggagaagaa atagaacgat tttttaaaga tagcttggag tttctagagc    540

ggccgcatta ttaatctgtt cagcaatcgg gcgcgattgc tgaataaaag atacgagaga    600

cctctcttgt atctttttta ttttgagtgg ttttgtccgt tacactagaa aaccgaaaga    660

caataaaaat tttattcttg ctgagtctgg ctttcggtaa gctagacaaa acggacaaaa    720

taaaaattgg caagggttta aaggtggaga ttttttgagt gatcttctca aaaaatacta    780

cctgtccctt gctgattttt aaacgagcac gagagcaaaa ccccccctttg ctgaggtggc    840

agagggcagg tttttttgtt tctttttttct cgtaaaaaaa agaaaggtct taaaggtttt    900

atggttttgg tcggcactgc cgacagcctc gcagagcaca cactttatga atataaagta    960

tagtgtgtta tactttactt ggaagtggtt gccggaaaga gcgaaaatgc ctcacatttg   1020

tgccacctaa aaaggagcga tttacatatg agttatgcag tttgtagaat gcaaaaagtg   1080

aaatcagctg gactaaaagg cagcggccgc caccgcggtg gagctccagc ttttgttccc   1140

tttagtgagg gttaattgcg cgcttggcgt aatcatggtc atagctgttt cctgtgtgaa   1200

attgttatcc gctcacaatt ccacacaaca tacgagccgg aagcataaag tgtaaagcct   1260

ggggtgccta atgagtgagc taactcacat taattgcgtt gcgctcactg cccgctttcc   1320

agtcgggaaa cctgtcgtgc cagctgcatt aatgaatcgg ccaacgcgcg gggagaggcg   1380

gtttgcgtat tgggcgctct tccgcttcct cgctcactga ctcgctgcgc tcggtcgttc   1440
```

```
ggctgcggcg agcggtatca gctcactcaa aggcggtaat acggttatcc acagaatcag   1500
gggataacgc aggaaagaac atgtgagcaa aaggccagca aaaggccagg aaccgtaaaa   1560
aggccgcgtt gctggcgttt ttccataggc tccgcccccc tgacgagcat cacaaaaatc   1620
gacgctcaag tcagaggtgg cgaaacccga caggactata aagataccag gcgtttcccc   1680
ctggaagctc cctcgtgcgc tctcctgttc cgaccctgcc gcttaccgga tacctgtccg   1740
cctttctccc ttcgggaagc gtggcgcttt ctcatagctc acgctgtagg tatctcagtt   1800
cggtgtaggt cgttcgctcc aagctgggct gtgtgcacga accccccgtt cagcccgacc   1860
gctgcgcctt atccggtaac tatcgtcttg agtccaaccc ggtaagacac gacttatcgc   1920
cactggcagc agccactggt aacaggatta gcagagcgag gtatgtaggc ggtgctacag   1980
agttcttgaa gtggtggcct aactacggct acactagaag aacagtattt ggtatctgcg   2040
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
```

```
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ccccctcgag gtcgacggta tcgataagct   4020
tgatatcgaa ttcctgcaga cggacctttc gccaacttta caggatcaat tgaagagatt   4080
gattatgata agagcaaagt gaaagtattc gttaacatgt tcggccgtga aacgccggtt   4140
gaactggaat ttacccagat cgacaaattg taatgtgaaa aaacttgaaa ttgctatata   4200
ttaatgataa tatagcaaag gtacgtcttg gactaatcca aggcagctag cttgatattt   4260
cgtcattcat ataaagaatg aaaccttgag tgggagggtt taccctatta ccacatcacg   4320
gacttaagga ggtgtgtctc atgagtaaag gagaagaact tttcactgga gttgtcccaa   4380
ttcttgttga attagatggc gatgttaatg ggcaaaaatt ctctgttagt ggagagggtg   4440
aaggtgatgc aacatacgga aaacttaccc ttaaatttat ttgcactact gggaagctac   4500
ctgttccatg gccaacgctt gtcactactc tcacttatgg tgttcaatgc ttttctagat   4560
acccagatca tatgaaacag catgactttt tcaagagtgc catgcccgaa ggttatgtac   4620
aggaaagaac tatattttac aaagatgacg ggaactacaa gacacgtgct gaagtcaagt   4680
ttgaaggtga taccettgtt aatagaatcg agttaaaagg tattgatttt aaagaagatg   4740
gaaacattct tggacacaaa atggaataca attataactc acataatgta tacatcatgg   4800
cagacaaacc aaagaatggc atcaaagtta acttcaaaat tagacacaac attaaagatg   4860
gaagcgttca attagcagac cattatcaac aaaatactcc aattggcgat ggccctgtcc   4920
ttttaccaga caaccattac ctgtccacgc aatctgccct ttccaaagat cccaacgaaa   4980
agagagatca catgatcctt cttgagtttg taacagctgc tgggattaca catggcatgg   5040
atgaactata caaataactg ataattgcca acacattaac atctcaatca aggtaacccg   5100
ggggatccac tagttctaga aaatgaatac ggtaaggaaa atatgctgta tgcgactgtc   5160
catctggatg aaagagtccc acatatgcac tttggttttg tccctttaac agaggacggg   5220
agattgtctg caaaagaaca gttaggcaac aagaaagact ttactcaatt acaagataga   5280
tttaatgagt atgtgaatga gaaaggttat gaacttgaaa gaggcacgtc caaagaggtt   5340
acagaacgag aacataaagc gatggatcag tacaagaaag atactgtatt tcataaacag   5400
gaactgcaag aagttaagga tgagttacag aaggcaaata agcagttaca gagtggaata   5460
gagcatatga ggtctacgaa accctttgat tatgaaaatg agcgtacagg tttgttctct   5520
ggacgtgaag agactggtag aaagatatta actgctgatg aatttgaacg cctgcaagaa   5580
acaatctctt ctgcagaacg gattgttgat gattacgaaa atattaagag cacagactat   5640
tacacagaaa atcaagaatt aaaaaaacgt agagagagtt tgaaagaagt agtgaataca   5700
tggaaagagg ggtatcacga aaaaagtaaa gaggttaata aattaaagcg agagaatgat   5760
agtttgaatg agcagttgaa tgtatcagag aaatttcaag atagtacagt gactttatat   5820
cgtgctgcga gggcgaattt ccctgggttt gagaaagggt ttaataggct taaagagaaa   5880
ttctttaatg attccaaatt cgagcgtgtg ggacagttta tggatgttgt acaggataat   5940
gtccagaagg tcgatagaaa gcgtgagaaa cagcgtacag acgatttaga gatgtagagg   6000
tacttttatg ccgagaaaac tttttgcgtg tgacagtcct taaaatatac ttagagcgta   6060
agcgaaagta gtagcgacag ctattaactt tcggttgcaa agctctagga tttttaatgg   6120
acgcagcgca tcacacgcaa aaaggaaatt ggaataaatg cgaaatttga gatgttaatt   6180
```

aaagaccttt ttgaggtctt tttttcttag atttttgggg ttatttaggg gagaaaacat 6240
agggggtac tacgacctcc cccctaggtg tccattgtcc attgtccaaa caaataaata 6300
aatattgggt ttttaatgtt aaaaggttgt tttttatgtt aaagtgaaaa aaacagatgt 6360
tgggaggtac agtgatggtt gtagatagaa aagaagagaa aaaagttgct gttactttaa 6420
gacttacaac agaagaaaat gagatattaa atagaatcaa agaaaaatat aatattagca 6480
aatcagatgc aaccggtatt ctaataaaaa aatatgcaaa ggaggaatac ggtgcatttt 6540
aaacaaaaaa agatagacag cactggcatg ctgcctatct atgactaaat tttgttaaat 6600
gtattagcac cgttattata tcatgagcga aaatgtaata aaagaaactg aaaacaagaa 6660
aaattcaaga ggacgtaatt ggacatttgt tttatatcca gaatcagcaa aagccgagtg 6720
gttagagtat ttaaaagagt tacacattca atttgtagtg tctccattac atgataggga 6780
tactgataca gaagatagga tgaaaaaaga gcattatcat attctagtga tgtatgaggg 6840
taataaatct tatgaacaga taaaaataat tacagaagaa ttgaatgcga ctattccgca 6900
gattgcagga agtgtgaaag gtcttgtgag atatatgctt cacatggacg atcctaataa 6960
atttaaatat caaaaagaag atatgatagt ttatggcggt gtagatgttg atgaattatt 7020
aaagaaaaca acaacagata gatataaatt aattaaagaa atgattgagt ttattgatga 7080
acaaggaatc gtagaattta agagtttaat ggattatgca atgaagttta aatttgatga 7140
ttggttcccg cttttatgtg ataactcggc gtatgttatt caagaatata taaaatcaaa 7200
tcggtataaa tctgaccgat agattttgaa tttaggtgtc acaagacact ctttttcgc 7260
accaacgaaa actggtttaa gccgactgcg caaaagacat aatcgattca caaaaaatag 7320
gcacacgaaa aacaagttaa gggatgcagt ttatgcatcc cttaacttac ttattaaata 7380
atttatagct attgaaaaga gataagaatt gttcaaagct aatattgttt aaatcgtcaa 7440
ttcctgcatg ttttaaggaa ttgttaaatt gattttttgt aaatattttc ttgtattctt 7500
tgttaaccca tttcataacg aaataattat acttttgttt atctttgtgt gatattcttg 7560
atttttttct acttaatctg ataagtgagc tattcacttt aggtttagga tgaaaatatt 7620
ctcttggaac catacttaat atagaaatat caacttctgc cattaaaagt aatgccaatg 7680
agcgttttgt atttaataat cttttagcaa acccgtattc cacgattaaa taaatctcat 7740
tagctatact atcaaaaaca attttgcgta ttatatccgt acttatgtta taaggtatat 7800
taccatatat tttataggat tggtttttag gaaatttaaa ctgcaatata tccttgttta 7860
aaacttggaa attatcgtga tcaacaagtt tattttctgt agttttgcat aatttatggt 7920
ctatttcaat ggcagttacg aaattacacc tctttactaa ttcaagggta aaatggcctt 7980
ttcctgagcc gatttcaaag atattatcat gttcatttaa tcttatattt gtcattattt 8040
tatctatatt atgttttgaa gtaataaagt tttgactgtg ttttatattt ttctcgttca 8100
ttataaccct ctttaatttg gttatatgaa ttttgcttat taacgattca ttataaccac 8160
ttattttttg tttggttgat aatgaactgt gctgattaca aaaatactaa aaatgcccat 8220
attttttcct ccttataaaa ttagtataat tatagcacga gctctgataa atatgaacat 8280
gatgagtgat cgttaaattt atactgcaa 8309

<210> SEQ ID NO 4
<211> LENGTH: 7632
<212> TYPE: DNA
<213> ORGANISM: Artificial Sequence
<220> FEATURE:

<223> OTHER INFORMATION: Plasmid system

<400> SEQUENCE: 4
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420
ttcggtcaga tgcaattcga catgtggacg gactggttac aagtgataaa gatttctttg 480
atgatttaag cggagaagaa atagaacgat tttttaaaga tagcttggag tttctagagc 540
ggccgcatta ttaatctgtt cagcaatcgg gcgcgattgc tgaataaaag atacgagaga 600
cctctcttgt atcttttta ttttgagtgg ttttgtccgt tacactagaa aaccgaaaga 660
caataaaaat tttattcttg ctgagtctgg ctttcggtaa gctagacaaa acggacaaaa 720
taaaaattgg caagggttta aaggtggaga ttttttgagt gatcttctca aaaaatacta 780
cctgtccctt gctgattttt aaacgagcac gagagcaaaa cccccctttg ctgaggtggc 840
agagggcagg ttttttttgtt tcttttttct cgtaaaaaaa agaaaggtct taaaggtttt 900
atggttttgg tcggcactgc cgacagcctc gcagagcaca cactttatga atataaagta 960
tagtgtgtta tactttactt ggaagtggtt gccggaaaga gcgaaaatgc ctcacatttg 1020
tgccacctaa aaaggagcga tttacatatg agttatgcag tttgtagaat gcaaaaagtg 1080
aaatcagctg gactaaaagg cagcggccgc caccgcggtg gagctccagc ttttgttccc 1140
tttagtgagg gttaattgcg cgcttggcgt aatcatggtc atagctgttt cctgtgtgaa 1200
attgttatcc gctcacaatt ccacacaaca tacgagccgg aagcataaag tgtaaagcct 1260
ggggtgccta atgagtgagc taactcacat taattgcgtt gcgctcactg cccgctttcc 1320
agtcgggaaa cctgtcgtgc cagctgcatt aatgaatcgg ccaacgcgcg gggagaggcg 1380
gtttgcgtat tgggcgctct tccgcttcct cgctcactga ctcgctgcgc tcggtcgttc 1440
ggctgcggcg agcggtatca gctcactcaa aggcggtaat acggttatcc acagaatcag 1500
gggataacgc aggaaagaac atgtgagcaa aaggccagca aaaggccagg aaccgtaaaa 1560
aggccgcgtt gctggcgttt ttccataggc tccgcccccc tgacgagcat cacaaaaatc 1620
gacgctcaag tcagaggtgg cgaaacccga caggactata aagataccag gcgtttcccc 1680
ctggaagctc cctcgtgcgc tctcctgttc cgaccctgcc gcttaccgga tacctgtccg 1740
cctttctccc ttcgggaagc gtggcgcttt ctcatagctc acgctgtagg tatctcagtt 1800
cggtgtaggt cgttcgctcc aagctgggct gtgtgcacga accccccgtt cagcccgacc 1860
gctgcgcctt atccggtaac tatcgtcttg agtccaaccc ggtaagacac gacttatcgc 1920
cactggcagc agccactggt aacaggatta gcagagcgag gtatgtaggc ggtgctacag 1980
agttcttgaa gtggtggcct aactacggct acactagaag aacagtattt ggtatctgcg 2040
ctctgctgaa gccagttacc ttcggaaaaa gagttggtag ctcttgatcc ggcaaacaaa 2100
ccaccgctgg tagcggtggt ttttttgttt gcaagcagca gattacgcgc agaaaaaaag 2160
gatctcaaga agatcctttg atcttttcta cggggtctga cgctcagtgg aacgaaaact 2220
cacgttaagg gattttggtc atgagattat caaaaaggat cttcacctag atccttttaa 2280

```
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ccccctcgag gtcgacggta tcgataagct   4020
tgatatcgaa ttcctgcagc ccgggggatc cttatttgta tagttcatcc atgccatgtg   4080
taatcccagc agctgttaca aactcaagaa ggatcatgtg atctctcttt tcgttgggat   4140
ctttggaaag ggcagattgc gtggacaggt aatggttgtc tggtaaaagg acagggccat   4200
cgccaattgg agtattttgt tgataatggt ctgctaattg aacgcttcca tctttaatgt   4260
tgtgtctaat tttgaagtta actttgatgc cattctttgg tttgtctgcc atgatgtata   4320
cattatgtga gttataattg tattccattt tgtgtccaag aatgtttcca tcttctttaa   4380
aatcaatacc ttttaactcg attctattaa caagggtatc accttcaaac ttgacttcag   4440
cacgtgtctt gtagttcccg tcatctttgt aaaatatagt tctttcctgt acataacctt   4500
cgggcatggc actcttgaaa aagtcatgct gtttcatatg atctgggtat ctagaaaagc   4560
attgaacacc ataagtgaga gtagtgacaa gcgttggcca tggaacaggt agcttcccag   4620
```

```
tagtgcaaat aaatttaagg gtaagttttc cgtatgttgc atcaccttca ccctctccac   4680
taacagagaa tttttgccca ttaacatcgc catctaattc aacaagaatt gggacaactc   4740
cagtgaaaag ttcttctcct ttactcatcg ttggttccgg cgttggttcc ggcgttggtt   4800
ccggttgtac gccttggccg cccatgttct gctgtgcgaa agatactaaa cgtttagtga   4860
tttctcctcc gacagaaccg tttgcacgag aagttgtttc tccgccaagg tttacgccga   4920
actcagaagc aatttcgtat ttcatttggt cgattgcttg agcagcgccg ggtactacta   4980
gttggtttga agagttgttg tttgccattt gtatgatctc ctttataaag tagtatggtt   5040
gggtttgctg gaattgcacc agccgatgat tttcggaatg aaaaccattg ccagctcggc   5100
ttcacccaat gctgtttgcc gctttgtact acgtattatg gtgaatcaaa cggcatctca   5160
ttcggaaaac ggtgtggtaa atagcggaag gaaaaagaaa agcccagcct ggtgcggctg   5220
agcttttagc tttcagtcat atatgtgata aagcattaat tcatgcagct cttttacgag   5280
agccggctct tcttttcccg gatgtgtgtg tccccattca atgtctccgg acttatggta   5340
aatcccttcg taatgcgtac cctgccagta aaatgaaatc cgccatccgg gcagtttctc   5400
ttttttgaat aacggtttcc agctgaagtg cgaaatcatg acgttcacgc tccttatggg   5460
aaatgttgat cttgttcatt gtagctcatc gttcaatgcc tgtcccggcc tttttgaggt   5520
cttttttttct tagattttttg gggttattta ggggagaaaa catagggggg tactacgacc   5580
tccccccctag gtgtccattg tccattgtcc aaacaaataa ataaatattg ggtttttaat   5640
gttaaaaggt tgttttttat gttaaagtga aaaaaacaga tgttgggagg tacagtgatg   5700
gttgtagata gaaaagaaga gaaaaaagtt gctgttactt taagacttac aacagaagaa   5760
aatgagatat taaatagaat caaagaaaaa tataatatta gcaaatcaga tgcaaccggt   5820
attctaataa aaaaatatgc aaaggaggaa tacggtgcat tttaaacaaa aaaagataga   5880
cagcactggc atgctgccta tctatgacta aattttgtta aatgtattag caccgttatt   5940
atatcatgag cgaaaatgta ataaaagaaa ctgaaaacaa gaaaaattca agaggacgta   6000
attggacatt tgttttatat ccagaatcag caaaagccga gtggttagag tatttaaaag   6060
agttacacat tcaatttgta gtgtctccat tacatgatag ggatactgat acagaagata   6120
ggatgaaaaa agagcattat catattctag tgatgtatga gggtaataaa tcttatgaac   6180
agataaaaat aattacagaa gaattgaatg cgactattcc gcagattgca ggaagtgtga   6240
aaggtcttgt gagatatatg cttcacatgg acgatcctaa taaatttaaa tatcaaaaag   6300
aagatatgat agtttatggc ggtgtagatg ttgatgaatt attaaagaaa acaacaacag   6360
atagatataa attaattaaa gaaatgattg agtttattga tgaacaagga atcgtagaat   6420
ttaagagttt aatggattat gcaatgaagt ttaaatttga tgattggttc ccgcttttat   6480
gtgataactc ggcgtatgtt attcaagaat atataaaatc aaatcggtat aaatctgacc   6540
gatagatttt gaatttaggt gtcacaagac actctttttt cgcaccaacg aaaactggtt   6600
taagccgact gcgcaaaaga cataatcgat tcacaaaaaa taggcacacg aaaaacaagt   6660
taagggatgc agtttatgca tcccttaact tacttattaa ataatttata gctattgaaa   6720
agagataaga attgttcaaa gctaatattg tttaaatcgt caattcctgc atgttttaag   6780
gaattgttaa attgattttt tgtaaatatt ttcttgtatt ctttgttaac ccatttcata   6840
acgaaataat tatacttttg tttatctttg tgtgatattc ttgatttttt tctacttaat   6900
ctgataagtg agctattcac tttaggttta ggatgaaaat attctcttgg aaccatactt   6960
aatatagaaa tatcaacttc tgccattaaa agtaatgcca atgagcgttt tgtatttaat   7020
```

aatcttttag caaacccgta ttccacgatt aaataaatct cattagctat actatcaaaa 7080
acaattttgc gtattatatc cgtacttatg ttataaggta tattaccata tattttatag 7140
gattggtttt taggaaattt aaactgcaat atatccttgt ttaaaacttg gaaattatcg 7200
tgatcaacaa gtttattttc tgtagttttg cataatttat ggtctatttc aatggcagtt 7260
acgaaattac acctctttac taattcaagg gtaaaatggc cttttcctga gccgatttca 7320
aagatattat catgttcatt taatcttata tttgtcatta ttttatctat attatgtttt 7380
gaagtaataa agttttgact gtgttttata tttttctcgt tcattataac cctctttaat 7440
ttggttatat gaattttgct tattaacgat tcattataac cacttatttt ttgtttggtt 7500
gataatgaac tgtgctgatt acaaaaatac taaaaatgcc catatttttt cctccttata 7560
aaattagtat aattatagca cgagctctga taaatatgaa catgatgagt gatcgttaaa 7620
tttatactgc aa 7632

<210> SEQ ID NO 5
<211> LENGTH: 9188
<212> TYPE: DNA
<213> ORGANISM: Artificial Sequence
<220> FEATURE:
<223> OTHER INFORMATION: Plasmid system

<400> SEQUENCE: 5
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420
ttcggtcaga tgcaattcga catgtggacg gactggttac aagtgataaa gatttctttg 480
atgatttaag cggagaagaa atagaacgat tttttaaaga tagcttggag tttctagagc 540
ggccgcatta ttaatctgtt cagcaatcgg gcgcgattgc tgaataaaag atacgagaga 600
cctctcttgt atcttttta ttttgagtgg ttttgtccgt tacactagaa aaccgaaaga 660
caataaaaat tttattcttg ctgagtctgg ctttcggtaa gctagacaaa acggacaaaa 720
taaaaattgg caagggttta aaggtggaga ttttttgagt gatcttctca aaaaatacta 780
cctgtccctt gctgattttt aaacgagcac gagagcaaaa ccccccttg ctgaggtggc 840
agagggcagg tttttttgtt tctttttct cgtaaaaaaa agaaaggtct taaaggtttt 900
atggttttgg tcggcactgc cgacagcctc gcagagcaca cactttatga atataaagta 960
tagtgtgtta tactttactt ggaagtggtt gccggaaaga gcgaaaatgc ctcacatttg 1020
tgccacctaa aaaggagcga tttacatatg agttatgcag tttgtagaat gcaaaaagtg 1080
aaatcagctg gactaaaagg cagcggccgc caccgcggtg gagctccagc ttttgttccc 1140
tttagtgagg gttaattgcg cgcttggcgt aatcatggtc atagctgttt cctgtgtgaa 1200
attgttatcc gctcacaatt ccacacaaca tacgagccgg aagcataaag tgtaaagcct 1260
ggggtgccta atgagtgagc taactcacat taattgcgtt gcgctcactg cccgctttcc 1320
agtcgggaaa cctgtcgtgc cagctgcatt aatgaatcgg ccaacgcgcg gggagaggcg 1380
gtttgcgtat tgggcgctct tccgcttcct cgctcactga ctcgctgcgc tcggtcgttc 1440
ggctgcggcg agcggtatca gctcactcaa aggcggtaat acggttatcc acagaatcag 1500
gggataacgc aggaaagaac atgtgagcaa aaggccagca aaaggccagg aaccgtaaaa 1560
aggccgcgtt gctggcgttt ttccataggc tccgcccccc tgacgagcat cacaaaaatc 1620
gacgctcaag tcagaggtgg cgaaacccga caggactata aagataccag gcgtttcccc 1680
ctggaagctc cctcgtgcgc tctcctgttc cgaccctgcc gcttaccgga tacctgtccg 1740
cctttctccc ttcgggaagc gtggcgcttt ctcatagctc acgctgtagg tatctcagtt 1800
cggtgtaggt cgttcgctcc aagctgggct gtgtgcacga accccccgtt cagcccgacc 1860
gctgcgcctt atccggtaac tatcgtcttg agtccaaccc ggtaagacac gacttatcgc 1920
cactggcagc agccactggt aacaggatta gcagagcgag gtatgtaggc ggtgctacag 1980
agttcttgaa gtggtggcct aactacggct acactagaag aacagtattt ggtatctgcg 2040
ctctgctgaa gccagttacc ttcggaaaaa gagttggtag ctcttgatcc ggcaaacaaa 2100
ccaccgctgg tagcggtggt ttttttgttt gcaagcagca gattacgcgc agaaaaaaag 2160
gatctcaaga agatcctttg atcttttcta cggggtctga cgctcagtgg aacgaaaact 2220
cacgttaagg gattttggtc atgagattat caaaaaggat cttcacctag atccttttaa 2280
attaaaaatg aagttttaaa tcaatctaaa gtatatatga gtaaacttgg tctgacagtt 2340
accaatgctt aatcagtgag gcacctatct cagcgatctg tctatttcgt tcatccatag 2400
ttgcctgact ccccgtcgtg tagataacta cgatacggga gggcttacca tctggcccca 2460
gtgctgcaat gataccgcga gacccacgct caccggctcc agatttatca gcaataaacc 2520
agccagccgg aagggccgag cgcagaagtg gtcctgcaac tttatccgcc tccatccagt 2580
ctattaattg ttgccgggaa gctagagtaa gtagttcgcc agttaatagt ttgcgcaacg 2640
ttgttgccat tgctacaggc atcgtggtgt cacgctcgtc gtttggtatg gcttcattca 2700
gctccggttc ccaacgatca aggcgagtta catgatcccc catgttgtgc aaaaaagcgg 2760
ttagctcctt cggtcctccg atcgttgtca gaagtaagtt ggccgcagtg ttatcactca 2820
tggttatggc agcactgcat aattctctta ctgtcatgcc atccgtaaga tgcttttctg 2880
tgactggtga gtactcaacc aagtcattct gagaatagtg tatgcggcga ccgagttgct 2940
cttgcccggc gtcaatacgg gataataccg cgccacatag cagaacttta aaagtgctca 3000
tcattggaaa acgttcttcg gggcgaaaac tctcaaggat cttaccgctg ttgagatcca 3060
gttcgatgta acccactcgt gcacccaact gatcttcagc atcttttact ttcaccagcg 3120
tttctgggtg agcaaaaaca ggaaggcaaa atgccgcaaa aaagggaata agggcgacac 3180
ggaaatgttg aatactcata ctcttccttt ttcaatatta ttgaagcatt tatcagggtt 3240
attgtctcat gagcggatac atatttgaat gtatttagaa aaataaacaa ataggggttc 3300
cgcgcacatt tccccgaaaa gtgccaccta aattgtaagc gttaatattt tgttaaaatt 3360
cgcgttaaat ttttgttaaa tcagctcatt ttttaaccaa taggccgaaa tcggcaaaat 3420
cccttataaa tcaaaagaat agaccgagat agggttgagt gttgttccag tttggaacaa 3480
gagtccacta ttaaagaacg tggactccaa cgtcaaaggg cgaaaaaccg tctatcaggg 3540
cgatggccca ctacgtgaac catcacccta atcaagtttt ttggggtcga ggtgccgtaa 3600
agcactaaat cggaacccta aagggagccc ccgatttaga gcttgacggg gaaagccggc 3660
gaacgtggcg agaaaggaag ggaagaaagc gaaaggagcg ggcgctaggg cgctggcaag 3720
tgtagcggtc acgctgcgcg taaccaccac acccgccgcg cttaatgcgc cgctacaggg 3780
cgcgtcccat tcgccattca ggctgcgcaa ctgttgggaa gggcgatcgg tgcgggcctc 3840
ttcgctatta cgccagctgg cgaaaggggg atgtgctgca aggcgattaa gttgggtaac 3900
gccagggttt tcccagtcac gacgttgtaa aacgacggcc agtgagcgcg cgtaatacga 3960
ctcactatag ggcgaattgg gtaccgggcc tgctgtccag actgtccgct gtgtaaaaaa 4020
aaggaataaa gggggggttga cattatttta ctgatatgta taatataatt tgtataagaa 4080
aatggagggg ccctcgaaac gtaagatgaa accttagata aaagtgcttt ttttgttgca 4140
attgaagaat tattaatgtt aagcttaatt aaagataata tctttgaatt gtaacgcccc 4200
tcaaaagtaa gaactacaaa aaaagaatac gttatataga aatatgtttg aaccttcttc 4260
agattacaaa tatattcgga cggactctac ctcaaatgct tatctaacta tagaatgaca 4320
tacaagcaca accttgaaaa tttgaaaata taactaccaa tgaacttgtt catgtgaatt 4380
atcgctgtat ttaattttct caattcaata tataatatgc caatacattg ttacaagtag 4440
aaattaagac acccttgata gccttactat acctaacatg atgtagtatt aaatgaatat 4500
gtaaatatat ttatgataag aagcgactta tttataatca ttacatattt ttctattgga 4560
atgattaaga ttccaataga atagtgtata aattatttat cttgaaagga gggatggcta 4620
aaaacgaaga acattaaaaa catatatttg caccgtctaa tggatttatg aaaaatcatt 4680
ttatcagttt gaaaattatg tattatggag ctcttataaa aatgaggagg gaaccgaatg 4740
gcttcaactg aagacgtaat caaagagttc atgcgcttca aagtgcgaat ggaaggaagt 4800
gtaaacgggc atgagtttga aattgaaggt gaaggtgaag gaaggcctta tgaaggaacg 4860
caaactgcaa aacttaaagt gacaaaagga ggaccgctgc cgtttgcttg ggacatctta 4920
agtccgcagt ttcagtatgg gtcaaaagtt tatgtaaagc atcctgctga cattcctgat 4980
tacaaaaagt taagttttcc tgaaggattc aagtgggagc gcgtaatgaa ctttgaagat 5040
ggaggtgtcg taactgtaac gcaagattca agtctgcaag acggttgctt catttacaaa 5100
gtaaagttca ttggcgtgaa ctttccaagt gatggtcctg taatgcagaa aaagacaatg 5160
ggttgggagc cgtcaactga gaggctttat ccgcgtgatg gtgtcttgaa aggtgaaatt 5220
cacaaagcct taaagttgaa agatggaggg cattatcttg ttgagttcaa gagcatttac 5280
atggcgaaaa agcctgtgca gcttcctggc tactactatg ttgattcaaa acttgacata 5340
actagtcaca acgaagacta cacaattgtt gagcagtatg agcgaactga aggaaggcat 5400
catctttttc tttaagagac cagacttcca attgacacta aagggatcca gaagcggcaa 5460
cacgctaatc aataaaaaaa cgctgtgcgg ttaaagggca cagcgttttt tgtgtatgaa 5520
tcgaaaaaga ggagagatcg caggcccccc ctcgaggtcg acggtatcga taagcttgat 5580
atcgaattcc tgcagcccgg gggatcctta tttgtatagt tcatccatgc catgtgtaat 5640
cccagcagct gttacaaact caagaaggat catgtgatct ctcttttcgt tgggatcttt 5700
ggaaagggca gattgcgtgg acaggtaatg gttgtctggt aaaaggacag ggccatcgcc 5760
aattggagta ttttgttgat aatggtctgc taattgaacg cttccatctt taatgttgtg 5820
tctaattttg aagttaactt tgatgccatt ctttggtttg tctgccatga tgtatacatt 5880
atgtgagtta taattgtatt ccattttgtg tccaagaatg tttccatctt ctttaaaatc 5940
aataccttttt aactcgattc tattaacaag ggtatcacct tcaaacttga cttcagcacg 6000
tgtcttgtag ttcccgtcat ctttgtaaaa tatagttctt tcctgtacat aaccttcggg 6060
catggcactc ttgaaaaagt catgctgttt catatgatct gggtatctag aaaagcattg 6120

```
aacaccataa gtgagagtag tgacaagcgt tggccatgga acaggtagct tcccagtagt   6180
gcaaataaat ttaagggtaa gttttccgta tgttgcatca ccttcaccct ctccactaac   6240
agagaatttt tgcccattaa catcgccatc taattcaaca agaattggga caactccagt   6300
gaaaagttct tctcctttac tcatcgttgg ttccggcgtt ggttccggcg ttggttccgg   6360
ttgtacgcct tggccgccca tgttctgctg tgcgaaagat actaaacgtt tagtgatttc   6420
tcctccgaca gaaccgtttg cacgagaagt tgtttctccg ccaaggttta cgccgaactc   6480
agaagcaatt tcgtatttca tttggtcgat tgcttgagca gcgccgggta ctactagttg   6540
gtttgaagag ttgttgtttg ccatttgtat gatctccttt ataaagtagt atggttgggt   6600
ttgctggaat tgcaccagcc gatgattttc ggaatgaaaa ccattgccag ctcggcttca   6660
cccaatgctg tttgccgctt tgtactacgt attatggtga atcaaacggc atctcattcg   6720
gaaaacggtg tggtaaatag cggaaggaaa aagaaaagcc cagcctggtg cggctgagct   6780
tttagctttc agtcatatat gtgataaagc attaattcat gcagctcttt tacgagagcc   6840
ggctcttctt ttcccggatg tgtgtgtccc cattcaatgt ctccggactt atggtaaatc   6900
ccttcgtaat gcgtaccctg ccagtaaaat gaaatccgcc atccgggcag tttctctttt   6960
ttgaataacg gtttccagct gaagtgcgaa atcatgacgt tcacgctcct tatgggaaat   7020
gttgatcttg ttcattgtag ctcatcgttc aatgcctgtc ccggcctttt tgaggtcttt   7080
ttttcttaga tttttggggt tatttagggg agaaaacata ggggggtact acgacctccc   7140
ccctaggtgt ccattgtcca ttgtccaaac aaataaataa atattgggtt tttaatgtta   7200
aaaggttgtt ttttatgtta aagtgaaaaa aacagatgtt gggaggtaca gtgatggttg   7260
tagatagaaa agaagagaaa aaagttgctg ttactttaag acttacaaca gaagaaaatg   7320
agatattaaa tagaatcaaa gaaaaatata atattagcaa atcagatgca accggtattc   7380
taataaaaaa atatgcaaag gaggaatacg gtgcatttta aacaaaaaaa gatagacagc   7440
actggcatgc tgcctatcta tgactaaatt ttgttaaatg tattagcacc gttattatat   7500
catgagcgaa aatgtaataa aagaaactga aaacaagaaa aattcaagag gacgtaattg   7560
gacatttgtt ttatatccag aatcagcaaa agccgagtgg ttagagtatt taaaagagtt   7620
acacattcaa tttgtagtgt ctccattaca tgatagggat actgatacag aagataggat   7680
gaaaaaagag cattatcata ttctagtgat gtatgagggt aataaatctt atgaacagat   7740
aaaaataatt acagaagaat tgaatgcgac tattccgcag attgcaggaa gtgtgaaagg   7800
tcttgtgaga tatatgcttc acatggacga tcctaataaa tttaaatatc aaaaagaaga   7860
tatgatagtt tatggcggtg tagatgttga tgaattatta aagaaaacaa caacagatag   7920
atataaatta attaaagaaa tgattgagtt tattgatgaa caaggaatcg tagaatttaa   7980
gagtttaatg gattatgcaa tgaagtttaa atttgatgat tggttcccgc ttttatgtga   8040
taactcggcg tatgttattc aagaatatat aaaatcaaat cggtataaat ctgaccgata   8100
gattttgaat ttaggtgtca caagacactc tttttcgca ccaacgaaaa ctggtttaag   8160
ccgactgcgc aaaagacata atcgattcac aaaaaatagg cacacgaaaa acaagttaag   8220
ggatgcagtt tatgcatccc ttaacttact tattaaataa tttatagcta ttgaaaagag   8280
ataagaattg ttcaaagcta atattgttta aatcgtcaat tcctgcatgt tttaaggaat   8340
tgttaaattg atttttgta aatattttct tgtattcttt gttaacccat ttcataacga   8400
aataattata cttttgttta tctttgtgtg atattcttga tttttttcta cttaatctga   8460
taagtgagct attcacttta ggtttaggat gaaaatattc tcttggaacc atacttaata   8520
```

```
tagaaatatc aacttctgcc attaaaagta atgccaatga gcgttttgta tttaataatc   8580

ttttagcaaa cccgtattcc acgattaaat aaatctcatt agctatacta tcaaaaacaa   8640

ttttgcgtat tatatccgta cttatgttat aaggtatatt accatatatt ttataggatt   8700

ggtttttagg aaatttaaac tgcaatatat ccttgtttaa aacttggaaa ttatcgtgat   8760

caacaagttt attttctgta gttttgcata atttatggtc tatttcaatg gcagttacga   8820

aattacacct ctttactaat tcaagggtaa aatggccttt tcctgagccg atttcaaaga   8880

tattatcatg ttcatttaat cttatatttg tcattatttt atctatatta tgttttgaag   8940

taataaagtt ttgactgtgt tttatatttt tctcgttcat tataaccctc tttaatttgg   9000

ttatatgaat tttgcttatt aacgattcat tataaccact tattttttgt ttggttgata   9060

atgaactgtg ctgattacaa aaatactaaa aatgcccata ttttttcctc cttataaaat   9120

tagtataatt atagcacgag ctctgataaa tatgaacatg atgagtgatc gttaaattta   9180

tactgcaa                                                            9188
```

<210> SEQ ID NO 6
<211> LENGTH: 8397
<212> TYPE: DNA
<213> ORGANISM: Artificial Sequence
<220> FEATURE:
<223> OTHER INFORMATION: Plasmid system

<400> SEQUENCE: 6

```
tcggatgcga ttattgaata aaagatatga gagatttatc taatttcttt tttcttgtaa     60

aaaaagaaag ttcttaaagg ttttatagtt ttggtcgtag agcacacggt ttaacgactt    120

aattacgaag taaataagtc tagtgtgtta gactttatga aatctatata cgtttatata    180

tatttattat ccggaggtgt agcatgtctc attcaatttt gagggttgcc agagttaaag    240

gatcaagtaa tacaaacggg atacaaagac ataatcaaag agagaataaa aactataata    300

ataaagacat aaatcatgag gaaacatata aaaattatga tttgattaac gcacaaaata    360

taaagtataa agataaaatt gatgaaacga ttgatgagaa ttattcaggg aaacgtaaaa    420

ttcggtcaga tgcaattcga catgtggacg gactggttac aagtgataaa gatttctttg    480

atgatttaag cggagaagaa atagaacgat tttttaaaga tagcttggag tttctagagc    540

ggccgcatta ttaatctgtt cagcaatcgg gcgcgattgc tgaataaaag atacgagaga    600

cctctcttgt atctttttta ttttgagtgg ttttgtccgt tacactagaa aaccgaaaga    660

caataaaaat tttattcttg ctgagtctgg ctttcggtaa gctagacaaa acggacaaaa    720

taaaaattgg caagggttta aaggtggaga ttttttgagt gatcttctca aaaaatacta    780

cctgtccctt gctgattttt aaacgagcac gagagcaaaa cccccctttg ctgaggtggc    840

agagggcagg ttttttttgtt tcttttttct cgtaaaaaaa agaaaggtct taaaggtttt    900

atggttttgg tcggcactgc cgacagcctc gcagagcaca cactttatga atataaagta    960

tagtgtgtta tactttactt ggaagtggtt gccggaaaga gcgaaaatgc ctcacatttg   1020

tgccacctaa aaaggagcga tttacatatg agttatgcag tttgtagaat gcaaaaagtg   1080

aaatcagctg gactaaaagg cagcggccgc caccgcggtg gagctccagc ttttgttccc   1140

tttagtgagg gttaattgcg cgcttggcgt aatcatggtc atagctgttt cctgtgtgaa   1200

attgttatcc gctcacaatt ccacacaaca tacgagccgg aagcataaag tgtaaagcct   1260

ggggtgccta atgagtgagc taactcacat taattgcgtt gcgctcactg cccgctttcc   1320
```

-continued

```
agtcgggaaa cctgtcgtgc cagctgcatt aatgaatcgg ccaacgcgcg gggagaggcg   1380
gtttgcgtat tgggcgctct tccgcttcct cgctcactga ctcgctgcgc tcggtcgttc   1440
ggctgcggcg agcggtatca gctcactcaa aggcggtaat acggttatcc acagaatcag   1500
gggataacgc aggaaagaac atgtgagcaa aaggccagca aaaggccagg aaccgtaaaa   1560
aggccgcgtt gctggcgttt ttccataggc tccgcccccc tgacgagcat cacaaaaatc   1620
gacgctcaag tcagaggtgg cgaaacccga caggactata aagataccag gcgtttcccc   1680
ctggaagctc cctcgtgcgc tctcctgttc cgaccctgcc gcttaccgga tacctgtccg   1740
cctttctccc ttcgggaagc gtggcgcttt ctcatagctc acgctgtagg tatctcagtt   1800
cggtgtaggt cgttcgctcc aagctgggct gtgtgcacga accccccgtt cagcccgacc   1860
gctgcgcctt atccggtaac tatcgtcttg agtccaaccc ggtaagacac gacttatcgc   1920
cactggcagc agccactggt aacaggatta gcagagcgag gtatgtaggc ggtgctacag   1980
agttcttgaa gtggtggcct aactacggct acactagaag aacagtattt ggtatctgcg   2040
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
```

```
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ccccctcgag gtcgacggta tcgataagct   4020
tgatatcgaa ttcctgcaga cggacctttc gccaacttta caggatcaat tgaagagatt   4080
gattatgata agagcaaagt gaaagtattc gttaacatgt tcggccgtga aacgccggtt   4140
gaactggaat ttacccagat cgacaaattg taatgtgaaa aacttgaaa ttgctatata   4200
ttaatgataa tatagcaaag gtacgtcttg gactaatcca aggcagctag cttgatattt   4260
cgtcattcat ataaagaatg aaaccttgag tgggagggtt taccctatta ccacatcacg   4320
gacttaagga ggtgtgtctc atggcttcaa ctgaagacgt aatcaaagag ttcatgcgct   4380
tcaaagtgcg aatggaagga agtgtaaacg ggcatgagtt tgaaattgaa ggtgaaggtg   4440
aaggaaggcc ttatgaagga acgcaaactg caaaacttaa agtgacaaaa ggaggaccgc   4500
tgccgtttgc ttgggacatc ttaagtccgc agtttcagta tgggtcaaaa gtttatgtaa   4560
agcatcctgc tgacattcct gattacaaaa agttaagttt tcctgaagga ttcaagtggg   4620
agcgcgtaat gaactttgaa gatggaggtg tcgtaactgt aacgcaagat tcaagtctgc   4680
aagacggttg cttcatttac aaagtaaagt tcattggcgt gaactttcca agtgatggtc   4740
ctgtaatgca gaaaaagaca atgggttggg agccgtcaac tgagaggctt tatccgcgtg   4800
atggtgtctt gaaaggtgaa attcacaaag ccttaaagtt gaaagatgga gggcattatc   4860
ttgttgagtt caagagcatt tacatggcga aaaagcctgt gcagcttcct ggctactact   4920
atgttgattc aaaacttgac ataactagtc acaacgaaga ctacacaatt gttgagcagt   4980
atgagcgaac tgaaggaagg catcatcttt ttctttaaga gaccagactt ccaattgaca   5040
ctaaagggat ccagaagcgg caacacgcta atcaataaaa aaacgctgtg cggttaaagg   5100
gcacagcgtt ttttgtgtat gaatcgaaaa agaggagaga tcgcactgat aattgccaac   5160
acattaacat ctcaatcaag gtaacccggg ggatccacta gttctagaaa atgaatacgg   5220
taaggaaaat atgctgtatg cgactgtcca tctggatgaa agagtcccac atatgcactt   5280
tggttttgtc cctttaacag aggacgggag attgtctgca aaagaacagt taggcaacaa   5340
gaaagacttt actcaattac aagatagatt taatgagtat gtgaatgaga aaggttatga   5400
acttgaaaga ggcacgtcca aagaggttac agaacgagaa cataaagcga tggatcagta   5460
caagaaagat actgtatttc ataaacagga actgcaagaa gttaaggatg agttacagaa   5520
ggcaaataag cagttacaga gtggaataga gcatatgagg tctacgaaac cctttgatta   5580
tgaaaatgag cgtacaggtt tgttctctgg acgtgaagag actggtagaa agatattaac   5640
tgctgatgaa tttgaacgcc tgcaagaaac aatctcttct gcagaacgga ttgttgatga   5700
ttacgaaaat attaagagca cagactatta cacagaaaat caagaattaa aaaaacgtag   5760
agagagtttg aaagaagtag tgaatacatg gaaagagggg tatcacgaaa aaagtaaaga   5820
ggttaataaa ttaaagcgag agaatgatag tttgaatgag cagttgaatg tatcagagaa   5880
atttcaagat agtacagtga ctttatatcg tgctgcgagg gcgaatttcc ctgggtttga   5940
gaaagggttt aataggctta aagagaaatt ctttaatgat tccaaattcg agcgtgtggg   6000
acagtttatg gatgttgtac aggataatgt ccagaaggtc gatagaaagc gtgagaaaca   6060
```

-continued

```
gcgtacagac gatttagaga tgtagaggta cttttatgcc gagaaaactt tttgcgtgtg   6120
acagtcctta aaatatactt agagcgtaag cgaaagtagt agcgacagct attaactttc   6180
ggttgcaaag ctctaggatt tttaatggac gcagcgcatc acacgcaaaa aggaaattgg   6240
aataaatgcg aaatttgaga tgttaattaa agaccttttt gaggtctttt tttcttagat   6300
ttttggggtt atttagggga gaaaacatag gggggtacta cgacctcccc cctaggtgtc   6360
cattgtccat tgtccaaaca aataaataaa tattgggttt ttaatgttaa aaggttgttt   6420
tttatgttaa agtgaaaaaa acagatgttg ggaggtacag tgatggttgt agatagaaaa   6480
gaagagaaaa aagttgctgt tactttaaga cttacaacag aagaaaatga gatattaaat   6540
agaatcaaag aaaaatataa tattagcaaa tcagatgcaa ccggtattct aataaaaaaa   6600
tatgcaaagg aggaatacgg tgcattttaa acaaaaaaag atagacagca ctggcatgct   6660
gcctatctat gactaaattt tgttaaatgt attagcaccg ttattatatc atgagcgaaa   6720
atgtaataaa agaaactgaa aacaagaaaa attcaagagg acgtaattgg acatttgttt   6780
tatatccaga atcagcaaaa gccgagtggt tagagtattt aaaagagtta cacattcaat   6840
ttgtagtgtc tccattacat gatagggata ctgatacaga agataggatg aaaaaagagc   6900
attatcatat tctagtgatg tatgagggta ataaatctta tgaacagata aaaataatta   6960
cagaagaatt gaatgcgact attccgcaga ttgcaggaag tgtgaaaggt cttgtgagat   7020
atatgcttca catggacgat cctaataaat ttaaatatca aaaagaagat atgatagttt   7080
atggcggtgt agatgttgat gaattattaa agaaaacaac aacagataga tataaattaa   7140
ttaaagaaat gattgagttt attgatgaac aaggaatcgt agaatttaag agtttaatgg   7200
attatgcaat gaagtttaaa tttgatgatt ggttcccgct tttatgtgat aactcggcgt   7260
atgttattca agaatatata aaatcaaatc ggtataaatc tgaccgatag attttgaatt   7320
taggtgtcac aagacactct tttttcgcac caacgaaaac tggtttaagc cgactgcgca   7380
aaagacataa tcgattcaca aaaaataggc acacgaaaaa caagttaagg gatgcagttt   7440
atgcatccct taacttactt attaaataat ttatagctat tgaaaagaga taagaattgt   7500
tcaaagctaa tattgtttaa atcgtcaatt cctgcatgtt ttaaggaatt gttaaattga   7560
tttttgtaa atattttctt gtattctttg ttaacccatt tcataacgaa ataattatac   7620
ttttgtttat ctttgtgtga tattcttgat ttttttctac ttaatctgat aagtgagcta   7680
ttcactttag gtttaggatg aaaatattct cttggaacca tacttaatat agaaatatca   7740
acttctgcca ttaaaagtaa tgccaatgag cgttttgtat ttaataatct tttagcaaac   7800
ccgtattcca cgattaaata aatctcatta gctatactat caaaaacaat tttgcgtatt   7860
atatccgtac ttatgttata aggtatatta ccatatattt tataggattg gtttttagga   7920
aatttaaact gcaatatatc cttgtttaaa acttggaaat tatcgtgatc aacaagttta   7980
ttttctgtag ttttgcataa tttatggtct atttcaatgg cagttacgaa attacacctc   8040
tttactaatt caagggtaaa atggcctttt cctgagccga tttcaaagat attatcatgt   8100
tcatttaatc ttatatttgt cattatttta tctatattat gttttgaagt aataaagttt   8160
tgactgtgtt ttatattttt ctcgttcatt ataaccctct ttaatttggt tatatgaatt   8220
ttgcttatta acgattcatt ataaccactt atttttgtt tggttgataa tgaactgtgc    8280
tgattacaaa aatactaaaa atgcccatat tttttcctcc ttataaaatt agtataatta   8340
tagcacgagc tctgataaat atgaacatga tgagtgatcg ttaaatttat actgcaa      8397
```

<210> SEQ ID NO 7
<211> LENGTH: 9136
<212> TYPE: DNA
<213> ORGANISM: Artificial Sequence
<220> FEATURE:
<223> OTHER INFORMATION: Plasmid system

<400> SEQUENCE: 7
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420
ttcggtcaga tgcaattcga catgtggacg gactggttac aagtgataaa gatttctttg 480
atgatttaag cggagaagaa atagaacgat tttttaaaga tagcttggag tttctagagc 540
ggccgcatta ttaatctgtt cagcaatcgg gcgcgattgc tgaataaaag atacgagaga 600
cctctcttgt atctttttta ttttgagtgg ttttgtccgt tacactagaa aaccgaaaga 660
caataaaaat tttattcttg ctgagtctgg ctttcggtaa gctagacaaa acggacaaaa 720
taaaaattgg caagggttta aaggtggaga ttttttgagt gatcttctca aaaaatacta 780
cctgtccctt gctgattttt aaacgagcac gagagcaaaa ccccccttg ctgaggtggc 840 agagggcagg tttttttgtt tcttttttct cgtaaaaaaa agaaaggtct taaaggtttt 900
atggttttgg tcggcactgc cgacagcctc gcagagcaca cactttatga atataaagta 960
tagtgtgtta tactttactt ggaagtggtt gccggaaaga gcgaaaatgc ctcacatttg 1020
tgccacctaa aaaggagcga tttacatatg agttatgcag tttgtagaat gcaaaaagtg 1080
aaatcagctg gactaaaagg cagcggccgc caccgcggtg gagctccagc ttttgttccc 1140
tttagtgagg gttaattgcg cgcttggcgt aatcatggtc atagctgttt cctgtgtgaa 1200
attgttatcc gctcacaatt ccacacaaca tacgagccgg aagcataaag tgtaaagcct 1260
ggggtgccta atgagtgagc taactcacat taattgcgtt gcgctcactg cccgctttcc 1320
agtcgggaaa cctgtcgtgc cagctgcatt aatgaatcgg ccaacgcgcg gggagaggcg 1380
gtttgcgtat tgggcgctct tccgcttcct cgctcactga ctcgctgcgc tcggtcgttc 1440
ggctgcggcg agcggtatca gctcactcaa aggcggtaat acggttatcc acagaatcag 1500
gggataacgc aggaaagaac atgtgagcaa aaggccagca aaaggccagg aaccgtaaaa 1560
aggccgcgtt gctggcgttt ttccataggc tccgcccccc tgacgagcat cacaaaaatc 1620
gacgctcaag tcagaggtgg cgaaacccga caggactata aagataccag gcgtttcccc 1680
ctggaagctc cctcgtgcgc tctcctgttc cgaccctgcc gcttaccgga tacctgtccg 1740
cctttctccc ttcgggaagc gtggcgcttt ctcatagctc acgctgtagg tatctcagtt 1800
cggtgtaggt cgttcgctcc aagctgggct gtgtgcacga accccccgtt cagcccgacc 1860
gctgcgcctt atccggtaac tatcgtcttg agtccaaccc ggtaagacac gacttatcgc 1920
cactggcagc agccactggt aacaggatta gcagagcgag gtatgtaggc ggtgctacag 1980
agttcttgaa gtggtggcct aactacggct acactagaag aacagtattt ggtatctgcg 2040
ctctgctgaa gccagttacc ttcggaaaaa gagttggtag ctcttgatcc ggcaaacaaa 2100

-continued ccaccgctgg tagcggtggt ttttttgttt gcaagcagca gattacgcgc agaaaaaaag 2160
gatctcaaga agatcctttg atcttttcta cggggtctga cgctcagtgg aacgaaaact 2220
cacgttaagg gattttggtc atgagattat caaaaaggat cttcacctag atccttttaa 2280
attaaaaatg aagttttaaa tcaatctaaa gtatatatga gtaaacttgg tctgacagtt 2340
accaatgctt aatcagtgag gcacctatct cagcgatctg tctatttcgt tcatccatag 2400
ttgcctgact ccccgtcgtg tagataacta cgatacggga gggcttacca tctggcccca 2460
gtgctgcaat gataccgcga gacccacgct caccggctcc agatttatca gcaataaacc 2520
agccagccgg aagggccgag cgcagaagtg gtcctgcaac tttatccgcc tccatccagt 2580
ctattaattg ttgccgggaa gctagagtaa gtagttcgcc agttaatagt ttgcgcaacg 2640
ttgttgccat tgctacaggc atcgtggtgt cacgctcgtc gtttggtatg gcttcattca 2700
gctccggttc ccaacgatca aggcgagtta catgatcccc catgttgtgc aaaaaagcgg 2760
ttagctcctt cggtcctccg atcgttgtca gaagtaagtt ggccgcagtg ttatcactca 2820
tggttatggc agcactgcat aattctctta ctgtcatgcc atccgtaaga tgcttttctg 2880
tgactggtga gtactcaacc aagtcattct gagaatagtg tatgcggcga ccgagttgct 2940
cttgcccggc gtcaatacgg gataataccg cgccacatag cagaacttta aaagtgctca 3000
tcattggaaa acgttcttcg gggcgaaaac tctcaaggat cttaccgctg ttgagatcca 3060
gttcgatgta acccactcgt gcacccaact gatcttcagc atcttttact ttcaccagcg 3120
tttctgggtg agcaaaaaca ggaaggcaaa atgccgcaaa aaagggaata agggcgacac 3180
ggaaatgttg aatactcata ctcttccttt ttcaatatta ttgaagcatt tatcagggtt 3240
attgtctcat gagcggatac atatttgaat gtatttagaa aaataaacaa ataggggttc 3300
cgcgcacatt tccccgaaaa gtgccaccta aattgtaagc gttaatattt tgttaaaatt 3360
cgcgttaaat ttttgttaaa tcagctcatt ttttaaccaa taggccgaaa tcggcaaaat 3420
cccttataaa tcaaaagaat agaccgagat agggttgagt gttgttccag tttggaacaa 3480
gagtccacta ttaaagaacg tggactccaa cgtcaaaggg cgaaaaaccg tctatcaggg 3540
cgatggccca ctacgtgaac catcacccta atcaagtttt ttggggtcga ggtgccgtaa 3600
agcactaaat cggaacccta aagggagccc ccgatttaga gcttgacggg gaaagccggc 3660
gaacgtggcg agaaaggaag ggaagaaagc gaaaggagcg ggcgctaggg cgctggcaag 3720
tgtagcggtc acgctgcgcg taaccaccac acccgccgcg cttaatgcgc cgctacaggg 3780
cgcgtcccat tcgccattca ggctgcgcaa ctgttgggaa gggcgatcgg tgcgggcctc 3840
ttcgctatta cgccagctgg cgaaaggggg atgtgctgca aggcgattaa gttgggtaac 3900
gccagggttt tcccagtcac gacgttgtaa aacgacggcc agtgagcgcg cgtaatacga 3960
ctcactatag ggcgaattgg gtaccgggcc cataaatgag tagaaagcgc catatcggcg 4020
cttttctttt ggaagaaaat atagggaaaa tggtacttgt taaaaattcg gaatatttat 4080
acaatatcat atgtatcaca ttgaaaggag agcttaatta aagataatat ctttgaattg 4140
taacgcccct caaaagtaag aactacaaaa aaagaatacg ttatatagaa atatgtttga 4200
accttcttca gattacaaat atattcggac ggactctacc tcaaatgctt atctaactat 4260
agaatgacat acaagcacaa ccttgaaaat ttgaaaatat aactaccaat gaacttgttc 4320
atgtgaatta tcgctgtatt taattttctc aattcaatat ataatatgcc aatacattgt 4380
tacaagtaga aattaagaca cccttgatag ccttactata cctaacatga tgtagtatta 4440
aatgaatatg taaatatatt tatgataaga agcgacttat ttataatcat tacatatttt 4500

```
tctattggaa tgattaagat tccaatagaa tagtgtataa attatttatc ttgaaaggag   4560
ggatgcctaa aaacgaagaa cattaaaaac atatatttgc accgtctaat ggatttatga   4620
aaaatcattt tatcagtttg aaaattatgt attatggagc tctataaaaa tgaggaggga   4680
accgaatggc ttcaactgaa gacgtaatca aggagttcat gcgcttcaaa gtgcgaatgg   4740
aaggaagtgt aaacgggcat gagtttgaaa ttgaaggtga aggtgaagga aggccttatg   4800
aaggaacgca aactgcaaaa cttaaagtga caaaaggagg accgctgccg tttgcttggg   4860
acatcttaag tccgcagttt cagtatgggt caaaagttta tgtaaagcat cctgctgaca   4920
ttcctgatta caaaaagtta agttttcctg aaggattcaa gtgggagcgc gtaatgaact   4980
ttgaagatgg aggtgtcgta actgtaacgc aagattcaag tctacaagac ggttgcttca   5040
tttacaaagt aaagttcatt ggcgtgaact ttccaagtga tggtcctgta atgcagaaaa   5100
agacaatggg ttgggagccg tcaactgaga ggctttatcc gcgtgatggt gtcttgaaag   5160
gtgaaattca caaagcctta aagttgaaag atggagggca ttatcttgtt gagttcaaga   5220
gcatttacat ggcgaaaaag cctgtgcagc ttcctggcta ctactatgtt gattcaaaac   5280
ttgacataac tagtcacaac gaagactaca caattgttga gcagtatgag cgaactgaag   5340
gaaggcatca tctttttctt taagagacca gacttccaat tgacactaaa gggatccaga   5400
agcggcaaca cgctaatcaa taaaaaaacg ctgtgcggtt aaagggcaca gcgtttttttg   5460
tgtatgaatc gaaaaagagg agagatcgca ggccccccct cgaggtcgac ggtatcgata   5520
agcttgatat cgaattcctg cagcccgggg gatccttatt tgtatagttc atccatgcca   5580
tgtgtaatcc cagcagctgt tacaaactca agaaggatca tgtgatctct cttttcgttg   5640
ggatctttgg aaagggcaga ttgcgtggac aggtaatggt tgtctggtaa aaggacaggg   5700
ccatcgccaa ttggagtatt ttgttgataa tggtctgcta attgaacgct tccatcttta   5760
atgttgtgtc taattttgaa gttaactttg atgccattct ttggtttgtc tgccatgatg   5820
tatacattat gtgagttata attgtattcc attttgtgtc caagaatgtt tccatcttct   5880
ttaaaatcaa taccttttaa ctcgattcta ttaacaaggg tatcaccttc aaacttgact   5940
tcagcacgtg tcttgtagtt cccgtcatct ttgtaaaata tagttctttc ctgtacataa   6000
ccttcgggca tggcactctt gaaaaagtca tgctgtttca tatgatctgg gtatctagaa   6060
aagcattgaa caccataagt gagagtagtg acaagcgttg gccatggaac aggtagcttc   6120
ccagtagtgc aaataaattt aagggtaagt tttccgtatg ttgcatcacc ttcaccctct   6180
ccactaacag agaattttttg cccattaaca tcgccatcta attcaacaag aattgggaca   6240
actccagtga aaagttcttc tcctttactc atcgttggtt ccggcgttgg ttccggcgtt   6300
ggttccggtt gtacgccttg gccgcccatg ttctgctgtg cgaaagatac taaacgttta   6360
gtgatttctc ctccgacaga accgtttgca cgagaagttg tttctccgcc aaggtttacg   6420
ccgaactcag aagcaatttc gtatttcatt tggtcgattg cttgagcagc gccgggtact   6480
actagttggt ttgaagagtt gttgtttgcc atttgtatga tctcctttat aaagtagtat   6540
ggttgggttt gctggaattg caccagccga tgattttcgg aatgaaaacc attgccagct   6600
cggcttcacc caatgctgtt tgccgctttg tactacgtat tatggtgaat caaacggcat   6660
ctcattcgga aaacggtgtg gtaaatagcg gaaggaaaaa gaaaagccca gcctggtgcg   6720
gctgagcttt tagctttcag tcatatatgt gataaagcat taattcatgc agctctttta   6780
cgagagccgg ctcttctttt cccggatgtg tgtgtcccca ttcaatgtct ccggacttat   6840
```

```
ggtaaatccc ttcgtaatgc gtaccctgcc agtaaaatga aatccgccat ccgggcagtt   6900
tctctttttt gaataacggt ttccagctga agtgcgaaat catgacgttc acgctcctta   6960
tgggaaatgt tgatcttgtt cattgtagct catcgttcaa tgcctgtccc ggccttttttg  7020
aggtcttttt ttcttagatt tttggggtta tttaggggag aaaacatagg ggggtactac   7080
gacctccccc ctaggtgtcc attgtccatt gtccaaacaa ataaataaat attgggtttt   7140
taatgttaaa aggttgtttt ttatgttaaa gtgaaaaaaa cagatgttgg gaggtacagt   7200
gatggttgta gatagaaaag aagagaaaaa agttgctgtt actttaagac ttacaacaga   7260
agaaaatgag atattaaata gaatcaaaga aaaatataat attagcaaat cagatgcaac   7320
cggtattcta ataaaaaaat atgcaaagga ggaatacggt gcattttaaa caaaaaaaga   7380
tagacagcac tggcatgctg cctatctatg actaaatttt gttaaatgta ttagcaccgt   7440
tattatatca tgagcgaaaa tgtaataaaa gaaactgaaa acaagaaaaa ttcaagagga   7500
cgtaattgga catttgtttt atatccagaa tcagcaaaag ccgagtggtt agagtattta   7560
aaagagttac acattcaatt tgtagtgtct ccattacatg atagggatac tgatacagaa   7620
gataggatga aaaaagagca ttatcatatt ctagtgatgt atgagggtaa taaatcttat   7680
gaacagataa aaataattac agaagaattg aatgcgacta ttccgcagat tgcaggaagt   7740
gtgaaaggtc ttgtgagata tatgcttcac atggacgatc ctaataaatt taaatatcaa   7800
aaagaagata tgatagttta tggcggtgta gatgttgatg aattattaaa gaaaacaaca   7860
acagatagat ataaattaat taaagaaatg attgagttta ttgatgaaca aggaatcgta   7920
gaatttaaga gtttaatgga ttatgcaatg aagtttaaat ttgatgattg gttcccgctt   7980
ttatgtgata actcggcgta tgttattcaa gaatatataa aatcaaatcg gtataaatct   8040
gaccgataga ttttgaattt aggtgtcaca agacactctt ttttcgcacc aacgaaaact   8100
ggtttaagcc gactgcgcaa aagacataat cgattcacaa aaaataggca cacgaaaaac   8160
aagttaaggg atgcagttta tgcatccctt aacttactta ttaaataatt tatagctatt   8220
gaaaagagat aagaattgtt caaagctaat attgtttaaa tcgtcaattc ctgcatgttt   8280
taaggaattg ttaaattgat tttttgtaaa tattttcttg tattctttgt taacccattt   8340
cataacgaaa taattatact tttgtttatc tttgtgtgat attcttgatt tttttctact   8400
taatctgata agtgagctat tcactttagg tttaggatga aaatattctc ttggaaccat   8460
acttaatata gaaatatcaa cttctgccat taaaagtaat gccaatgagc gttttgtatt   8520
taataatctt ttagcaaacc cgtattccac gattaaataa atctcattag ctatactatc   8580
aaaaacaatt ttgcgtatta tatccgtact tatgttataa ggtatattac catatatttt   8640
ataggattgg tttttaggaa atttaaactg caatatatcc ttgtttaaaa cttggaaatt   8700
atcgtgatca acaagtttat tttctgtagt tttgcataat ttatggtcta tttcaatggc   8760
agttacgaaa ttacacctct ttactaattc aagggtaaaa tggccttttc ctgagccgat   8820
ttcaaagata ttatcatgtt catttaatct tatatttgtc attattttat ctatattatg   8880
ttttgaagta ataaagtttt gactgtgttt tatatttttc tcgttcatta taaccctctt   8940
taatttggtt atatgaattt tgcttattaa cgattcatta taaccactta tttttttgttt  9000
ggttgataat gaactgtgct gattacaaaa atactaaaaa tgcccatatt ttttcctcct   9060
tataaaatta gtataattat agcacgagct ctgataaata tgaacatgat gagtgatcgt   9120
taaatttata ctgcaa                                                   9136
```

<210> SEQ ID NO 8
<211> LENGTH: 9114
<212> TYPE: DNA
<213> ORGANISM: Artificial Sequence
<220> FEATURE:
<223> OTHER INFORMATION: Plasmid system

<400> SEQUENCE: 8
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420
ttcggtcaga tgcaattcga catgtggacg gactggttac aagtgataaa gatttctttg 480
atgatttaag cggagaagaa atagaacgat tttttaaaga tagcttggag tttctagagc 540
ggccgcatta ttaatctgtt cagcaatcgg gcgcgattgc tgaataaaag atacgagaga 600
cctctcttgt atcttttta ttttgagtgg ttttgtccgt tacactagaa aaccgaaaga 660
caataaaaat tttattcttg ctgagtctgg ctttcggtaa gctagacaaa acggacaaaa 720
taaaaattgg caagggttta aaggtggaga ttttttgagt gatcttctca aaaaatacta 780
cctgtccctt gctgattttt aaacgagcac gagagcaaaa cccccctttg ctgaggtggc 840
agagggcagg ttttttgtt tctttttct cgtaaaaaa agaaaggtct taaaggtttt 900
atggttttgg tcggcactgc cgacagcctc gcagagcaca cactttatga atataaagta 960
tagtgtgtta tactttactt ggaagtggtt gccggaaaga gcgaaaatgc ctcacatttg 1020
tgccacctaa aaaggagcga tttacatatg agttatgcag tttgtagaat gcaaaaagtg 1080
aaatcagctg gactaaaagg cagcggccgc caccgcggtg gagctccagc ttttgttccc 1140
tttagtgagg gttaattgcg cgcttggcgt aatcatggtc atagctgttt cctgtgtgaa 1200
attgttatcc gctcacaatt ccacacaaca tacgagccgg aagcataaag tgtaaagcct 1260
ggggtgccta atgagtgagc taactcacat taattgcgtt gcgctcactg cccgctttcc 1320
agtcgggaaa cctgtcgtgc cagctgcatt aatgaatcgg ccaacgcgcg gggagaggcg 1380
gtttgcgtat tgggcgctct tccgcttcct cgctcactga ctcgctgcgc tcggtcgttc 1440
ggctgcggcg agcggtatca gctcactcaa aggcggtaat acggttatcc acagaatcag 1500
gggataacgc aggaaagaac atgtgagcaa aaggccagca aaaggccagg aaccgtaaaa 1560
aggccgcgtt gctggcgttt ttccataggc tccgcccccc tgacgagcat cacaaaaatc 1620
gacgctcaag tcagaggtgg cgaaacccga caggactata aagataccag gcgtttcccc 1680
ctggaagctc cctcgtgcgc tctcctgttc cgaccctgcc gcttaccgga tacctgtccg 1740
cctttctccc ttcgggaagc gtggcgcttt ctcatagctc acgctgtagg tatctcagtt 1800
cggtgtaggt cgttcgctcc aagctgggct gtgtgcacga accccccgtt cagcccgacc 1860
gctgcgcctt atccggtaac tatcgtcttg agtccaaccc ggtaagacac gacttatcgc 1920
cactggcagc agccactggt aacaggatta gcagagcgag gtatgtaggc ggtgctacag 1980
agttcttgaa gtggtggcct aactacggct acactagaag aacagtattt ggtatctgcg 2040
ctctgctgaa gccagttacc ttcggaaaaa gagttggtag ctcttgatcc ggcaaacaaa 2100

```
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ctgctgtcca gactgtccgc tgtgtaaaaa   4020
aaaggaataa agggggttg acattatttt actgatatgt ataatataat ttgtataaga   4080
aaatggagag cttaattaaa gataatatct ttgaattgta acgcccctca aaagtaagaa   4140
ctacaaaaaa agaatacgtt atatagaaat atgtttgaac cttcttcaga ttacaaatat   4200
attcggacgg actctacctc aaatgcttat ctaactatag aatgacatac aagcacaacc   4260
ttgaaaattt gaaaatataa ctaccaatga acttgttcat gtgaattatc gctgtattta   4320
attttctcaa ttcaatatat aatatgccaa tacattgtta caagtagaaa ttaagacacc   4380
cttgatagcc ttactatacc taacatgatg tagtattaaa tgaatatgta aatatattta   4440
tgataagaag cgacttattt ataatcatta catatttttc tattggaatg attaagattc   4500
```

```
caatagaata gtgtataaat tatttatctt gaaaggaggg atgcctaaaa acgaagaaca   4560
ttaaaaacat atatttgcac cgtctaatgg atttatgaaa aatcatttta tcagtttgaa   4620
aattatgtat tatggagctc tataaaaatg aggagggaac cgaatggctt caactgaaga   4680
cgtaatcaag gagttcatgc gcttcaaagt gcgaatggaa ggaagtgtaa acgggcatga   4740
gtttgaaatt gaaggtgaag gtgaaggaag gccttatgaa ggaacgcaaa ctgcaaaact   4800
taaagtgaca aaaggaggac cgctgccgtt tgcttgggac atcttaagtc cgcagtttca   4860
gtatgggtca aaagtttatg taaagcatcc tgctgacatt cctgattaca aaaagttaag   4920
ttttcctgaa ggattcaagt gggagcgcgt aatgaacttt gaagatggag gtgtcgtaac   4980
tgtaacgcaa gattcaagtc tacaagacgg ttgcttcatt tacaaagtaa agttcattgg   5040
cgtgaacttt ccaagtgatg gtcctgtaat gcagaaaaag acaatgggtt gggagccgtc   5100
aactgagagg ctttatccgc gtgatggtgt cttgaaaggt gaaattcaca aagccttaaa   5160
gttgaaagat ggagggcatt atcttgttga gttcaagagc atttacatgg cgaaaaagcc   5220
tgtgcagctt cctggctact actatgttga ttcaaaactt gacataacta gtcacaacga   5280
agactacaca attgttgagc agtatgagcg aactgaagga aggcatcatc tttttcttta   5340
agagaccaga cttccaattg acactaaagg gatccagaag cggcaacacg ctaatcaata   5400
aaaaaacgct gtgcggttaa agggcacagc gttttttgtg tatgaatcga aaaagaggag   5460
agatcgcagg cccccccctcg aggtcgacgg tatcgataag cttgatatcg aattcctgca   5520
gcccggggga tccttatttg tatagttcat ccatgccatg tgtaatccca gcagctgtta   5580
caaactcaag aaggatcatg tgatctctct tttcgttggg atctttggaa agggcagatt   5640
gcgtggacag gtaatggttg tctggtaaaa ggacagggcc atcgccaatt ggagtatttt   5700
gttgataatg gtctgctaat tgaacgcttc catctttaat gttgtgtcta attttgaagt   5760
taactttgat gccattcttt ggtttgtctg ccatgatgta tacattatgt gagttataat   5820
tgtattccat tttgtgtcca agaatgtttc catcttcttt aaaatcaata ccttttaact   5880
cgattctatt aacaagggta tcaccttcaa acttgacttc agcacgtgtc ttgtagttcc   5940
cgtcatcttt gtaaaatata gttctttcct gtacataacc ttcgggcatg gcactcttga   6000
aaaagtcatg ctgtttcata tgatctgggt atctagaaaa gcattgaaca ccataagtga   6060
gagtagtgac aagcgttggc catggaacag gtagcttccc agtagtgcaa ataaatttaa   6120
gggtaagttt tccgtatgtt gcatcacctt caccctctcc actaacagag aatttttgcc   6180
cattaacatc gccatctaat tcaacaagaa ttgggacaac tccagtgaaa agttcttctc   6240
ctttactcat cgttggttcc ggcgttggtt ccggcgttgg ttccggttgt acgccttggc   6300
cgcccatgtt ctgctgtgcg aaagatacta aacgtttagt gatttctcct ccgacagaac   6360
cgtttgcacg agaagttgtt tctccgccaa ggtttacgcc gaactcagaa gcaatttcgt   6420
atttcatttg gtcgattgct tgagcagcgc cgggtactac tagttggttt gaagagttgt   6480
tgtttgccat ttgtatgatc tcctttataa agtagtatgg ttgggtttgc tggaattgca   6540
ccagccgatg attttcggaa tgaaaaccat tgccagctcg gcttcaccca atgctgtttg   6600
ccgctttgta ctacgtatta tggtgaatca aacggcatct cattcggaaa acggtgtggt   6660
aaatagcgga aggaaaaaga aaagcccagc ctggtgcggc tgagctttta gctttcagtc   6720
atatatgtga taaagcatta attcatgcag ctcttttacg agagccggct cttcttttcc   6780
cggatgtgtg tgtccccatt caatgtctcc ggacttatgg taaatccctt cgtaatgcgt   6840
```

```
accctgccag taaaatgaaa tccgccatcc gggcagtttc tctttttga ataacggttt   6900
ccagctgaag tgcgaaatca tgacgttcac gctccttatg ggaaatgttg atcttgttca   6960
ttgtagctca tcgttcaatg cctgtcccgg cctttttgag gtcttttttt cttagatttt   7020
tggggttatt taggggagaa aacatagggg ggtactacga cctccccct aggtgtccat   7080
tgtccattgt ccaaacaaat aaataaatat tgggttttta atgttaaaag gttgtttttt   7140
atgttaaagt gaaaaaaaca gatgttggga ggtacagtga tggttgtaga tagaaaagaa   7200
gagaaaaaag ttgctgttac tttaagactt acaacagaag aaaatgagat attaaataga   7260
atcaaagaaa aatataatat tagcaaatca gatgcaaccg gtattctaat aaaaaaatat   7320
gcaaaggagg aatacggtgc attttaaaca aaaaaagata gacagcactg gcatgctgcc   7380
tatctatgac taaattttgt taaatgtatt agcaccgtta ttatatcatg agcgaaaatg   7440
taataaaaga aactgaaaac aagaaaaatt caagaggacg taattggaca tttgttttat   7500
atccagaatc agcaaaagcc gagtggttag agtatttaaa agagttacac attcaatttg   7560
tagtgtctcc attacatgat agggatactg atacagaaga taggatgaaa aaagagcatt   7620
atcatattct agtgatgtat gagggtaata aatcttatga acagataaaa ataattacag   7680
aagaattgaa tgcgactatt ccgcagattg caggaagtgt gaaaggtctt gtgagatata   7740
tgcttcacat ggacgatcct aataaattta aatatcaaaa agaagatatg atagtttatg   7800
gcggtgtaga tgttgatgaa ttattaaaga aaacaacaac agatagatat aaattaatta   7860
aagaaatgat tgagtttatt gatgaacaag gaatcgtaga atttaagagt ttaatggatt   7920
atgcaatgaa gtttaaattt gatgattggt tcccgctttt atgtgataac tcggcgtatg   7980
ttattcaaga atatataaaa tcaaatcggt ataaatctga ccgatagatt ttgaatttag   8040
gtgtcacaag acactctttt ttcgcaccaa cgaaaactgg tttaagccga ctgcgcaaaa   8100
gacataatcg attcacaaaa aataggcaca cgaaaaacaa gttaagggat gcagtttatg   8160
catcccttaa cttacttatt aaataattta tagctattga aaagagataa gaattgttca   8220
aagctaatat tgtttaaatc gtcaattcct gcatgtttta aggaattgtt aaattgattt   8280
tttgtaaata ttttcttgta ttctttgtta acccatttca taacgaaata attatacttt   8340
tgtttatctt tgtgtgatat tcttgatttt tttctactta atctgataag tgagctattc   8400
actttaggtt taggatgaaa atattctctt ggaaccatac ttaatataga aatatcaact   8460
tctgccatta aaagtaatgc caatgagcgt tttgtattta ataatctttt agcaaacccg   8520
tattccacga ttaaataaat ctcattagct atactatcaa aaacaatttt gcgtattata   8580
tccgtactta tgttataagg tatattacca tatattttat aggattggtt tttaggaaat   8640
ttaaactgca atatatcctt gtttaaaact tggaaattat cgtgatcaac aagtttattt   8700
tctgtagttt tgcataattt atggtctatt tcaatggcag ttacgaaatt acacctcttt   8760
actaattcaa gggtaaaatg gccttttcct gagccgattt caaagatatt atcatgttca   8820
tttaatctta tatttgtcat tattttatct atattatgtt ttgaagtaat aaagttttga   8880
ctgtgtttta tatttttctc gttcattata accctcttta atttggttat atgaattttg   8940
cttattaacg attcattata accacttatt ttttgtttgg ttgataatga actgtgctga   9000
ttacaaaaat actaaaaatg cccatatttt ttcctcctta taaaattagt ataattatag   9060
cacgagctct gataaatatg aacatgatga gtgatcgtta aatttatact gcaa         9114
```

<210> SEQ ID NO 9
<211> LENGTH: 8542

<212> TYPE: DNA
<213> ORGANISM: Artificial Sequence
<220> FEATURE:
<223> OTHER INFORMATION: Plasmid system

<400> SEQUENCE: 9

```
tcggatgcga ttattgaata aaagatatga gagatttatc taatttcttt tttcttgtaa     60
aaaaagaaag ttcttaaagg ttttatagtt ttggtcgtag agcacacggt ttaacgactt    120
aattacgaag taaataagtc tagtgtgtta gactttatga aatctatata cgtttatata    180
tatttattat ccggaggtgt agcatgtctc attcaatttt gagggttgcc agagttaaag    240
gatcaagtaa tacaaacggg atacaaagac ataatcaaag agagaataaa aactataata    300
ataaagacat aaatcatgag gaaacatata aaaattatga tttgattaac gcacaaaata    360
taaagtataa agataaaatt gatgaaacga ttgatgagaa ttattcaggg aaacgtaaaa    420
ttcggtcaga tgcaattcga catgtggacg gactggttac aagtgataaa gatttctttg    480
atgatttaag cggagaagaa atagaacgat tttttaaaga tagcttggag tttctagagc    540
ggccgcatta ttaatctgtt cagcaatcgg gcgcgattgc tgaataaaag atacgagaga    600
cctctcttgt atctttttta ttttgagtgg ttttgtccgt tacactagaa aaccgaaaga    660
caataaaaat tttattcttg ctgagtctgg ctttcggtaa gctagacaaa acggacaaaa    720
taaaaattgg caagggttta aaggtggaga tttttgagt gatcttctca aaaaatacta     780
cctgtccctt gctgattttt aaacgagcac gagagcaaaa cccccctttg ctgaggtggc    840
agagggcagg ttttttgtt tctttttct cgtaaaaaa agaaaggtct taaaggtttt      900
atggttttgg tcggcactgc cgacagcctc gcagagcaca cactttatga atataaagta    960
tagtgtgtta tactttactt ggaagtggtt gccggaaaga gcgaaaatgc ctcacatttg   1020
tgccacctaa aaaggagcga tttacatatg agttatgcag tttgtagaat gcaaaaagtg   1080
aaatcagctg gactaaaagg cagcggccgc caccgcggtg gagctccagc ttttgttccc   1140
tttagtgagg gttaattgcg cgcttggcgt aatcatggtc atagctgttt cctgtgtgaa   1200
attgttatcc gctcacaatt ccacacaaca tacgagccgg aagcataaag tgtaaagcct   1260
ggggtgccta atgagtgagc taactcacat taattgcgtt gcgctcactg cccgctttcc   1320
agtcgggaaa cctgtcgtgc cagctgcatt aatgaatcgg ccaacgcgcg gggagaggcg   1380
gtttgcgtat tgggcgctct tccgcttcct cgctcactga ctcgctgcgc tcggtcgttc   1440
ggctgcggcg agcggtatca gctcactcaa aggcggtaat acggttatcc acagaatcag   1500
gggataacgc aggaaagaac atgtgagcaa aaggccagca aaaggccagg aaccgtaaaa   1560
aggccgcgtt gctggcgttt ttccataggc tccgcccccc tgacgagcat cacaaaaatc   1620
gacgctcaag tcagaggtgg cgaaacccga caggactata aagataccag gcgtttcccc   1680
ctggaagctc cctcgtgcgc tctcctgttc cgaccctgcc gcttaccgga tacctgtccg   1740
cctttctccc ttcgggaagc gtggcgcttt ctcatagctc acgctgtagg tatctcagtt   1800
cggtgtaggt cgttcgctcc aagctgggct gtgtgcacga accccccgtt cagcccgacc   1860
gctgcgcctt atccggtaac tatcgtcttg agtccaaccc ggtaagacac gacttatcgc   1920
cactggcagc agccactggt aacaggatta gcagagcgag gtatgtaggc ggtgctacag   1980
agttcttgaa gtggtggcct aactacggct acactagaag aacagtattt ggtatctgcg   2040
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
```

```
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ccgtaagatg aaaccttaga taaaagtgct   4020
tttttgttg caattgaaga attattaatg ttaagcttaa ttgagctcta taaaaatgag   4080
gagggaaccg aatggcttca actgaagacg taatcaagga gttcatgcgc ttcaaagtgc   4140
gaatggaagg aagtgtaaac gggcatgagt ttgaaattga aggtgaaggt gaaggaaggc   4200
cttatgaagg aacgcaaact gcaaaactta aagtgacaaa aggaggaccg ctgccgtttg   4260
cttgggacat cttaagtccg cagtttcagt atgggtcaaa agtttatgta aagcatcctg   4320
ctgacattcc tgattacaaa aagttaagtt ttcctgaagg attcaagtgg gagcgcgtaa   4380
tgaactttga agatggaggt gtcgtaactg taacgcaaga ttcaagtcta caagacggtt   4440
gcttcattta caaagtaaag ttcattggcg tgaactttcc aagtgatggt cctgtaatgc   4500
agaaaaagac aatgggttgg gagccgtcaa ctgagaggct ttatccgcgt gatggtgtct   4560
```

```
tgaaaggtga aattcacaaa gccttaaagt tgaaagatgg agggcattat cttgttgagt   4620
tcaagagcat ttacatggcg aaaaagcctg tgcagcttcc tggctactac tatgttgatt   4680
caaaacttga cataactagt cacaacgaag actacacaat tgttgagcag tatgagcgaa   4740
ctgaaggaag gcatcatctt tttctttaag agaccagact tccaattgac actaaaggga   4800
tccagaagcg gcaacacgct aatcaataaa aaaacgctgt gcggttaaag ggcacagcgt   4860
tttttgtgta tgaatcgaaa aagaggagag atcgcaggcc ccccctcgag gtcgacggta   4920
tcgataagct tgatatcgaa ttcctgcagc ccgggggatc cttatttgta tagttcatcc   4980
atgccatgtg taatcccagc agctgttaca aactcaagaa ggatcatgtg atctctcttt   5040
tcgttgggat ctttggaaag ggcagattgc gtggacaggt aatggttgtc tggtaaaagg   5100
acagggccat cgccaattgg agtattttgt tgataatggt ctgctaattg aacgcttcca   5160
tctttaatgt tgtgtctaat tttgaagtta actttgatgc cattctttgg tttgtctgcc   5220
atgatgtata cattatgtga gttataattg tattccattt tgtgtccaag aatgtttcca   5280
tcttctttaa aatcaatacc ttttaactcg attctattaa caagggtatc accttcaaac   5340
ttgacttcag cacgtgtctt gtagttcccg tcatctttgt aaaatatagt tctttcctgt   5400
acataacctt cgggcatggc actcttgaaa aagtcatgct gtttcatatg atctgggtat   5460
ctagaaaagc attgaacacc ataagtgaga gtagtgacaa gcgttggcca tggaacaggt   5520
agcttcccag tagtgcaaat aaatttaagg gtaagttttc cgtatgttgc atcaccttca   5580
ccctctccac taacagagaa tttttgccca ttaacatcgc catctaattc aacaagaatt   5640
gggacaactc cagtgaaaag ttcttctcct ttactcatcg ttggttccgg cgttggttcc   5700
ggcgttggtt ccggttgtac gccttggccg cccatgttct gctgtgcgaa agatactaaa   5760
cgtttagtga tttctcctcc gacagaaccg tttgcacgag aagttgtttc tccgccaagg   5820
tttacgccga actcagaagc aatttcgtat ttcatttggt cgattgcttg agcagcgccg   5880
ggtactacta gttggtttga agagttgttg tttgccattt gtatgatctc ctttataaag   5940
tagtatggtt gggtttgctg gaattgcacc agccgatgat tttcggaatg aaaaccattg   6000
ccagctcggc ttcacccaat gctgtttgcc gctttgtact acgtattatg gtgaatcaaa   6060
cggcatctca ttcggaaaac ggtgtggtaa atagcggaag gaaaaagaaa agcccagcct   6120
ggtgcggctg agcttttagc tttcagtcat atatgtgata aagcattaat tcatgcagct   6180
cttttacgag agccggctct tcttttcccg gatgtgtgtg tccccattca atgtctccgg   6240
acttatggta aatcccttcg taatgcgtac cctgccagta aaatgaaatc cgccatccgg   6300
gcagtttctc ttttttgaat aacggtttcc agctgaagtg cgaaatcatg acgttcacgc   6360
tccttatggg aaatgttgat cttgttcatt gtagctcatc gttcaatgcc tgtcccggcc   6420
tttttgaggt cttttttttct tagatttttg gggttattta ggggagaaaa catagggggg   6480
tactacgacc tcccccctag gtgtccattg tccattgtcc aaacaaataa ataaatattg   6540
ggtttttaat gttaaaaggt tgttttttat gttaaagtga aaaaaacaga tgttgggagg   6600
tacagtgatg gttgtagata gaaaagaaga gaaaaaagtt gctgttactt taagacttac   6660
aacagaagaa aatgagatat taaatagaat caaagaaaaa tataatatta gcaaatcaga   6720
tgcaaccggt attctaataa aaaaatatgc aaaggaggaa tacggtgcat tttaaacaaa   6780
aaaagataga cagcactggc atgctgccta tctatgacta aattttgtta aatgtattag   6840
caccgttatt atatcatgag cgaaaatgta ataaaagaaa ctgaaaacaa gaaaaattca   6900
```

agaggacgta attggacatt tgttttatat ccagaatcag caaaagccga gtggttagag 6960
tatttaaaag agttacacat tcaatttgta gtgtctccat tacatgatag ggatactgat 7020
acagaagata ggatgaaaaa agagcattat catattctag tgatgtatga gggtaataaa 7080
tcttatgaac agataaaaat aattacagaa gaattgaatg cgactattcc gcagattgca 7140
ggaagtgtga aaggtcttgt gagatatatg cttcacatgg acgatcctaa taaatttaaa 7200
tatcaaaaag aagatatgat agtttatggc ggtgtagatg ttgatgaatt attaaagaaa 7260
acaacaacag atagatataa attaattaaa gaaatgattg agtttattga tgaacaagga 7320
atcgtagaat ttaagagttt aatggattat gcaatgaagt ttaaatttga tgattggttc 7380
ccgcttttat gtgataactc ggcgtatgtt attcaagaat atataaaatc aaatcggtat 7440
aaatctgacc gatagatttt gaatttaggt gtcacaagac actctttttt cgcaccaacg 7500
aaaactggtt taagccgact gcgcaaaaga cataatcgat tcacaaaaaa taggcacacg 7560
aaaaacaagt taagggatgc agtttatgca tcccttaact tacttattaa ataatttata 7620
gctattgaaa agagataaga attgttcaaa gctaatattg tttaaatcgt caattcctgc 7680
atgttttaag gaattgttaa attgattttt tgtaaatatt ttcttgtatt ctttgttaac 7740
ccatttcata acgaaataat tatacttttg tttatctttg tgtgatattc ttgatttttt 7800
tctacttaat ctgataagtg agctattcac tttaggttta ggatgaaaat attctcttgg 7860
aaccatactt aatatagaaa tatcaacttc tgccattaaa agtaatgcca atgagcgttt 7920
tgtatttaat aatcttttag caaacccgta ttccacgatt aaataaatct cattagctat 7980
actatcaaaa acaattttgc gtattatatc cgtacttatg ttataaggta tattaccata 8040
tattttatag gattggtttt taggaaattt aaactgcaat atatccttgt ttaaaacttg 8100
gaaattatcg tgatcaacaa gtttattttc tgtagttttg cataatttat ggtctatttc 8160
aatggcagtt acgaaattac acctctttac taattcaagg gtaaaatggc cttttcctga 8220
gccgatttca aagatattat catgttcatt taatcttata tttgtcatta ttttatctat 8280
attatgtttt gaagtaataa agttttgact gtgttttata tttttctcgt tcattataac 8340
cctctttaat ttggttatat gaattttgct tattaacgat tcattataac cacttatttt 8400
ttgtttggtt gataatgaac tgtgctgatt acaaaaatac taaaaatgcc catatttttt 8460
cctccttata aaattagtat aattatagca cgagctctga taaatatgaa catgatgagt 8520
gatcgttaaa tttatactgc aa 8542

<210> SEQ ID NO 10
<211> LENGTH: 8589
<212> TYPE: DNA
<213> ORGANISM: Artificial Sequence
<220> FEATURE:
<223> OTHER INFORMATION: Plasmid system

<400> SEQUENCE: 10
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420

```
ttcggtcaga tgcaattcga catgtggacg gactggttac aagtgataaa gatttctttg    480
atgatttaag cggagaagaa atagaacgat tttttaaaga tagcttggag tttctagagc    540
ggccgcatta ttaatctgtt cagcaatcgg gcgcgattgc tgaataaaag atacgagaga    600
cctctcttgt atcttttta ttttgagtgg ttttgtccgt tacactagaa aaccgaaaga    660
caataaaaat tttattcttg ctgagtctgg ctttcggtaa gctagacaaa acggacaaaa    720
taaaaattgg caagggttta aaggtggaga ttttttgagt gatcttctca aaaaatacta    780
cctgtccctt gctgattttt aaacgagcac gagagcaaaa cccccctttg ctgaggtggc    840
agagggcagg tttttttgtt tctttttttct cgtaaaaaaa agaaaggtct taaaggtttt    900
atggttttgg tcggcactgc cgacagcctc gcagagcaca cactttatga atataaagta    960
tagtgtgtta tactttactt ggaagtggtt gccggaaaga gcgaaaatgc ctcacatttg   1020
tgccacctaa aaaggagcga tttacatatg agttatgcag tttgtagaat gcaaaaagtg   1080
aaatcagctg gactaaaagg cagcggccgc caccgcggtg gagctccagc ttttgttccc   1140
tttagtgagg gttaattgcg cgcttggcgt aatcatggtc atagctgttt cctgtgtgaa   1200
attgttatcc gctcacaatt ccacacaaca tacgagccgg aagcataaag tgtaaagcct   1260
ggggtgccta atgagtgagc taactcacat taattgcgtt gcgctcactg cccgctttcc   1320
agtcgggaaa cctgtcgtgc cagctgcatt aatgaatcgg ccaacgcgcg gggagaggcg   1380
gtttgcgtat tgggcgctct tccgcttcct cgctcactga ctcgctgcgc tcggtcgttc   1440
ggctgcggcg agcggtatca gctcactcaa aggcggtaat acggttatcc acagaatcag   1500
gggataacgc aggaaagaac atgtgagcaa aaggccagca aaaggccagg aaccgtaaaa   1560
aggccgcgtt gctggcgttt ttccataggc tccgcccccc tgacgagcat cacaaaaatc   1620
gacgctcaag tcagaggtgg cgaaacccga caggactata aagataccag gcgtttcccc   1680
ctggaagctc cctcgtgcgc tctcctgttc cgaccctgcc gcttaccgga tacctgtccg   1740
cctttctccc ttcgggaagc gtggcgcttt ctcatagctc acgctgtagg tatctcagtt   1800
cggtgtaggt cgttcgctcc aagctgggct gtgtgcacga accccccgtt cagcccgacc   1860
gctgcgcctt atccggtaac tatcgtcttg agtccaaccc ggtaagacac gacttatcgc   1920
cactggcagc agccactggt aacaggatta gcagagcgag gtatgtaggc ggtgctacag   1980
agttcttgaa gtggtggcct aactacggct acactagaag aacagtattt ggtatctgcg   2040
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
```

```
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc cataaatgag tagaaagcgc catatcggcg   4020
cttttctttt ggaagaaaat atagggaaaa tggtacttgt taaaaattcg gaatatttat   4080
acaatatcat atgtatcaca ttgaaaggag agctctataa aaatgaggag ggaaccgaat   4140
ggcttcaact gaagacgtaa tcaaggagtt catgcgcttc aaagtgcgaa tggaaggaag   4200
tgtaaacggg catgagtttg aaattgaagg tgaaggtgaa ggaaggcctt atgaaggaac   4260
gcaaactgca aaacttaaag tgacaaaagg aggaccgctg ccgtttgctt gggacatctt   4320
aagtccgcag tttcagtatg ggtcaaaagt ttatgtaaag catcctgctg acattcctga   4380
ttacaaaaag ttaagttttc ctgaaggatt caagtgggag cgcgtaatga actttgaaga   4440
tggaggtgtc gtaactgtaa cgcaagattc aagtctacaa gacggttgct tcatttacaa   4500
agtaaagttc attggcgtga actttccaag tgatggtcct gtaatgcaga aaaagacaat   4560
gggttgggag ccgtcaactg agaggcttta tccgcgtgat ggtgtcttga aaggtgaaat   4620
tcacaaagcc ttaaagttga aagatggagg gcattatctt gttgagttca agagcattta   4680
catggcgaaa aagcctgtgc agcttcctgg ctactactat gttgattcaa aacttgacat   4740
aactagtcac aacgaagact acacaattgt tgagcagtat gagcgaactg aaggaaggca   4800
tcatcttttt ctttaagaga ccagacttcc aattgacact aaagggatcc agaagcggca   4860
acacgctaat caataaaaaa acgctgtgcg gttaaagggc acagcgtttt ttgtgtatga   4920
atcgaaaaag aggagagatc gcaggccccc cctcgaggtc gacggtatcg ataagcttga   4980
tatcgaattc ctgcagcccg ggggatcctt atttgtatag ttcatccatg ccatgtgtaa   5040
tcccagcagc tgttacaaac tcaagaagga tcatgtgatc tctcttttcg ttgggatctt   5100
tggaaagggc agattgcgtg gacaggtaat ggttgtctgg taaaaggaca gggccatcgc   5160
```

caattggagt attttgttga taatggtctg ctaattgaac gcttccatct ttaatgttgt 5220
gtctaatttt gaagttaact ttgatgccat tctttggttt gtctgccatg atgtatacat 5280
tatgtgagtt ataattgtat tccattttgt gtccaagaat gtttccatct tctttaaaat 5340
caataccttt taactcgatt ctattaacaa gggtatcacc ttcaaacttg acttcagcac 5400
gtgtcttgta gttcccgtca tctttgtaaa atatagttct ttcctgtaca taaccttcgg 5460
gcatggcact cttgaaaaag tcatgctgtt tcatatgatc tgggtatcta gaaaagcatt 5520
gaacaccata agtgagagta gtgacaagcg ttggccatgg aacaggtagc ttcccagtag 5580
tgcaaataaa tttaagggta agttttccgt atgttgcatc accttcaccc tctccactaa 5640
cagagaattt ttgcccatta acatcgccat ctaattcaac aagaattggg acaactccag 5700
tgaaaagttc ttctccttta ctcatcgttg gttccggcgt tggttccggc gttggttccg 5760
gttgtacgcc ttggccgccc atgttctgct gtgcgaaaga tactaaacgt ttagtgattt 5820
ctcctccgac agaaccgttt gcacgagaag ttgtttctcc gccaaggttt acgccgaact 5880
cagaagcaat ttcgtatttc atttggtcga ttgcttgagc agcgccgggt actactagtt 5940
ggtttgaaga gttgttgttt gccatttgta tgatctcctt tataaagtag tatggttggg 6000
tttgctggaa ttgcaccagc cgatgatttt cggaatgaaa accattgcca gctcggcttc 6060
acccaatgct gtttgccgct ttgtactacg tattatggtg aatcaaacgg catctcattc 6120
ggaaaacggt gtggtaaata gcggaaggaa aaagaaaagc ccagcctggt gcggctgagc 6180
ttttagcttt cagtcatata tgtgataaag cattaattca tgcagctctt ttacgagagc 6240
cggctcttct tttcccggat gtgtgtgtcc ccattcaatg tctccggact tatggtaaat 6300
cccttcgtaa tgcgtaccct gccagtaaaa tgaaatccgc catccgggca gtttctcttt 6360
tttgaataac ggtttccagc tgaagtgcga aatcatgacg ttcacgctcc ttatgggaaa 6420
tgttgatctt gttcattgta gctcatcgtt caatgcctgt cccggccttt ttgaggtctt 6480
tttttcttag atttttgggg ttatttaggg gagaaaacat aggggggtac tacgacctcc 6540
cccctaggtg tccattgtcc attgtccaaa caaataaata aatattgggt ttttaatgtt 6600
aaaaggttgt tttttatgtt aaagtgaaaa aaacagatgt tgggaggtac agtgatggtt 6660
gtagatagaa aagaagagaa aaaagttgct gttactttaa gacttacaac agaagaaaat 6720
gagatattaa atagaatcaa agaaaaatat aatattagca aatcagatgc aaccggtatt 6780
ctaataaaaa aatatgcaaa ggaggaatac ggtgcatttt aaacaaaaaa agatagacag 6840
cactggcatg ctgcctatct atgactaaat tttgttaaat gtattagcac cgttattata 6900
tcatgagcga aaatgtaata aaagaaactg aaaacaagaa aaattcaaga ggacgtaatt 6960
ggacatttgt tttatatcca gaatcagcaa aagccgagtg gttagagtat ttaaaagagt 7020
tacacattca atttgtagtg tctccattac atgataggga tactgataca gaagatagga 7080
tgaaaaaaga gcattatcat attctagtga tgtatgaggg taataaatct tatgaacaga 7140
taaaaataat tacagaagaa ttgaatgcga ctattccgca gattgcagga agtgtgaaag 7200
gtcttgtgag atatatgctt cacatggacg atcctaataa atttaaatat caaaaagaag 7260
atatgatagt ttatggcggt gtagatgttg atgaattatt aaagaaaaca acaacagata 7320
gatataaatt aattaaagaa atgattgagt ttattgatga acaaggaatc gtagaattta 7380
agagtttaat ggattatgca atgaagttta aatttgatga ttggttcccg cttttatgtg 7440
ataactcggc gtatgttatt caagaatata taaaatcaaa tcggtataaa tctgaccgat 7500
agattttgaa tttaggtgtc acaagacact ctttttcgc accaacgaaa actggtttaa 7560
gccgactgcg caaaagacat aatcgattca caaaaaatag gcacacgaaa aacaagttaa 7620
gggatgcagt ttatgcatcc cttaacttac ttattaaata atttatagct attgaaaaga 7680
gataagaatt gttcaaagct aatattgttt aaatcgtcaa ttcctgcatg ttttaaggaa 7740
ttgttaaatt gatttttgt aaatatttc ttgtattctt tgttaaccca tttcataacg 7800
aaataattat actttgttt atctttgtgt gatattcttg attttttct acttaatctg 7860 ataagtgagc tattcacttt aggtttagga tgaaaatatt ctcttggaac catacttaat 7920
atagaaatat caacttctgc cattaaaagt aatgccaatg agcgttttgt atttaataat 7980
cttttagcaa acccgtattc cacgattaaa taaatctcat tagctatact atcaaaaaca 8040
attttgcgta ttatatccgt acttatgtta taaggtatat taccatatat tttataggat 8100
tggtttttag gaaatttaaa ctgcaatata tccttgttta aaacttggaa attatcgtga 8160
tcaacaagtt tattttctgt agttttgcat aatttatggt ctatttcaat ggcagttacg 8220
aaattacacc tctttactaa ttcaagggta aaatggcctt ttcctgagcc gatttcaaag 8280
atattatcat gttcatttaa tcttatattt gtcattattt tatctatatt atgttttgaa 8340
gtaataaagt tttgactgtg ttttatattt ttctcgttca ttataaccct ctttaatttg 8400
gttatatgaa ttttgcttat taacgattca ttataaccac ttattttttg tttggttgat 8460
aatgaactgt gctgattaca aaaatactaa aaatgcccat attttttcct ccttataaaa 8520
ttagtataat tatagcacga gctctgataa atatgaacat gatgagtgat cgttaaattt 8580
atactgcaa 8589

<210> SEQ ID NO 11
<211> LENGTH: 8567
<212> TYPE: DNA
<213> ORGANISM: Artificial Sequence
<220> FEATURE:
<223> OTHER INFORMATION: Plasmid system

<400> SEQUENCE: 11
tcggatgcga ttattgaata aaagatatga gagatttatc taatttcttt tttcttgtaa 60
aaaaagaaag ttcttaaagg ttttatagtt ttggtcgtag agcacacggt ttaacgactt 120
aattacgaag taaataagtc tagtgtgtta gactttatga aatctatata cgtttatata 180
tatttattat ccggaggtgt agcatgtctc attcaatttt gagggttgcc agagttaaag 240
gatcaagtaa tacaaacggg atacaaagac ataatcaaag agagaataaa aactataata 300
ataaagacat aaatcatgag gaaacatata aaaattatga tttgattaac gcacaaaata 360
taaagtataa agataaaatt gatgaaacga ttgatgagaa ttattcaggg aaacgtaaaa 420
ttcggtcaga tgcaattcga catgtggacg gactggttac aagtgataaa gatttctttg 480
atgatttaag cggagaagaa atagaacgat tttttaaaga tagcttggag tttctagagc 540
ggccgcatta ttaatctgtt cagcaatcgg gcgcgattgc tgaataaaag atacgagaga 600
cctctcttgt atcttttta ttttgagtgg ttttgtccgt tacactagaa aaccgaaaga 660
caataaaaat tttattcttg ctgagtctgg ctttcggtaa gctagacaaa acggacaaaa 720
taaaaattgg caagggttta aaggtggaga ttttttgagt gatcttctca aaaaatacta 780
cctgtccctt gctgattttt aaacgagcac gagagcaaaa ccccccttg ctgaggtggc 840 agagggcagg ttttttgtt tcttttttct cgtaaaaaaa agaaaggtct taaaggtttt 900
atggttttgg tcggcactgc cgacagcctc gcagagcaca cactttatga atataaagta 960

```
tagtgtgtta tactttactt ggaagtggtt gccggaaaga gcgaaaatgc ctcacatttg   1020
tgccacctaa aaaggagcga tttacatatg agttatgcag tttgtagaat gcaaaaagtg   1080
aaatcagctg gactaaaagg cagcggccgc caccgcggtg gagctccagc ttttgttccc   1140
tttagtgagg gttaattgcg cgcttggcgt aatcatggtc atagctgttt cctgtgtgaa   1200
attgttatcc gctcacaatt ccacacaaca tacgagccgg aagcataaag tgtaaagcct   1260
ggggtgccta atgagtgagc taactcacat taattgcgtt gcgctcactg cccgctttcc   1320
agtcgggaaa cctgtcgtgc cagctgcatt aatgaatcgg ccaacgcgcg gggagaggcg   1380
gtttgcgtat tgggcgctct tccgcttcct cgctcactga ctcgctgcgc tcggtcgttc   1440
ggctgcggcg agcggtatca gctcactcaa aggcggtaat acggttatcc acagaatcag   1500
gggataacgc aggaaagaac atgtgagcaa aaggccagca aaaggccagg aaccgtaaaa   1560
aggccgcgtt gctggcgttt ttccataggc tccgcccccc tgacgagcat cacaaaaatc   1620
gacgctcaag tcagaggtgg cgaaacccga caggactata aagataccag gcgtttcccc   1680
ctggaagctc cctcgtgcgc tctcctgttc cgaccctgcc gcttaccgga tacctgtccg   1740
cctttctccc ttcgggaagc gtggcgcttt ctcatagctc acgctgtagg tatctcagtt   1800
cggtgtaggt cgttcgctcc aagctgggct gtgtgcacga accccccgtt cagcccgacc   1860
gctgcgcctt atccggtaac tatcgtcttg agtccaaccc ggtaagacac gacttatcgc   1920
cactggcagc agccactggt aacaggatta gcagagcgag gtatgtaggc ggtgctacag   1980
agttcttgaa gtggtggcct aactacggct acactagaag aacagtattt ggtatctgcg   2040
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
```

-continued

```
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
gccagggttt tcccagtcac gacgttgtaa aacgacggcc agtgagcgcg cgtaatacga   3960
ctcactatag ggcgaattgg gtaccgggcc ctgctgtcca gactgtccgc tgtgtaaaaa   4020
aaaggaataa agggggggttg acattatttt actgatatgt ataatataat ttgtataaga   4080
aaatggagag ctctataaaa atgaggaggg aaccgaatgg cttcaactga agacgtaatc   4140
aaggagttca tgcgcttcaa agtgcgaatg gaaggaagtg taaacgggca tgagtttgaa   4200
attgaaggtg aaggtgaagg aaggccttat gaaggaacgc aaactgcaaa acttaaagtg   4260
acaaaaggag gaccgctgcc gtttgcttgg gacatcttaa gtccgcagtt tcagtatggg   4320
tcaaaagttt atgtaaagca tcctgctgac attcctgatt acaaaaagtt aagttttcct   4380
gaaggattca agtgggagcg cgtaatgaac tttgaagatg gaggtgtcgt aactgtaacg   4440
caagattcaa gtctacaaga cggttgcttc atttacaaag taaagttcat tggcgtgaac   4500
tttccaagtg atggtcctgt aatgcagaaa aagacaatgg gttgggagcc gtcaactgag   4560
aggctttatc cgcgtgatgg tgtcttgaaa ggtgaaattc acaaagcctt aaagttgaaa   4620
gatggagggc attatcttgt tgagttcaag agcatttaca tggcgaaaaa gcctgtgcag   4680
cttcctggct actactatgt tgattcaaaa cttgacataa ctagtcacaa cgaagactac   4740
acaattgttg agcagtatga gcgaactgaa ggaaggcatc atctttttct ttaagagacc   4800
agacttccaa ttgacactaa agggatccag aagcggcaac acgctaatca ataaaaaaac   4860
gctgtgcggt taaagggcac agcgtttttt gtgtatgaat cgaaaaagag gagagatcgc   4920
aggccccccc tcgaggtcga cggtatcgat aagcttgata tcgaattcct gcagcccggg   4980
ggatccttat ttgtatagtt catccatgcc atgtgtaatc ccagcagctg ttacaaactc   5040
aagaaggatc atgtgatctc tcttttcgtt gggatctttg gaaagggcag attgcgtgga   5100
caggtaatgg ttgtctggta aaaggacagg gccatcgcca attggagtat tttgttgata   5160
atggtctgct aattgaacgc ttccatcttt aatgttgtgt ctaattttga agttaacttt   5220
gatgccattc tttggtttgt ctgccatgat gtatacatta tgtgagttat aattgtattc   5280
cattttgtgt ccaagaatgt ttccatcttc tttaaaatca atacctttta actcgattct   5340
attaacaagg gtatcacctt caaacttgac ttcagcacgt gtcttgtagt tcccgtcatc   5400
tttgtaaaat atagttcttt cctgtacata accttcgggc atggcactct tgaaaaagtc   5460
atgctgtttc atatgatctg ggtatctaga aaagcattga acaccataag tgagagtagt   5520
gacaagcgtt ggccatggaa caggtagctt cccagtagtg caaataaatt taagggtaag   5580
ttttccgtat gttgcatcac cttcaccctc tccactaaca gagaattttt gcccattaac   5640
atcgccatct aattcaacaa gaattgggac aactccagtg aaaagttctt ctcctttact   5700
```

```
catcgttggt tccggcgttg gttccggcgt tggttccggt tgtacgcctt ggccgcccat   5760
gttctgctgt gcgaaagata ctaaacgttt agtgatttct cctccgacag aaccgtttgc   5820
acgagaagtt gtttctccgc caaggtttac gccgaactca gaagcaattt cgtatttcat   5880
ttggtcgatt gcttgagcag cgccgggtac tactagttgg tttgaagagt tgttgtttgc   5940
catttgtatg atctccttta taaagtagta tggttgggtt tgctggaatt gcaccagccg   6000
atgattttcg gaatgaaaac cattgccagc tcggcttcac ccaatgctgt ttgccgcttt   6060
gtactacgta ttatggtgaa tcaaacggca tctcattcgg aaaacggtgt ggtaaatagc   6120
ggaaggaaaa agaaaagccc agcctggtgc ggctgagctt ttagctttca gtcatatatg   6180
tgataaagca ttaattcatg cagctctttt acgagagccg gctcttcttt tcccggatgt   6240
gtgtgtcccc attcaatgtc tccggactta tggtaaatcc cttcgtaatg cgtaccctgc   6300
cagtaaaatg aaatccgcca tccgggcagt ttctcttttt tgaataacgg tttccagctg   6360
aagtgcgaaa tcatgacgtt cacgctcctt atgggaaatg ttgatcttgt tcattgtagc   6420
tcatcgttca atgcctgtcc cggccttttt gaggtctttt tttcttagat ttttggggtt   6480
atttagggga gaaaacatag gggggtacta cgacctcccc cctaggtgtc cattgtccat   6540
tgtccaaaca aataaataaa tattgggttt ttaatgttaa aaggttgttt tttatgttaa   6600
agtgaaaaaa acagatgttg ggaggtacag tgatggttgt agatagaaaa gaagagaaaa   6660
aagttgctgt tactttaaga cttacaacag aagaaaatga gatattaaat agaatcaaag   6720
aaaaatataa tattagcaaa tcagatgcaa ccggtattct aataaaaaaa tatgcaaagg   6780
aggaatacgg tgcattttaa acaaaaaaag atagacagca ctggcatgct gcctatctat   6840
gactaaattt tgttaaatgt attagcaccg ttattatatc atgagcgaaa atgtaataaa   6900
agaaactgaa aacaagaaaa attcaagagg acgtaattgg acatttgttt tatatccaga   6960
atcagcaaaa gccgagtggt tagagtattt aaaagagtta cacattcaat ttgtagtgtc   7020
tccattacat gatagggata ctgatacaga agataggatg aaaaaagagc attatcatat   7080
tctagtgatg tatgagggta ataaatctta tgaacagata aaaataatta cagaagaatt   7140
gaatgcgact attccgcaga ttgcaggaag tgtgaaaggt cttgtgagat atatgcttca   7200
catggacgat cctaataaat ttaaatatca aaaagaagat atgatagttt atggcggtgt   7260
agatgttgat gaattattaa agaaaacaac aacagataga tataaattaa ttaaagaaat   7320
gattgagttt attgatgaac aaggaatcgt agaatttaag agtttaatgg attatgcaat   7380
gaagtttaaa tttgatgatt ggttcccgct tttatgtgat aactcggcgt atgttattca   7440
agaatatata aaatcaaatc ggtataaatc tgaccgatag attttgaatt taggtgtcac   7500
aagacactct tttttcgcac caacgaaaac tggtttaagc cgactgcgca aaagacataa   7560
tcgattcaca aaaaataggc acacgaaaaa caagttaagg gatgcagttt atgcatccct   7620
taacttactt attaaataat ttatagctat tgaaaagaga taagaattgt tcaaagctaa   7680
tattgtttaa atcgtcaatt cctgcatgtt ttaaggaatt gttaaattga ttttttgtaa   7740
atattttctt gtattctttg ttaacccatt tcataacgaa ataattatac ttttgtttat   7800
ctttgtgtga tattcttgat ttttttctac ttaatctgat aagtgagcta ttcactttag   7860
gtttaggatg aaaatattct cttggaacca tacttaatat agaaatatca acttctgcca   7920
ttaaaagtaa tgccaatgag cgttttgtat ttaataatct tttagcaaac ccgtattcca   7980
cgattaaata aatctcatta gctatactat caaaaacaat tttgcgtatt atatccgtac   8040
```

```
ttatgttata aggtatatta ccatatattt tataggattg gtttttagga aatttaaact   8100

gcaatatatc cttgtttaaa acttggaaat tatcgtgatc aacaagttta ttttctgtag   8160

ttttgcataa tttatggtct atttcaatgg cagttacgaa attacacctc tttactaatt   8220

caagggtaaa atggcctttt cctgagccga tttcaaagat attatcatgt tcatttaatc   8280

ttatatttgt cattatttta tctatattat gttttgaagt aataaagttt tgactgtgtt   8340

ttatattttt ctcgttcatt ataaccctct ttaatttggt tatatgaatt ttgcttatta   8400

acgattcatt ataaccactt attttttgtt tggttgataa tgaactgtgc tgattacaaa   8460

aatactaaaa atgcccatat tttttcctcc ttataaaatt agtataatta tagcacgagc   8520

tctgataaat atgaacatga tgagtgatcg ttaaatttat actgcaa                 8567
```

<210> SEQ ID NO 12
<211> LENGTH: 7593
<212> TYPE: DNA
<213> ORGANISM: Artificial Sequence
<220> FEATURE:
<223> OTHER INFORMATION: Plasmid system

<400> SEQUENCE: 12

```
tcggatgcga ttattgaata aaagatatga gagatttatc taatttcttt tttcttgtaa     60

aaaaagaaag ttcttaaagg ttttatagtt ttggtcgtag agcacacggt ttaacgactt    120

aattacgaag taaataagtc tagtgtgtta gactttatga aatctatata cgtttatata    180

tatttattat ccggaggtgt agcatgtctc attcaatttt gagggttgcc agagttaaag    240

gatcaagtaa tacaaacggg atacaaagac ataatcaaag agagaataaa aactataata    300

ataaagacat aaatcatgag gaaacatata aaaattatga tttgattaac gcacaaaata    360

taaagtataa agataaaatt gatgaaacga ttgatgagaa ttattcaggg aaacgtaaaa    420

ttcggtcaga tgcaattcga catgtggacg gactggttac aagtgataaa gatttctttg    480

atgatttaag cggagaagaa atagaacgat tttttaaaga tagcttggag tttctagagc    540

ggccgcatta ttaatctgtt cagcaatcgg gcgcgattgc tgaataaaag atacgagaga    600

cctctcttgt atcttttta ttttgagtgg ttttgtccgt tacactagaa aaccgaaaga    660

caataaaaat tttattcttg ctgagtctgg ctttcggtaa gctagacaaa acggacaaaa    720

taaaaattgg caagggttta aaggtggaga ttttttgagt gatcttctca aaaaatacta    780

cctgtccctt gctgattttt aaacgagcac gagagcaaaa cccccctttg ctgaggtggc    840

agagggcagg tttttttgtt tctttttct cgtaaaaaaa agaaaggtct taaaggtttt    900

atggttttgg tcggcactgc cgacagcctc gcagagcaca cactttatga atataaagta    960

tagtgtgtta tactttactt ggaagtggtt gccggaaaga gcgaaaatgc ctcacatttg   1020

tgccacctaa aaaggagcga tttacatatg agttatgcag tttgtagaat gcaaaaagtg   1080

aaatcagctg gactaaaagg cagcggccgc caccgcggtg gagctccagc ttttgttccc   1140

tttagtgagg gttaattgcg cgcttggcgt aatcatggtc atagctgttt cctgtgtgaa   1200

attgttatcc gctcacaatt ccacacaaca tacgagccgg aagcataaag tgtaaagcct   1260

ggggtgccta atgagtgagc taactcacat taattgcgtt gcgctcactg cccgctttcc   1320

agtcgggaaa cctgtcgtgc cagctgcatt aatgaatcgg ccaacgcgcg gggagaggcg   1380

gtttgcgtat tgggcgctct tccgcttcct cgctcactga ctcgctgcgc tcggtcgttc   1440

ggctgcggcg agcggtatca gctcactcaa aggcggtaat acggttatcc acagaatcag   1500

gggataacgc aggaaagaac atgtgagcaa aaggccagca aaaggccagg aaccgtaaaa   1560
```

```
aggccgcgtt gctggcgttt ttccataggc tccgcccccc tgacgagcat cacaaaaatc   1620
gacgctcaag tcagaggtgg cgaaacccga caggactata aagataccag gcgtttcccc   1680
ctggaagctc cctcgtgcgc tctcctgttc cgaccctgcc gcttaccgga tacctgtccg   1740
cctttctccc ttcgggaagc gtggcgcttt ctcatagctc acgctgtagg tatctcagtt   1800
cggtgtaggt cgttcgctcc aagctgggct gtgtgcacga accccccgtt cagcccgacc   1860
gctgcgcctt atccggtaac tatcgtcttg agtccaaccc ggtaagacac gacttatcgc   1920
cactggcagc agccactggt aacaggatta gcagagcgag gtatgtaggc ggtgctacag   1980
agttcttgaa gtggtggcct aactacggct acactagaag aacagtattt ggtatctgcg   2040
ctctgctgaa gccagttacc ttcggaaaaa gagttggtag ctcttgatcc ggcaaacaaa   2100
ccaccgctgg tagcggtggt ttttttgttt gcaagcagca gattacgcgc agaaaaaaag   2160
gatctcaaga agatcctttg atcttttcta cggggtctga cgctcagtgg aacgaaaact   2220
cacgttaagg gattttggtc atgagattat caaaaaggat cttcacctag atccttttaa   2280
attaaaaatg aagttttaaa tcaatctaaa gtatatatga gtaaacttgg tctgacagtt   2340
accaatgctt aatcagtgag gcacctatct cagcgatctg tctatttcgt tcatccatag   2400
ttgcctgact ccccgtcgtg tagataacta cgatacggga gggcttacca tctggcccca   2460
gtgctgcaat gataccgcga gacccacgct caccggctcc agatttatca gcaataaacc   2520
agccagccgg aagggccgag cgcagaagtg gtcctgcaac tttatccgcc tccatccagt   2580
ctattaattg ttgccgggaa gctagagtaa gtagttcgcc agttaatagt ttgcgcaacg   2640
ttgttgccat tgctacaggc atcgtggtgt cacgctcgtc gtttggtatg gcttcattca   2700
gctccggttc ccaacgatca aggcgagtta catgatcccc catgttgtgc aaaaaagcgg   2760
ttagctcctt cggtcctccg atcgttgtca gaagtaagtt ggccgcagtg ttatcactca   2820
tggttatggc agcactgcat aattctctta ctgtcatgcc atccgtaaga tgcttttctg   2880
tgactggtga gtactcaacc aagtcattct gagaatagtg tatgcggcga ccgagttgct   2940
cttgcccggc gtcaatacgg gataataccg cgccacatag cagaacttta aaagtgctca   3000
tcattggaaa acgttcttcg gggcgaaaac tctcaaggat cttaccgctg ttgagatcca   3060
gttcgatgta acccactcgt gcacccaact gatcttcagc atcttttact ttcaccagcg   3120
tttctgggtg agcaaaaaca ggaaggcaaa atgccgcaaa aaagggaata agggcgacac   3180
ggaaatgttg aatactcata ctcttccttt ttcaatatta ttgaagcatt tatcagggtt   3240
attgtctcat gagcggatac atatttgaat gtatttagaa aaataaacaa ataggggttc   3300
cgcgcacatt tccccgaaaa gtgccaccta aattgtaagc gttaatattt tgttaaaatt   3360
cgcgttaaat ttttgttaaa tcagctcatt ttttaaccaa taggccgaaa tcggcaaaat   3420
cccttataaa tcaaaagaat agaccgagat agggttgagt gttgttccag tttggaacaa   3480
gagtccacta ttaaagaacg tggactccaa cgtcaaaggg cgaaaaaccg tctatcaggg   3540
cgatggccca ctacgtgaac catcacccta atcaagtttt ttggggtcga ggtgccgtaa   3600
agcactaaat cggaacccta aagggagccc ccgatttaga gcttgacggg gaaagccggc   3660
gaacgtggcg agaaaggaag ggaagaaagc gaaaggagcg ggcgctaggg cgctggcaag   3720
tgtagcggtc acgctgcgcg taaccaccac acccgccgcg cttaatgcgc cgctacaggg   3780
cgcgtcccat tcgccattca ggctgcgcaa ctgttgggaa gggcgatcgg tgcgggcctc   3840
ttcgctatta cgccagctgg cgaaaggggg atgtgctgca aggcgattaa gttgggtaac   3900
```

gccagggttt tcccagtcac gacgttgtaa aacgacggcc agtgagcgcg cgtaatacga 3960
ctcactatag ggcgaattgg gtaccgggcc ccccctcgag gtcgacggta tcgataagct 4020
tgatatcgaa ttcctgcagc ccgggggatc cttaaagaaa aagatgatgc cttccttcag 4080
ttcgctcata ctgctcaaca attgtgtagt cttcgttgtg actagttatg tcaagttttg 4140
aatcaacata gtagtagcca ggaagctgca caggcttttt cgccatgtaa atgctcttga 4200
actcaacaag ataatgccct ccatctttca actttaaggc tttgtgaatt tcacctttca 4260
agacaccatc acgcggataa agcctctcag ttgacggctc ccaacccatt gtctttttct 4320
gcattacagg accatcactt ggaaagttca cgccaatgaa ctttactttg taaatgaagc 4380
aaccgtcttg cagacttgaa tcttgcgtta cagttacgac acctccatct tcaaagttca 4440
ttacgcgctc ccacttgaat ccttcaggaa aacttaactt tttgtaatca ggaatgtcag 4500
caggatgctt tacataaact tttgacccat actgaaactg cggacttaag atgtcccaag 4560
caaacggcag cggtcctcct tttgtcactt taagttttgc agtttgcgtt ccttcataag 4620
gccttccttc accttcacct tcaatttcaa actcatgccc gtttacactt ccttccattc 4680
gcactttgaa gcgcatgaac tctttgatta cgtcttcagt tgaagccatc gttggttccg 4740
gggttggttc cggagttggt tccggttgta cgccttggcc gcccatgttc tgctgtgcga 4800
aagatactaa acgtttagtg atttctcctc cgacagaacc gtttgcacga gaagttgttt 4860
ctccgccaag gtttacgccg aactcagaag caatttcgta tttcatttgg tcgattgctt 4920
gagcagcgcc gggtactact agttggtttg aagagttgtt gtttgccatt tgtatgatct 4980
cctttataaa gtagtatggt tgggtttgct ggaattgcac cagccgatga ttttcggaat 5040
gaaaaccatt gccagctcgg cttcacccaa tgctgtttgc cgctttgtac tacgtattat 5100
ggtgaatcaa acggcatctc attcggaaaa cggtgtggta aatagcggaa ggaaaaagaa 5160
aagcccagcc tggtgcggct gagcttttag ctttcagtca tatatgtgat aaagcattaa 5220
ttcatgcagc tcttttacga gagccggctc ttcttttccc ggatgtgtgt gtccccattc 5280
aatgtctccg gacttatggt aaatcccttc gtaatgcgta ccctgccagt aaaatgaaat 5340
ccgccatccg ggcagtttct ctttttttgaa taacggtttc cagctgaagt gcgaaatcat 5400
gacgttcacg ctccttatgg gaaatgttga tcttgttcat tgtagctcat cgttcaatgc 5460
ctgtcccggc ctttttgagg tctttttttc ttagattttt ggggttattt aggggagaaa 5520
acataggggg gtactacgac ctccccccta ggtgtccatt gtccattgtc caaacaaata 5580
aataaatatt gggtttttaa tgttaaaagg ttgtttttta tgttaaagtg aaaaaaacag 5640
atgttgggag gtacagtgat ggttgtagat agaaaagaag agaaaaaagt tgctgttact 5700
ttaagactta caacagaaga aaatgagata ttaaatagaa tcaaagaaaa atataatatt 5760
agcaaatcag atgcaaccgg tattctaata aaaaaatatg caaaggagga atacggtgca 5820
ttttaaacaa aaaaagatag acagcactgg catgctgcct atctatgact aaattttgtt 5880
aaatgtatta gcaccgttat tatatcatga gcgaaaatgt aataaaagaa actgaaaaca 5940
agaaaaattc aagaggacgt aattggacat ttgttttata tccagaatca gcaaaagccg 6000
agtggttaga gtatttaaaa gagttacaca ttcaatttgt agtgtctcca ttacatgata 6060
gggatactga tacagaagat aggatgaaaa aagagcatta tcatattcta gtgatgtatg 6120
agggtaataa atcttatgaa cagataaaaa taattacaga agaattgaat gcgactattc 6180
cgcagattgc aggaagtgtg aaaggtcttg tgagatatat gcttcacatg gacgatccta 6240
ataaatttaa atatcaaaaa gaagatatga tagtttatgg cggtgtagat gttgatgaat 6300
tattaaagaa aacaacaaca gatagatata aattaattaa agaaatgatt gagtttattg 6360
atgaacaagg aatcgtagaa tttaagagtt taatggatta tgcaatgaag tttaaatttg 6420
atgattggtt cccgctttta tgtgataact cggcgtatgt tattcaagaa tatataaaat 6480
caaatcggta taaatctgac cgatagattt tgaatttagg tgtcacaaga cactcttttt 6540
tcgcaccaac gaaaactggt ttaagccgac tgcgcaaaag acataatcga ttcacaaaaa 6600
ataggcacac gaaaaacaag ttaagggatg cagtttatgc atcccttaac ttacttatta 6660
aataatttat agctattgaa aagagataag aattgttcaa agctaatatt gtttaaatcg 6720
tcaattcctg catgttttaa ggaattgtta aattgatttt ttgtaaatat tttcttgtat 6780
tctttgttaa cccatttcat aacgaaataa ttatactttt gtttatcttt gtgtgatatt 6840
cttgattttt ttctacttaa tctgataagt gagctattca ctttaggttt aggatgaaaa 6900
tattctcttg gaaccatact taatatagaa atatcaactt ctgccattaa aagtaatgcc 6960
aatgagcgtt ttgtatttaa taatctttta gcaaacccgt attccacgat taaataaatc 7020
tcattagcta tactatcaaa aacaattttg cgtattatat ccgtacttat gttataaggt 7080
atattaccat atattttata ggattggttt ttaggaaatt taaactgcaa tatatccttg 7140
tttaaaactt ggaaattatc gtgatcaaca agtttatttt ctgtagtttt gcataattta 7200
tggtctattt caatggcagt tacgaaatta cacctcttta ctaattcaag ggtaaaatgg 7260
ccttttcctg agccgatttc aaagatatta tcatgttcat ttaatcttat atttgtcatt 7320
attttatcta tattatgttt tgaagtaata aagttttgac tgtgttttat atttttctcg 7380
ttcattataa ccctctttaa tttggttata tgaattttgc ttattaacga ttcattataa 7440
ccacttattt tttgtttggt tgataatgaa ctgtgctgat tacaaaaata ctaaaaatgc 7500
ccatattttt tcctccttat aaaattagta taattatagc acgagctctg ataaatatga 7560
acatgatgag tgatcgttaa atttatactg caa 7593

<210> SEQ ID NO 13
<211> LENGTH: 8819
<212> TYPE: DNA
<213> ORGANISM: Artificial Sequence
<220> FEATURE:
<223> OTHER INFORMATION: Plasmid system

<400> SEQUENCE: 13
ctagagcggc cgccaccgcg gtggagctcc agcttttgtt ccctttagtg agggttaatt 60
gcgcgcttgg cgtacgcaga tgctgctgaa gagattatta aaaagctgaa agcaaaaggc 120
tatcaattgg taactgtatc tcagcttgaa gaagtgaaga agcagagagg ctattgaata 180
aatgagtaga aagcgccata tcggcgcttt tcttttggaa gaaaatatag ggaaaatggt 240
acttgttaaa aattcggaat atttatacaa tatcatatgt atcacattga aaggaggggc 300
ctgctgtcca gactgtccgc tgtgtaaaaa aaaggaataa aggggggttg acattatttt 360
actgatatgt ataatataat ttgtataaga aaatggaggg gccctcgaaa cgtaagatga 420
aaccttagat aaaagtgctt tttttgttgc aattgaagaa ttattaatgt taagcttaat 480
taaagataat atctttgaat tgtaacgccc ctcaaaagta agaactacaa aaaaagaata 540
cgttatatag aaatatgttt gaaccttctt cagattacaa atatattcgg acggactcta 600
cctcaaatgc ttatctaact atagaatgac atacaagcac aaccttgaaa atttgaaaat 660
ataactacca atgaacttgt tcatgtgaat tatcgctgta tttaattttc tcaattcaat 720

-continued

```
atataatatg ccaatacatt gttacaagta gaaattaaga cacccttgat agccttacta    780
tacctaacat gatgtagtat taaatgaata tgtaaatata tttatgataa gaagcgactt    840
atttataatc attacatatt tttctattgg aatgattaag attccaatag aatagtgtat    900
aaattattta tcttgaaagg agggatggct aaaaacgaag aacattaaaa acatatattt    960
gcaccgtcta atggatttat gaaaaatcat tttatcagtt tgaaaattat gtattatgga   1020
gctcttataa aaatgaggag ggaaccgaat ggcttcaact gaagacgtaa tcaaagagtt   1080
catgcgcttc aaagtgcgaa tggaaggaag tgtaaacggg catgagtttg aaattgaagg   1140
tgaaggtgaa ggaaggcctt atgaaggaac gcaaactgca aaacttaaag tgacaaaagg   1200
aggaccgctg ccgtttgctt gggacatctt aagtccgcag tttcagtatg ggtcaaaagt   1260
ttatgtaaag catcctgctg acattcctga ttacaaaaag ttaagttttc ctgaaggatt   1320
caagtgggag cgcgtaatga actttgaaga tggaggtgtc gtaactgtaa cgcaagattc   1380
aagtctgcaa gacggttgct tcatttacaa agtaaagttc attggcgtga actttccaag   1440
tgatggtcct gtaatgcaga aaaagacaat gggttgggag ccgtcaactg agaggcttta   1500
tccgcgtgat ggtgtcttga aaggtgaaat tcacaaagcc ttaaagttga aagatggagg   1560
gcattatctt gttgagttca agagcattta catggcgaaa aagcctgtgc agcttcctgg   1620
ctactactat gttgattcaa aacttgacat aactagtcac aacgaagact acacaattgt   1680
tgagcagtat gagcgaactg aaggaaggca tcatcttttt ctttaagaga ccagacttcc   1740
aattgacact aaagggatcc agaagcggca acacgctaat caataaaaaa acgctgtgcg   1800
gttaaagggc acagcgtttt ttgtgtatga atcgaaaaag aggagagatc gcactgataa   1860
ttgccaacac aattaacatc tcaatcaagg taaatgctag cgcggccgcg tcgacaggcc   1920
tctttgatta cattttataa ttaattttaa caaagtgtca tcagccctca ggaagatcat   1980
ggtcatagct gtttcctgtg tgaaattgtt atccgctcac aattccacac aacatacgag   2040
ccggaagcat aaagtgtaaa gcctggggtg cctaatgagt gagctaactc acattaattg   2100
cgttgcgctc actgcccgct ttccagtcgg gaaacctgtc gtgccagctg cattaatgaa   2160
tcggccaacg cgcggggaga ggcggtttgc gtattgggcg ctcttccgct tcctcgctca   2220
ctgactcgct gcgctcggtc gttcggctgc ggcgagcggt atcagctcac tcaaaggcgg   2280
taatacggtt atccacagaa tcaggggata acgcaggaaa gaacatgtga gcaaaaggcc   2340
agcaaaaggc caggaaccgt aaaaaggccg cgttgctggc gtttttccat aggctccgcc   2400
cccctgacga gcatcacaaa aatcgacgct caagtcagag gtggcgaaac ccgacaggac   2460
tataaagata ccaggcgttt ccccctggaa gctccctcgt gcgctctcct gttccgaccc   2520
tgccgcttac cggatacctg tccgcctttc tcccttcggg aagcgtggcg ctttctcata   2580
gctcacgctg taggtatctc agttcggtgt aggtcgttcg ctccaagctg ggctgtgtgc   2640
acgaaccccc cgttcagccc gaccgctgcg ccttatccgg taactatcgt cttgagtcca   2700
acccggtaag acacgactta tcgccactgg cagcagccac tggtaacagg attagcagag   2760
cgaggtatgt aggcggtgct acagagttct tgaagtggtg gcctaactac ggctacacta   2820
gaagaacagt atttggtatc tgcgctctgc tgaagccagt taccttcgga aaaagagttg   2880
gtagctcttg atccggcaaa caaaccaccg ctggtagcgg tggttttttt gtttgcaagc   2940
agcagattac gcgcagaaaa aaaggatctc aagaagatcc tttgatcttt tctacggggt   3000
ctgacgctca gtggaacgaa aactcacgtt aagggatttt ggtcatgaga ttatcaaaaa   3060
ggatcttcac ctagatcctt ttaaattaaa aatgaagttt taaatcaatc taaagtatat   3120
```

```
atgagtaaac ttggtctgac agttaccaat gcttaatcag tgaggcacct atctcagcga   3180

tctgtctatt tcgttcatcc atagttgcct gactccccgt cgtgtagata actacgatac   3240

gggagggctt accatctggc cccagtgctg caatgatacc gcgagaccca cgctcaccgg   3300

ctccagattt atcagcaata aaccagccag ccggaagggc cgagcgcaga agtggtcctg   3360

caactttatc cgcctccatc cagtctatta attgttgccg ggaagctaga gtaagtagtt   3420

cgccagttaa tagtttgcgc aacgttgttg ccattgctac aggcatcgtg gtgtcacgct   3480

cgtcgtttgg tatggcttca ttcagctccg gttcccaacg atcaaggcga gttacatgat   3540

cccccatgtt gtgcaaaaaa gcggttagct ccttcggtcc tccgatcgtt gtcagaagta   3600

agttggccgc agtgttatca ctcatggtta tggcagcact gcataattct cttactgtca   3660

tgccatccgt aagatgcttt tctgtgactg gtgagtactc aaccaagtca ttctgagaat   3720

agtgtatgcg gcgaccgagt tgctcttgcc cggcgtcaat acgggataat accgcgccac   3780

atagcagaac tttaaaagtg ctcatcattg gaaaacgttc ttcggggcga aaactctcaa   3840

ggatcttacc gctgttgaga tccagttcga tgtaacccac tcgtgcaccc aactgatctt   3900

cagcatcttt tactttcacc agcgtttctg ggtgagcaaa aacaggaagg caaaatgccg   3960

caaaaaaggg aataagggcg acacggaaat gttgaatact catactcttc ctttttcaat   4020

attattgaag catttatcag ggttattgtc tcatgagcgg atacatattt gaatgtattt   4080

agaaaaataa acaaataggg gttccgcgca catttccccg aaaagtgcca cctaaattgt   4140

aagcgttaat attttgttaa aattcgcgtt aaatttttgt taaatcagct cattttttaa   4200

ccaataggcc gaaatcggca aaatccctta taaatcaaaa gaatagaccg agatagggtt   4260

gagtgttgtt ccagtttgga acaagagtcc actattaaag aacgtggact ccaacgtcaa   4320

agggcgaaaa accgtctatc agggcgatgg cccactacgt gaaccatcac cctaatcaag   4380

ttttttgggg tcgaggtgcc gtaaagcact aaatcggaac cctaaaggga gcccccgatt   4440

tagagcttga cggggaaagc cggcgaacgt ggcgagaaag gaagggaaga aagcgaaagg   4500

agcgggcgct agggcgctgg caagtgtagc ggtcacgctg cgcgtaacca ccacacccgc   4560

cgcgcttaat gcgccgctac agggcgcgtc ccattcgcca ttcaggctgc gcaactgttg   4620

ggaagggcga tcggtgcggg cctcttcgct attacgccag ctggcgaaag ggggatgtgc   4680

tgcaaggcga ttaagttggg taacgccagg gttttcccag tcacgacgtt gtaaaacgac   4740

ggccagtgag cgcgcgtaat acgactcact atagggcgaa ttgggtaccg ggcccccccct   4800

cgaggtcgac ggtatcgata agctcatgac catggcataa ccctgcttcg ggtcattat   4860

agcgattttt tcggtatatc catccttttt cgcacgatat acaggatttt gccaaagggt   4920

tcgtgtagac tttccttggt gtatccaacg gcgtcagccg ggcaggatag gtgaagtagg   4980

cccacccgcg agcgggtgtt ccttcttcac tgtcccttat tcgcacctgg cggtgctcaa   5040

cgggaatcct gttgatatcg aattcctgca gcccgggga tccactagtt ctagaaaatg   5100

aatacggtaa ggaaaatatg ctgtatgcga ctgtccatct ggatgaaaga gtcccacata   5160

tgcactttgg ttttgtccct ttaacagagg acgggagatt gtctgcaaaa gaacagttag   5220

gcaacaagaa agactttact caattacaag atagatttaa tgagtatgtg aatgagaaag   5280

gttatgaact tgaaagaggc acgtccaaag aggttacaga acgagaacat aaagcgatgg   5340

atcagtacaa gaaagatact gtatttcata aacaggaact gcaagaagtt aaggatgagt   5400

tacagaaggc aaataagcag ttacagagtg gaatagagca tatgaggtct acgaaaccct   5460
```

ttgattatga aaatgagcgt acaggtttgt tctctggacg tgaagagact ggtagaaaga 5520
tattaactgc tgatgaattt gaacgcctgc aagaaacaat ctcttctgca gaacggattg 5580
ttgatgatta cgaaaatatt aagagcacag actattacac agaaaatcaa gaattaaaaa 5640
aacgtagaga gagtttgaaa gaagtagtga atacatggaa agaggggtat cacgaaaaaa 5700
gtaaagaggt taataaatta aagcgagaga atgatagttt gaatgagcag ttgaatgtat 5760
cagagaaatt tcaagatagt acagtgactt tatatcgtgc tgcgagggcg aatttccctg 5820
ggtttgagaa agggtttaat aggcttaaag agaaattctt taatgattcc aaattcgagc 5880
gtgtgggaca gtttatggat gttgtacagg ataatgtcca gaaggtcgat agaaagcgtg 5940
agaaacagcg tacagacgat ttagagatgt agaggtactt ttatgccgag aaaacttttt 6000
gcgtgtgaca gtccttaaaa tatacttaga gcgtaagcga aagtagtagc gacagctatt 6060
aactttcggt tgcaaagctc taggattttt aatggacgca gcgcatcaca cgcaaaaagg 6120
aaattggaat aaatgcgaaa tttgagatgt taattaaaga ccttttgag gtcttttttt 6180
cttagatttt tggggttatt taggggagaa aacatagggg ggtactacga cctccccct 6240
aggtgtccat tgtccattgt ccaaacaaat aaataaatat tgggttttta atgttaaaag 6300
gttgtttttt atgttaaagt gaaaaaaaca gatgttggga ggtacagtga tggttgtaga 6360
tagaaaagaa gagaaaaaag ttgctgttac tttaagactt acaacagaag aaaatgagat 6420
attaaataga atcaaagaaa aatataatat tagcaaatca gatgcaaccg gtattctaat 6480
aaaaaaatat gcaaaggagg aatacggtgc attttaaaca aaaaaagata gacagcactg 6540
gcatgctgcc tatctatgac taaattttgt taaatgtatt agcaccgtta ttatatcatg 6600
agcgaaaatg taataaaaga aactgaaaac aagaaaaatt caagaggacg taattggaca 6660
tttgttttat atccagaatc agcaaaagcc gagtggttag agtatttaaa agagttacac 6720
attcaatttg tagtgtctcc attacatgat agggatactg atacagaaga taggatgaaa 6780
aaagagcatt atcatattct agtgatgtat gagggtaata aatcttatga acagataaaa 6840
ataattacag aagaattgaa tgcgactatt ccgcagattg caggaagtgt gaaaggtctt 6900
gtgagatata tgcttcacat ggacgatcct aataaattta aatatcaaaa agaagatatg 6960
atagtttatg gcggtgtaga tgttgatgaa ttattaaaga aaacaacaac agatagatat 7020
aaattaatta aagaaatgat tgagtttatt gatgaacaag gaatcgtaga atttaagagt 7080
ttaatggatt atgcaatgaa gtttaaattt gatgattggt tcccgctttt atgtgataac 7140
tcggcgtatg ttattcaaga atatataaaa tcaaatcggt ataaatctga ccgatagatt 7200
ttgaatttaa gagtgtcaca agacactctt ttttcgcacc aacgaaaact ggtttaagcc 7260
gactgcgcaa aagacataat cgattcacaa aaaataggca cacgaaaaac aagttaaggg 7320
atgcagttta tgcatccctt aacttactta ttaaataatt tatagctatt gaaaagagat 7380
aagaattgtt caaagctaat attgtttaaa tcgtcaattc ctgcatgttt taaggaattg 7440
ttaaattgat tttttgtaaa tattttcttg tattctttgt taacccattt cataacgaaa 7500
taattatact tttgtttatc tttgtgtgat attcttgatt tttttctact taatctgata 7560
agtgagctat tcactttagg tttaggatga aaatattctc ttggaaccat acttaatata 7620
gaaatatcaa cttctgccat taaaagtaat gccaatgagc gttttgtatt taataatctt 7680
ttagcaaacc cgtattccac gattaaataa atctcattag ctatactatc aaaaacaatt 7740
ttgcgtatta tatccgtact tatgttataa ggtatattac catatatttt ataggattgg 7800
tttttaggaa atttaaactg caatatatcc ttgtttaaaa cttggaaatt atcgtgatca 7860

```
acaagtttat tttctgtagt tttgcataat ttatggtcta tttcaatggc agttacgaaa   7920

ttacacctct ttactaattc aagggtaaaa tggccttttc ctgagccgat ttcaaagata   7980

ttatcatgtt catttaatct tatatttgtc attattttat ctatattatg ttttgaagta   8040

ataaagtttt gactgtgttt tatatttttc tcgttcatta taaccctctt taatttggtt   8100

atatgaattt tgcttattaa cgattcatta taaccactta tttttgttt ggttgataat   8160

gaactgtgct gattacaaaa atactaaaaa tgcccatatt ttttcctcct tataaaatta   8220

gtataattat agcacgagct ctgataaata tgaacatgat gagtgatcgt taaatttata   8280

ctgcaatcgg atgcgattat tgaataaaag atatgagaga tttatctaat ttcttttttc   8340

ttgtaaaaaa agaaagttct taaaggtttt atagttttgg tcgtagagca cacggtttaa   8400

cgacttaatt acgaagtaaa taagtctagt gtgttagact ttatgaaatc tatatacgtt   8460

tatatatatt tattatccgg aggtgtagca tgtctcattc aattttgagg gttgccagag   8520

ttaaaggatc aagtaataca aacgggatac aaagacataa tcaaagagag aataaaaact   8580

ataataataa agacataaat catgaggaaa catataaaaa ttatgatttg attaacgcac   8640

aaaatataaa gtataaagat aaaattgatg aaacgattga tgagaattat tcagggaaac   8700

gtaaaattcg gtcagatgca attcgacatg tggacggact ggttacaagt gataaagatt   8760

tctttgatga tttaagcgga gaagaaatag aacgattttt taaagatagc ttggagttt    8819
```

```
<210> SEQ ID NO 14
<211> LENGTH: 704
<212> TYPE: DNA
<213> ORGANISM: Artificial Sequence
<220> FEATURE:
<223> OTHER INFORMATION: Reporter gene

<400> SEQUENCE: 14

ccgggacagg cattgaacga tgagctacaa tgaacaagat caacatttcc cataaggagc     60

gtgaacgtca tgatttcgca cttcagctgg aaaccgttat tcaaaaaaga gaaactgccc    120

ggatggcgga tttcatttta ctggcagggt acgcattacg aagggattta ccataagtcc    180

ggagacattg aatggggaca cacacatccg ggaaaagaag agccggctct cgtaaaagag    240

ctgcatgaat taatgcttta tcacatatat gactgaaagc taaaagctca gccgcaccag    300

gctgggcttt tctttttcct tccgctattt accacaccgt tttccgaatg agatgccgtt    360

tgattcacca taatacgtag tacaaagcgg caaacagcat tgggtgaagc cgagctggca    420

atggttttca ttccgaaaat catcggctgg tgcaattcca gcaaacccaa ccatactact    480

ttataaagga gatcatacaa atggcaaaca acaactcttc aaaccaacta gtagtacccg    540

gcgctgctca agcaatcgac caaatgaaat acgaaattgc ttctgagttc ggcgtaaacc    600

ttggcggaga aacaacttct cgtgcaaacg gttctgtcgg aggagaaatc actaaacgtt    660

tagtatcttt cgcacagcag aacatgggcg gccaaggcgt acaa                     704
```